United States Patent
St. Pierre et al.

(10) Patent No.: US 9,646,136 B2
(45) Date of Patent: May 9, 2017

(54) PHYSIOLOGICAL PARAMETER MEASURING PLATFORM DEVICE SUPPORTING MULTIPLE WORKFLOWS

(71) Applicant: Welch Allyn, Inc., Skaneateles Falls, NY (US)

(72) Inventors: Shawn C. St. Pierre, Syracuse, NY (US); Esther N. Ahn, San Francisco, CA (US); Eric J. Bailey, Oakland, CA (US); Michael D. Garrant, Marcellus, NY (US); Roger W. Graves, San Francisco, CA (US); Jennifer M. Kilian, New York, NY (US); Thomas A. Myers, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 14/994,576

(22) Filed: Jan. 13, 2016

(65) Prior Publication Data

US 2016/0125151 A1    May 5, 2016

Related U.S. Application Data

(63) Continuation of application No. 12/751,579, filed on Mar. 31, 2010, now Pat. No. 9,265,429.

(Continued)

(51) Int. Cl.
    *G08B 1/08*    (2006.01)
    *G06F 19/00*   (2011.01)
    (Continued)

(52) U.S. Cl.
    CPC ...... *G06F 19/3406* (2013.01); *A61B 5/02055* (2013.01); *A61B 5/7445* (2013.01);
    (Continued)

(58) Field of Classification Search
CPC combination set(s) only.
See application file for complete search history.

(56) References Cited

U.S. PATENT DOCUMENTS

| 5,140,519 A | 8/1992 | Friesdorf et al. |
| D366,460 S | 1/1996 | Jorgenson |
| (Continued) | | |

FOREIGN PATENT DOCUMENTS

| CN | 1356783 A | 7/2002 |
| CN | 1649538 A | 8/2005 |
| (Continued) | | |

OTHER PUBLICATIONS

Adams, A.P., Breathing System Disconnections, Br. J. Anaesth, 1994, vol. 73, No. 1, pp. 46-54.

(Continued)

*Primary Examiner* — Travis Hunnings
(74) *Attorney, Agent, or Firm* — Merchant & Gould P.C.

(57) ABSTRACT

A device obtains a series of measurements of a physiological parameter of a monitored patient when the device is operating within a monitoring workflow. The device displays a monitoring workflow home screen when the device is operating within the monitoring workflow. The monitoring workflow home screen contains a representation of the physiological parameter of the monitored patient. In addition, the device obtains a measurement of the physiological parameter of each patient in a series of patients when the device is operating within a non-monitoring workflow. The device displays a non-monitoring workflow home screen when the device is operating within the non-monitoring workflow. The non-monitoring workflow home screen contains a representation of the physiological parameter of a (Continued)

given patient in the series of patients. The monitoring workflow home screen is different than the non-monitoring workflow home screen.

18 Claims, 27 Drawing Sheets

Related U.S. Application Data

(60) Provisional application No. 61/243,872, filed on Sep. 18, 2009.

(51) Int. Cl.
*A61B 5/0205* (2006.01)
*A61B 5/00* (2006.01)
*G06Q 10/06* (2012.01)
*G06Q 50/22* (2012.01)

(52) U.S. Cl.
CPC ........ *A61B 5/7475* (2013.01); *G06F 19/3487* (2013.01); *G06Q 10/06* (2013.01); *G06Q 50/22* (2013.01); *A61B 5/746* (2013.01)

(56) References Cited

U.S. PATENT DOCUMENTS

| | | | |
|---|---|---|---|
| 5,701,894 A | 12/1997 | Cherry et al. | |
| D427,574 S | 7/2000 | Sawada et al. | |
| 6,219,046 B1 | 4/2001 | Thomas et al. | |
| D454,139 S | 3/2002 | Feldcamp | |
| 6,364,834 B1 | 4/2002 | Reuss et al. | |
| 6,398,727 B1 | 6/2002 | Bui et al. | |
| 6,416,471 B1 | 7/2002 | Kumar et al. | |
| 6,469,717 B1 | 10/2002 | Wineke et al. | |
| D465,226 S | 11/2002 | Friedman | |
| D468,322 S | 1/2003 | Walker et al. | |
| 6,535,714 B2 | 3/2003 | Melker et al. | |
| 6,658,276 B2 | 12/2003 | Kianl et al. | |
| 6,675,031 B1 | 1/2004 | Porges et al. | |
| 6,707,476 B1 | 3/2004 | Hochstedler | |
| 6,783,573 B2 | 8/2004 | Richardson | |
| 6,828,910 B2 | 12/2004 | VanRyzin et al. | |
| D510,582 S | 10/2005 | Hoang et al. | |
| D523,440 S | 6/2006 | Hernandez et al. | |
| D525,982 S | 8/2006 | Suzuki | |
| D527,011 S | 8/2006 | Bixler | |
| 7,124,366 B2 | 10/2006 | Foreman et al. | |
| 7,134,994 B2 | 11/2006 | Alpert et al. | |
| D545,829 S | 7/2007 | Fletcher | |
| 7,336,187 B2 * | 2/2008 | Hubbard, Jr. ....... | G06F 19/3418 340/286.07 |
| D575,296 S | 8/2008 | Fairfield et al. | |
| 7,409,399 B2 | 8/2008 | Miyamoto | |
| D576,634 S | 9/2008 | Clark et al. | |
| D579,456 S | 10/2008 | Chen et al. | |
| 7,433,827 B2 | 10/2008 | Rosenfeld et al. | |
| D586,818 S | 2/2009 | Luck | |
| D590,413 S | 4/2009 | Bhat et al. | |
| D590,414 S | 4/2009 | Bhat et al. | |
| D592,156 S | 5/2009 | Drews et al. | |
| D592,675 S | 5/2009 | Bhat et al. | |
| 7,565,616 B2 | 7/2009 | Buchmann | |
| D598,923 S | 8/2009 | Chen et al. | |
| D598,929 S | 8/2009 | Bhat et al. | |
| D599,358 S | 9/2009 | Hoefnagels et al. | |
| D599,398 S | 9/2009 | Laidlaw et al. | |
| D603,416 S | 11/2009 | Poling et al. | |
| D607,463 S | 1/2010 | Krieter et al. | |
| D608,366 S | 1/2010 | Matas | |
| 7,662,106 B2 | 2/2010 | Daniels et al. | |
| D612,860 S | 3/2010 | Tarara et al. | |
| RE41,236 E * | 4/2010 | Seely ................ | A61B 5/0002 128/903 |
| D614,634 S | 4/2010 | Nilsen | |
| 7,765,479 B2 | 7/2010 | Goodwin et al. | |
| 7,774,060 B2 | 8/2010 | Westenskow et al. | |
| 7,782,302 B2 | 8/2010 | Lee et al. | |
| 7,787,946 B2 | 8/2010 | Stahmann et al. | |
| 7,810,497 B2 | 10/2010 | Pittman et al. | |
| D632,699 S | 2/2011 | Judy et al. | |
| 7,895,527 B2 | 2/2011 | Zaleski et al. | |
| D635,150 S | 3/2011 | Sykes et al. | |
| D637,603 S | 5/2011 | Godgart | |
| 7,937,134 B2 | 5/2011 | Uber et al. | |
| D640,264 S | 6/2011 | Fujii et al. | |
| 7,967,759 B2 | 6/2011 | Couvillon, Jr. | |
| D643,043 S | 8/2011 | Loken et al. | |
| 8,001,967 B2 | 8/2011 | Wallace et al. | |
| 8,020,558 B2 | 9/2011 | Christopher et al. | |
| D646,689 S | 10/2011 | Ulliot | |
| 8,028,701 B2 | 10/2011 | Al-Ali et al. | |
| 8,038,593 B2 | 10/2011 | Friedman et al. | |
| 8,046,705 B2 | 10/2011 | Hunleth et al. | |
| 8,055,514 B2 * | 11/2011 | Elsholz ................ | G06F 19/327 705/2 |
| 8,078,983 B2 | 12/2011 | Davis et al. | |
| D652,051 S | 1/2012 | Judy et al. | |
| D656,153 S | 3/2012 | Imamura et al. | |
| D656,157 S | 3/2012 | Khan et al. | |
| D656,946 S | 4/2012 | Judy et al. | |
| D657,368 S | 4/2012 | Magee et al. | |
| D658,196 S | 4/2012 | Wood et al. | |
| D658,667 S | 5/2012 | Cho et al. | |
| D664,971 S | 8/2012 | Lee et al. | |
| D664,984 S | 8/2012 | Lee et al. | |
| D666,625 S | 9/2012 | Gilmore et al. | |
| D667,837 S | 9/2012 | Magee et al. | |
| D667,838 S | 9/2012 | Magee et al. | |
| D674,401 S | 1/2013 | Trumble et al. | |
| D675,218 S | 1/2013 | Arnold et al. | |
| D676,863 S | 2/2013 | Ho Kushner et al. | |
| D676,864 S | 2/2013 | Velasco et al. | |
| D688,685 S | 8/2013 | Rhee et al. | |
| D689,899 S | 9/2013 | Lee et al. | |
| D695,781 S | 12/2013 | Edwards et al. | |
| 8,732,604 B2 | 5/2014 | Okamoto et al. | |
| 9,055,870 B2 * | 6/2015 | Meador ................ | A61B 5/0205 |
| 9,265,429 B2 * | 2/2016 | St. Pierre ........... | A61B 5/02055 |
| 2002/0054141 A1 | 5/2002 | Yen et al. | |
| 2002/0078097 A1 | 6/2002 | Chen et al. | |
| 2002/0126137 A1 | 9/2002 | Kaestner, Jr. | |
| 2002/0177758 A1 | 11/2002 | Schoenberg et al. | |
| 2003/0060727 A1 | 3/2003 | Kline | |
| 2003/0135087 A1 * | 7/2003 | Hickle ................ | G06F 19/3406 600/26 |
| 2004/0002874 A1 | 1/2004 | Shaffer et al. | |
| 2004/0088199 A1 | 5/2004 | Childress et al. | |
| 2004/0111045 A1 * | 6/2004 | Sullivan ................ | A61B 5/11 600/595 |
| 2005/0114374 A1 | 5/2005 | Juszkiewicz et al. | |
| 2005/0229110 A1 | 10/2005 | Gegner et al. | |
| 2005/0288571 A1 | 12/2005 | Perkins | |
| 2006/0149597 A1 | 7/2006 | Powell et al. | |
| 2006/0200009 A1 | 9/2006 | Wekell et al. | |
| 2006/0228096 A1 | 10/2006 | Hoshino et al. | |
| 2006/0229557 A1 | 10/2006 | Fathallah et al. | |
| 2006/0247948 A1 | 11/2006 | Ellis et al. | |
| 2007/0000494 A1 | 1/2007 | Banner et al. | |
| 2007/0067005 A1 | 3/2007 | Schatz et al. | |
| 2007/0150810 A1 | 6/2007 | Katz et al. | |
| 2007/0156456 A1 | 7/2007 | McGillin et al. | |
| 2007/0167173 A1 | 7/2007 | Halcrow et al. | |
| 2007/0167694 A1 | 7/2007 | Causevic et al. | |
| 2007/0174079 A1 | 7/2007 | Kraus | |
| 2007/0185390 A1 * | 8/2007 | Perkins ................ | A61B 5/0002 600/300 |
| 2007/0197878 A1 | 8/2007 | Shklarski | |
| 2007/0203744 A1 | 8/2007 | Scholl | |
| 2007/0215157 A1 | 9/2007 | Straw | |
| 2007/0276261 A1 | 11/2007 | Banet et al. | |
| 2008/0012833 A1 | 1/2008 | Beck et al. | |
| 2008/0021379 A1 | 1/2008 | Hickle | |
| 2008/0055074 A1 | 3/2008 | Gao et al. | |

(56) References Cited

U.S. PATENT DOCUMENTS

| | | |
|---|---|---|
| 2008/0058609 A1 | 3/2008 | Garibaldi et al. |
| 2008/0058614 A1 | 3/2008 | Banet et al. |
| 2008/0072896 A1 | 3/2008 | Setzer et al. |
| 2008/0077026 A1 | 3/2008 | Banet et al. |
| 2008/0086691 A1 | 4/2008 | Hopermann et al. |
| 2008/0103375 A1 | 5/2008 | Kiani |
| 2008/0115081 A1 | 5/2008 | Sankaravadivelu et al. |
| 2008/0155406 A1 | 6/2008 | Naka |
| 2008/0208812 A1 | 8/2008 | Quoc et al. |
| 2008/0229248 A1 | 9/2008 | Fagans et al. |
| 2008/0249377 A1 | 10/2008 | Molducci et al. |
| 2008/0249801 A1 | 10/2008 | Zaleski |
| 2008/0281168 A1 | 11/2008 | Gibson et al. |
| 2008/0281637 A1 | 11/2008 | Matz |
| 2008/0318529 A1 | 12/2008 | Harb |
| 2009/0005651 A1 | 1/2009 | Ward et al. |
| 2009/0054743 A1 | 2/2009 | Stewart |
| 2009/0054798 A1 | 2/2009 | Varney et al. |
| 2009/0112630 A1 | 4/2009 | Collins, Jr. et al. |
| 2009/0131761 A1 | 5/2009 | Moroney, III et al. |
| 2009/0132588 A1 | 5/2009 | Mahesh et al. |
| 2009/0143652 A1 | 6/2009 | Warburton et al. |
| 2009/0149927 A1 | 6/2009 | Kneuer et al. |
| 2009/0158415 A1 | 6/2009 | Dillon |
| 2009/0240116 A1 | 9/2009 | Bluth |
| 2009/0240193 A1 | 9/2009 | Mensinger et al. |
| 2009/0241958 A1 | 10/2009 | Baker, Jr. |
| 2009/0275805 A1 | 11/2009 | Lane et al. |
| 2009/0275810 A1 | 11/2009 | Ayers et al. |
| 2009/0282340 A1 | 11/2009 | Akaike et al. |
| 2009/0306482 A1 | 12/2009 | Davis et al. |
| 2009/0306488 A1 | 12/2009 | Al-Ali et al. |
| 2009/0312648 A1 | 12/2009 | Zhang et al. |
| 2010/0050075 A1 | 2/2010 | Thorson et al. |
| 2010/0069004 A1 | 3/2010 | Bioebaum |
| 2010/0094096 A1 | 4/2010 | Petruzzelli et al. |
| 2010/0097380 A1 | 4/2010 | Daniels et al. |
| 2010/0218766 A1 | 9/2010 | Milne |
| 2010/0274098 A1 | 10/2010 | Belford et al. |
| 2010/0324380 A1 | 12/2010 | Perkins et al. |
| 2011/0010621 A1 | 1/2011 | Wallaert et al. |
| 2011/0015502 A1 | 1/2011 | Peyser |
| 2011/0169644 A1 | 7/2011 | Muhsin et al. |
| 2011/0190600 A1 | 8/2011 | McKenna et al. |
| 2011/0205577 A1 | 8/2011 | Mori et al. |
| 2011/0209707 A1 | 9/2011 | Terhark |
| 2011/0227739 A1 | 9/2011 | Gilham et al. |
| 2011/0245630 A1* | 10/2011 | St. Pierre ............... G06F 19/322 600/301 |
| 2011/0246565 A1 | 10/2011 | Irwin et al. |
| 2011/0276338 A1 | 11/2011 | Warner et al. |
| 2011/0290250 A1 | 12/2011 | Olson et al. |
| 2011/0313301 A1 | 12/2011 | Lane et al. |
| 2012/0000470 A1 | 1/2012 | Milne et al. |
| 2012/0016251 A1 | 1/2012 | Zhang et al. |
| 2012/0048090 A1 | 3/2012 | Etter et al. |
| 2012/0095778 A1 | 4/2012 | Gross et al. |
| 2012/0096367 A1 | 4/2012 | DelloStritto et al. |
| 2012/0110444 A1 | 5/2012 | Li et al. |
| 2012/0117099 A1 | 5/2012 | Gross |
| 2012/0215075 A1 | 8/2012 | Surace et al. |
| 2012/0296183 A1 | 11/2012 | Kinsley et al. |
| 2013/0151285 A1 | 6/2013 | McLaren et al. |
| 2013/0265327 A1 | 10/2013 | Vann et al. |
| 2013/0267792 A1 | 10/2013 | Petersen et al. |
| 2013/0267793 A1 | 10/2013 | Meador et al. |
| 2013/0267861 A1* | 10/2013 | Vassallo ............... G06F 19/3406 600/532 |
| 2013/0268283 A1 | 10/2013 | Vann et al. |
| 2013/0293373 A1 | 11/2013 | Gegner et al. |
| 2013/0311926 A1 | 11/2013 | Keegan et al. |
| 2014/0040429 A1 | 2/2014 | Irwin et al. |
| 2014/0098209 A1 | 4/2014 | Neff |
| 2014/0108041 A1 | 4/2014 | Bechtel et al. |
| 2014/0135588 A1 | 5/2014 | Al-Ali et al. |

FOREIGN PATENT DOCUMENTS

| | | |
|---|---|---|
| CN | 101069638 A | 11/2007 |
| EP | 0 707 824 A2 | 4/1996 |
| EP | 2 093 683 A2 | 8/2009 |
| GB | 2 409 951 A | 7/2005 |
| JP | 10-91687 A | 4/1998 |
| JP | 3682617 B2 | 8/2005 |
| JP | 2010-015193 A | 1/2010 |
| WO | 01-26021 A1 | 4/2001 |
| WO | 01-89362 A2 | 11/2001 |
| WO | 2006-076498 A2 | 7/2006 |
| WO | 2010-102069 A2 | 9/2010 |
| WO | 2011-001302 A1 | 1/2011 |

OTHER PUBLICATIONS

Al-Qutayri et al.; Framework for Secure Wireless Health monitoring and remote Access System, Inderscience Enterprises Ltd. copyright 2010, 19 pages.

Capnography: An Objecti ve Tool for Assessing Respiratory Status, Physio-Control, Inc., 2008, pp. 1-8.

Colin Prodigy Press-Mate Prodigy II® Portable Vital Signs Monitors, DRE, Copyright 2009, accessed at: http://www.dremed.com/catalog/product_info.php/products_id/1181; 5 pages.

Fingertip Pulse Oximeter SPO2 Monitor Oxygen Oximeter; Copyright 1995-2010, accessed at: http://74.125.45.132/search?q=cache:ANfHne9je7gJ:cgi.ebay.com.sg/ws/eBayISAPI.dll%3FViewItem%26item%3D260412542031+"Fingertip+Pulse+Oximeter+SPO2+Monitor+Oxigen+Oximeter"&cd=2&hl=en&ct=clnk&gl=us; 6 pages.

Handheld Pulse Oximeter PM-60A, Contec Medical System Co. Ltd., Jul. 31, 2009; accessed at: http://www.tradeindia.com/selloffer/1858593/Handheld-Pulse-Oximeter-PM-60A.html; 5 pages.

International Search Report and Written Opinion in PCT/US2010/048450 dated Apr. 12, 2011, 9 pages.

International Search Report and Written Opinion in PCT/US2013/031342 mailed Jun. 24, 2013, 12 pages.

International Search Report and Written Opinion in PCT/US2013/031458 mailed Jun. 28, 2013, 10 pages.

International Search Report and Written Opinion in PCT/US2013/031486 mailed Jun. 28, 2013, 10 pages.

International Search Report and Written Opinion in PCT/US2013/031582 mailed Jun. 28, 2013, 11 pages.

Kozlovszky et al.; Network and Service Management and Diagnostics Solution of a Remote Patient Monitoring System, IEEE copyright 2011, 4 pages.

Lamberti et al.; Ubiquitous Real-Time Monitoring of Critical-Care Patients in Intensive Care Units, IEEE copyright 2003, 4 pages.

mCare 300 Vital Signs Monitor, Spacelabs Medical, Inc., Copyright 2006, 4 pages.

Multiple Vital Signs from One Non-invasive Sensor, Starr™ Life Sciences Corp., Copyright 2009, accessed at: http://www.starrlifesciences.com/mouseox.html; 1 page.

Nag et al., Wireless E-jacket ofr Multiparameter Biophysical Monitoring and Telemedicine Applications, Medial Devices and Biosensors, 2006, 3rd IEEE/EMBS Inernational Summer School, Sep. 4-6, 2006, pp. 40-44.

NTIA Handheld Pulse Oximeter, Frontline Systems; Dec. 31, 2009, accessed at: http://www.tradeindia.com/fp385774/NTIA-Handheld-Pulse-Oximeter.html; 3 pages.

O'Donoughue et al., Design and Implementation of a Framework for Monitoring Patients in Hospitals Using Wireless Sensors in Ad Hoc configuration, Engineering in Medicine and Biology Society, EMBS '06, 28th Annual International Confernece of the IEEE, vol., No., Aug. 30, 2006-Sep. 3, 2066, pp. 6449-6452.

Panorama™ Central Station, Surgical Product Guide copyright 2011, 2 pages.

Portable Patient Monitors, Welch Allyn, Copyright 2005-2006 MedDirect, Copyright 2005-2006, accessed at: http://www.meddirect.co.nz/Product.aspx?ProductId=3476; 1 page.

Station—Dictionary.com, [online], retrieved on Sep. 2, 2014, Retrived from, <URL:http://dictionary.reference.com/browse/station>, 4 pages.

(56) References Cited

OTHER PUBLICATIONS

U.S. Appl. No. 29/417,592, filed Apr. 5, 2012.
U.S. Appl. No. 29/417,611, filed Apr. 5, 2012.
Ultraview DM3—Dual Mode Vital Signs Monitor, Spacelabs Healthcare, Copyright 2010, 4 pages.
Zhao et al.; A Portable, Low-Cost, Batter-Powered Wireless Monitoring System for Obtaining Varying Physiologic Parameters from Multiple Subjects, IEEE copyright 2006, 4 pages.
Extended European Search Report for PCT/US2010/048450, Nov. 18, 2014, 7 pages.

* cited by examiner

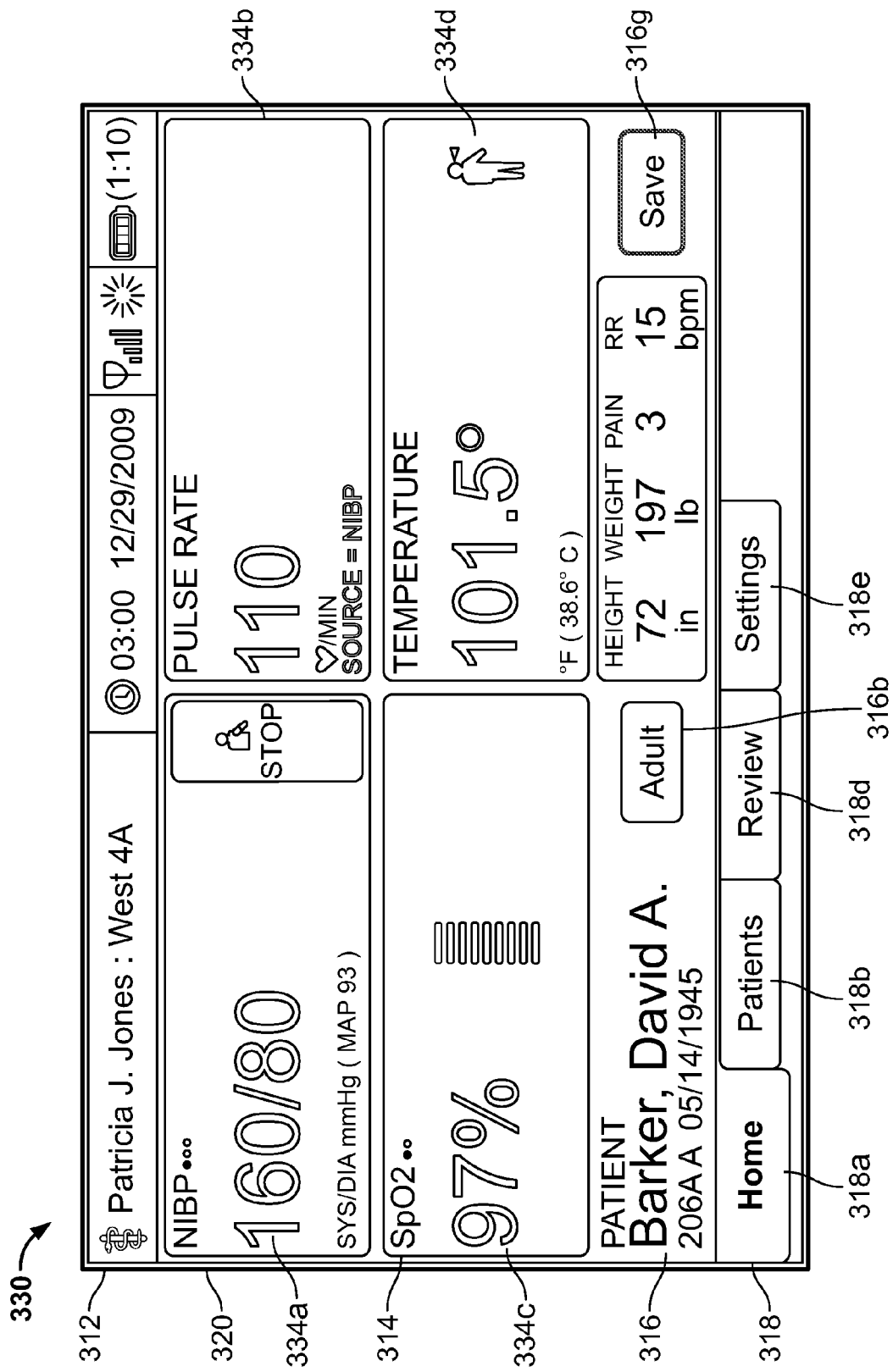

US 9,646,136 B2

PHYSIOLOGICAL PARAMETER MEASURING PLATFORM DEVICE SUPPORTING MULTIPLE WORKFLOWS

RELATED APPLICATION

The present application claims priority to U.S. Provisional Patent Application Ser. No. 61/243,872, filed Sep. 18, 2009, the entirety of which is hereby incorporated by reference.

BACKGROUND

Health care practitioners, such as nurses and physicians, use various types of health-care equipment to assist with the task of providing health care to a patient, also referred to herein as a health-care recipient. Some health-care equipment, referred to as single function equipment, is designed to perform a particular function, such as temperature measurement. Some health-care equipment, referred to as multi-function equipment, is designed to implement the performance of more than one function, such as temperature measurement and blood pressure measurement. Such multi-function equipment may impose excess bulk and/or weight upon a user if such multi-function equipment is used for only one function or a subset of the functions implemented by the multi-function equipment.

SUMMARY

In one aspect, a physiological measuring platform (PMP) device comprises a central processing unit (CPU) that is configured to control operation of the PMP device. The PMP device also comprises a display screen. In addition, the PMP device comprises one or more computer readable data storage media storing software instructions that, when executed by the CPU, cause the PMP device to obtain a series of measurements of a physiological parameter of a monitored patient when the PMP device is operating within a monitoring workflow. The software instructions, when execute by the CPU, further cause the PMP device to display, on the display screen, a monitoring workflow home screen when the PMP device is operating within the monitoring workflow. The monitoring workflow home screen contains a first representation of the physiological parameter of the monitored patient. The first representation is based on a measurement in the series of measurements. In addition, the software instructions, when executed by the CPU, further cause the PMP device to obtain a measurement of the physiological parameter of each patient in a series of patients when the PMP device is operating within a non-monitoring workflow. In addition, the software instructions, when executed by the CPU, further cause the PMP device to display, on the display screen, a non-monitoring workflow home screen when the PMP device is operating within the non-monitoring workflow. The non-monitoring workflow home screen contains a second representation of the physiological parameter of a given patient in the series of patients. The second representation is based on the measurement of the physiological parameter of the given patient in the series of patients. The monitoring workflow home screen is different than the non-monitoring workflow home screen.

Another aspect is a method for performing physiological parameter measurements for a plurality of patients. The method comprises, displaying, by a physiological measurement platform (PMP) device, a settings screen on a display screen, the settings screen enabling a user to select a workflow within which the PMP device is to operate. The method further comprises, when the PMP device is operating within a monitoring workflow: obtaining, by the PMP device, a series of measurements of a physiological parameter of a monitored patient; and displaying, by the PMP device, a monitoring workflow home screen on the display screen. The monitoring workflow home screen contains a first representation of the physiological parameter of the given patient, the first representation based on a measurement in the series of measurements. The method also comprises when the PMP device is operating within a non-monitoring workflow: obtaining, by the PMP device, a measurement of the physiological parameter of each patient in a series of patients; and displaying, by the PMP device, a non-monitoring workflow home screen on the display screen. The non-monitoring workflow home screen contains a second representation of the physiological parameter of a given patient in the series of patients, the second representation based on the measurement of the physiological parameter of the given patient in the series of patients.

Yet another aspect is a method comprising obtaining, by a physiological measuring platform (PMP) device, a measurement of a physiological parameter of a given patient. The method also comprises displaying an alarms screen on a display screen of the PMP device. The alarms screen enables a user of the PMP device to configure global alarm settings and parameter-specific alarm settings. The alarms screen includes a compressed parameter reporting area. The compressed parameter reporting area contains a compressed parameter frame containing a representation of the physiological parameter of the given patient.

Yet another aspect is a method comprising obtaining, by a physiological measuring platform (PMP) device, a measurement of a physiological parameter of a patient. The method also comprises displaying, on a display screen of the PMP device, a parameter reporting area containing a representation of the physiological parameter of the patient. In addition, the method comprises displaying, on the display screen of the PMP device, an alarm message describing a first alarm when the first alarm is active. The first alarm is active when the measurement of the physiological parameter is outside an alarm range for the physiological parameter. The method also comprises modifying, on the display screen, the alarm message to describe a second alarm when the second alarm is active and when a user selects the alarm message.

Yet another aspect is a method comprising displaying, on a display screen of a physiological measuring platform (PMP) device a settings screen. The settings screen containing a set of interval program selection controls. The method also comprises receiving, by the PMP device, a selection by a user of one of the interval program selection controls. Furthermore, the method comprises obtaining, by the PMP device, measurements of a physiological parameter of a patient. In addition, the method comprises recording, by the PMP device, measurements of the physiological parameter at intervals specified by an interval program for a duration specified by the interval program. The interval program corresponds to the selected one of the interval program selection controls.

Yet another aspect is a computer-readable storage medium comprising software instructions that, when executed, cause a physiological measurement platform (PMP) device to display, on a display screen, a settings screen that enables a user to select a workflow within which the PMP device is to operate. When the user selects a monitoring workflow from the settings screen, the software instructions, when executed, cause the PMP device to:

obtain a series of measurements of a physiological parameter of a monitored patient;

display a monitoring workflow home screen on the display screen, the monitoring workflow home screen containing a first representation of the physiological parameter, the first representation of the physiological parameter based on at least one measurement in the series of measurements; and display, on the display screen, an alarms screen that enables the user to configure global alarm settings and parameter-specific alarm settings. The alarms screen includes a compressed parameter reporting area. The compressed parameter reporting area contains a compressed parameter frame containing a second representation of the physiological parameter of the monitored patient.

When the user selects a spot check workflow from the settings screen, the software instructions, when executed, cause the PMP device to:

obtain a measurement of the physiological parameter of each patient in a series of previously identified patients; and display a spot check workflow home screen on the display screen. The spot check workflow home screen contains a third representation of the physiological parameter of a given patient in the series of previously identified patients. The third representation of the physiological parameter is based on the measurement of the physiological parameter of the given patient in the series of previously identified patients.

When the user selects a triage workflow from the settings screen, the software instructions, when executed, cause the PMP device to:

obtain a measurement of the physiological parameter of each patient in a series of unidentified patients; and display a triage workflow home screen on the display screen. The triage workflow home screen contains a fourth representation of the physiological parameter of a given patient in the series of unidentified patients, the fourth representation of the physiological parameter based on the measurement of the given patient in the series of unidentified patients.

The monitoring workflow home screen, the spot check workflow home screen, and the triage workflow home screen are each different from one another. The software instructions, when executed, also cause the PMP device to display, on the display screen, an alarm message describing a first alarm when the first alarm is active. The first alarm is active when a given measurement of the physiological parameter is outside an alarm range for the physiological parameter. The software instructions, when executed, also cause the PMP device to modify, on the display screen, the alarm message to describe a second alarm when the second alarm is active and when the user selects the alarm message. The software instructions, when executed, also cause the PMP device to emit an alarm sound when the first alarm is active. The software instructions, when executed, also cause the PMP device to suspend emitting the alarm sound for a given time period in response to user input. The software instructions, when executed, also cause the PMP device to extend the given time period when the PMP device receives additional user input before the given time period expires. The software instructions, when executed, also cause the PMP device to resume emitting the alarm sound when the given time period expires.

BRIEF DESCRIPTION OF THE DRAWINGS

The objects and features of the invention can be better understood with reference to the claims and drawings described below. The drawings are not necessarily to scale, and the emphasis is instead generally being placed upon illustrating the principles of the invention. Within the drawings, like reference numbers are used to indicate like parts throughout the various views. Differences between like parts may cause those like parts to be each indicated by different reference numbers. Unlike parts are indicated by different reference numbers.

FIG. 3B illustrates an example spot check workflow home screen.

DETAILED DESCRIPTION

Figure 1:
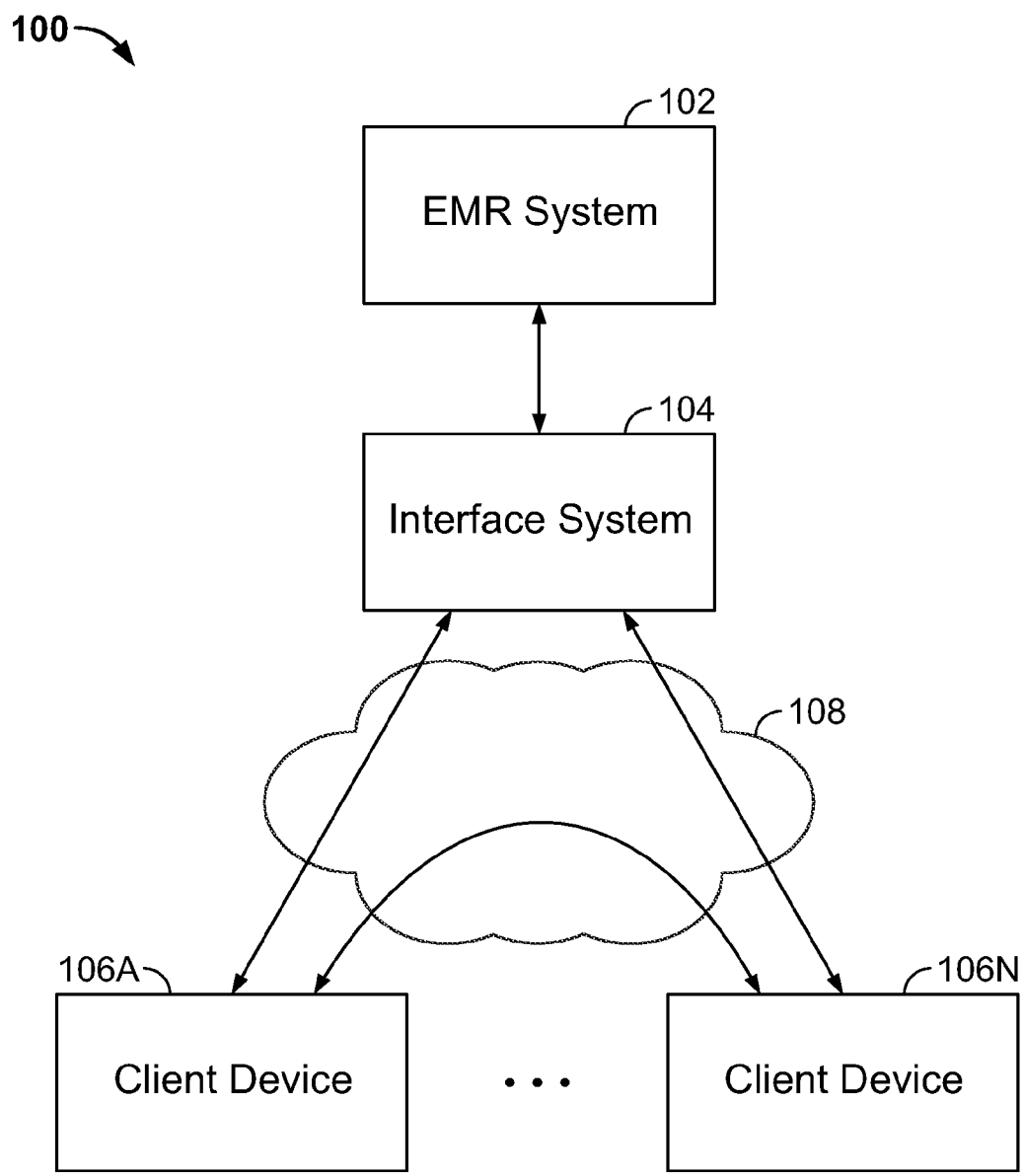
FIG. 1 is a block diagram illustrating an example system for collecting measurements of physiological parameters of patients.

Embodiments of the present invention are directed to a physiological parameter measuring platform (PMP) device having a user interface configured to operate within and transition between each of a monitoring workflow and a non-monitoring workflow. In the following detailed description, references are made to the accompanying drawings that form a part hereof, and in which are shown by way of illustrations specific embodiments or examples. These embodiments may be combined, other embodiments may be utilized, and structural changes may be made without departing from the spirit or scope of the present invention. The following detailed description is therefore not to be taken in a limiting sense and the scope of the present invention is defined by the appended claims and their equivalents.

Referring now to the drawings, in which like numerals refer to like elements through the several figures, aspects of the present invention and an exemplary computing operating environment will be described.

FIG. 1 is a block diagram illustrating an example system 100 for collecting measurements of physiological parameters of patients. As illustrated in the example of FIG. 1, the system 100 comprises an Electronic Medical Records (EMR) system 102, an interface system 104, a set of client devices 106A-106N (collectively, "client devices 106"), and a network 108.

The network 108 is an electronic communication network that facilitates communication between the client devices 106 and the between the client devices 106 and the interface system 104. An electronic communication network is a set of computing devices and links between the computing devices. The computing devices in the network use the links to enable communication among the computing devices in the network. The network 108 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices. In various embodiments, the network 108 includes various types of links. For example, the network 108 can include wired and/or wireless links. Furthermore, in various embodiments, the network 108 is implemented at various scales. For example, the network 108 can be implemented as one or more local area networks (LANs), metropolitan area networks, subnets, wide area networks (such as the Internet), or can be implemented at another scale.

The EMR system 102 is a computing system that allows storage, retrieval, and manipulation of electronic medical records. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data.

Each client device in the set of client devices 106 is a computing device. The client devices 106 can provide various types of functionality. For example, the set of client devices 106 can include one or more PMP devices (such as the PMP device 200). In addition, the set of client devices 106 can include one or more wall-mounted devices. Such wall-mounted devices can have similar functionality to the PMP device 200 but are stationary instead of portable. In addition, the set of client devices 106 can include one or more monitor devices. Such monitor devices can display representations of physiological parameters, but do not directly obtain measurements of the physiological parameters from patients. A monitor device could, for example, be used by a clinician to monitor the physiological parameters of multiple patients at one time.

The client devices 106 can communicate with each other through the network 108. In various embodiments, the client devices 106 can communicate various types of data with each other through the network 108. For example, in embodiments where the set of client devices 106 includes a set of PMP devices and a monitor device, each of the PMP devices can send data representing measurements of physiological parameters of patients to the monitor device. In this way, the monitor device can display representations of physiological parameters to a clinician.

The interface system 104 is a computing system that acts as an interface between the EMR system 102 and the client devices 106. In some embodiments, the interface system 104 is a Connex system. Different EMR systems have different software interfaces. For example, the EMR system used by two different hospitals can have two different software interfaces. The interface system 104 provides a single software interface to each of the client devices 106. The client devices 106 send requests to software interface provided by the interface system 104. When the interface system 104 receives a request from one of the client devices 106, the interface system 104 translates the request into a request that works with the software interface provided by the EMR system 102. The interface system 104 then provides the translated request to the software interface provided by the EMR system 102. When the interface system 104 receives a response from the EMR system 102, the interface system 104 translates the response from a format of the EMR system 102 to a system understood by the client devices 106. The interface system 104 then forwards the translated response to an appropriate one of the client devices 106.

The client devices 106 can send various types of data to the interface system 104 for storage in the EMR system 102 and can receive various types of data from the EMR system 102 through the interface system 104. For example, in some embodiments, the client devices 106 can send measurements of physiological parameters to the interface system 104 for storage in the EMR system 102. In another example, a monitor device can retrieve past measurements of physiological parameters of patients from the EMR system 102 through the interface system 104.

Figure 2A:
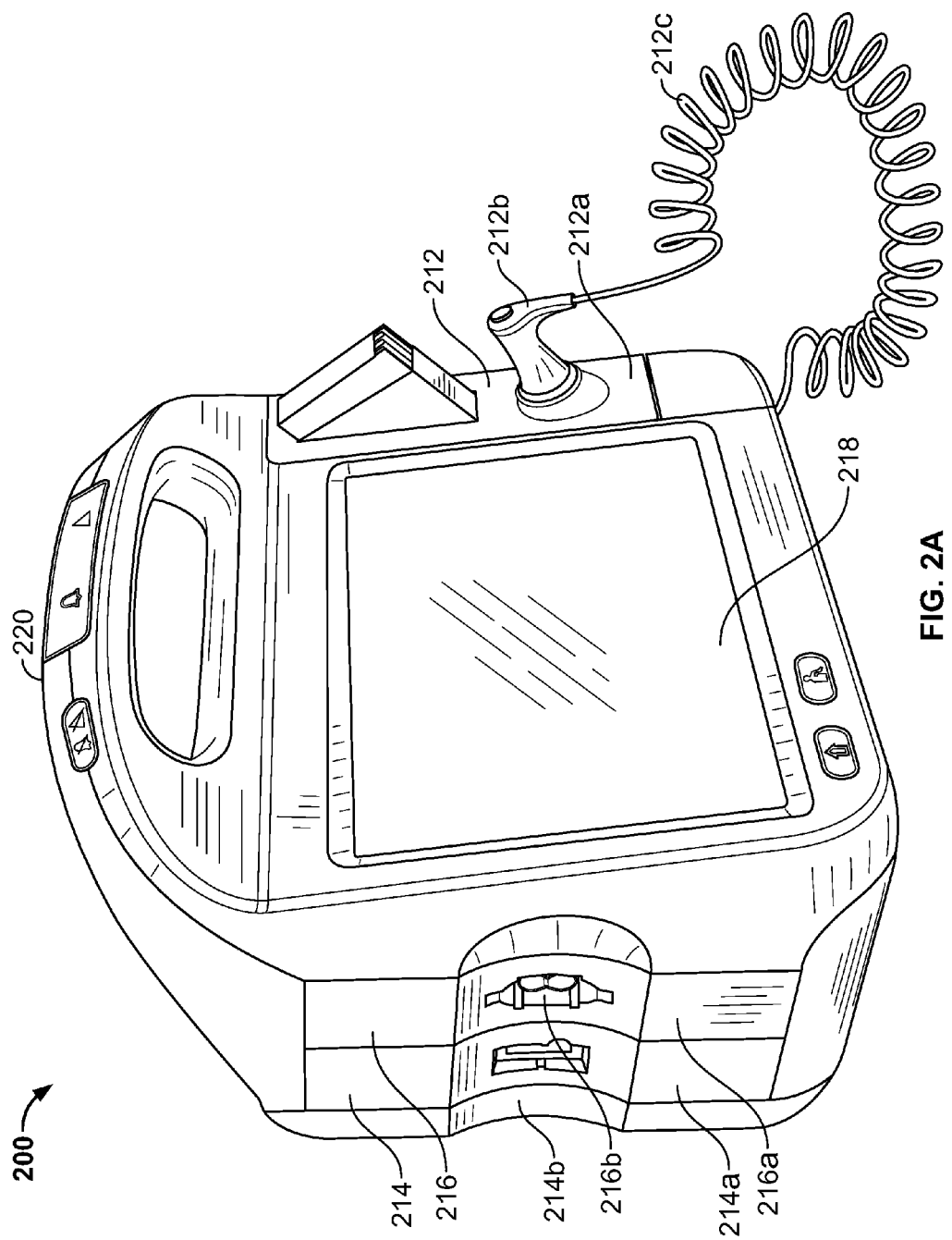
FIG. 2A illustrates a view of an example physiological parameter measuring platform (PMP) device.

FIG. 2A illustrates a view of a PMP device 200. The PMP device 200 is classified and referred to as a portable monitor platform device. The PMP device 200 includes multiple health care equipment (HCE) modules. Each of the HCE modules is configured to measure one or more physiological parameters of a health-care recipient, also referred to herein as a patient.

A temperature measurement module 212 is accessible from the front side of the PMP device 200. A SpO2 module 214 and a non-invasive blood pressure (NIBP) module 216 are accessible from a left hand side of the PMP device 200. An upper handle portion 220 enables the PMP device 200 to be carried by hand.

A front side of the PMP device 200 includes a display screen 218 and an outer surface of the temperature measurement module 212. The temperature measurement module 212 is designed to measure the body temperature of a patient. As used in this document, a "module" is a combination of a physical module structure which typically resides within the PMP device 200 and optional peripheral components (not shown) that typically attach to and reside outside of the PMP device 200.

The temperature measurement module 212 includes a front panel 212a. The front panel 212a has an outer surface that is accessible from the front side of the PMP device 200. The front panel 212a provides access to a wall (not shown) storing a removable probe (not shown), also referred to as a temperature probe, that is attached to a probe handle 212b. The probe and its attached probe handle 212b are tethered to the temperature measurement module 212 via an insulated conductor 212c. The probe is designed to make physical contact with a patient in order to sense a body temperature of the patient.

A left hand side of the PMP device 200 includes an outer surface of the SpO2 module 214 and an outer surface of the NIBP module 216. The SpO2 module 214 is a HCE module designed to measure oxygen content within the blood of a patient. The NIBP module 216 is a HCE module designed to measure blood pressure of a patient.

As shown, the SpO2 module 214 includes a front panel 214a. The front panel 214a includes an outer surface that is accessible from the left side of the PMP device 200. The front panel 214a includes a connector 214b that enables a connection between one or more peripheral SpO2 components (not shown) and a portion of the SpO2 module 214 residing inside the PMP device 200. The peripheral SpO2 components reside external to the PMP device 200. The peripheral SpO2 components are configured to interoperate with the SpO2 module 214 when connected to the SpO2 module 214 via the connector 214b. In some embodiments, the peripheral SpO2 components include a clip that attaches to an appendage of a patient, such as a finger. The clip is designed to detect and measure a pulse and an oxygen content of blood flowing within the patient.

As shown, the NIBP module 216 includes a front panel 216a having an outer surface that is accessible from the left side of the PMP device 200. The front panel 216a includes a connector 216b that enables a connection between one or more peripheral NIBP components (not shown) and a portion of the NIBP module 216 residing inside the PMP device 200. The peripheral NIBP components reside external to the PMP device 200. The peripheral NIBP components are configured to interoperate with the NIBP module 216 when connected to the NIBP module 216 via the connector 216b. In some embodiments, the peripheral NIBP components include an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

The PMP device 200 is able to operate within one or more workflows. A workflow is a series of one or more tasks that a user of the PMP device 200 performs. When the PMP device 200 operates within a workflow, the PMP device 200 provides functionality suitable for assisting the user in performing the workflow. When the PMP device 200 operates within different workflows, the PMP device 200 provides different functionality.

When the PMP device 200 is manufactured, the PMP device 200 is configured to be able to operate within one or more workflows. After the PMP device 200 is manufactured, the PMP device 200 can be reconfigured to operate within one or more additional workflows. In this way, a user can adapt the PMP device 200 for use in different workflows as needed.

In various embodiments, the PMP device 200 operates within various workflows. For example, in some embodiments, the PMP device 200 can operate within a monitoring workflow or a non-monitoring workflow. Example types of non-monitoring workflows include, but are not limited to, a spot check workflow and a triage workflow.

In example embodiments, the names for the workflows can be defined by the user. For example, the user can rename a "triage workflow" as "ED 3 North" or any other nomenclature as desired to provide more context to the user.

When the PMP device 200 is operating within the monitoring workflow, the PMP device 200 obtains a series of measurements of one or more physiological parameters of a single monitored patient over a period of time. In addition, the PMP device 200 displays, on the display screen 218, a monitoring workflow home screen. The monitoring workflow home screen contains a representation of a physiological parameter of the monitored patient. The representation is based on at least one measurement in the series of measurements. A representation of a physiological parameter is a visible image conveying information about the physiological parameter. For example, when the PMP device 200 is operating within the monitoring workflow, the PMP device 200 can obtain a temperature measurement of a single patient once every ten minutes for six hours. In this example, the PMP device 200 displays a monitoring workflow home screen that contains a representation of the patient's body temperature based on a most recent one of the temperature measurements. In this way, a user of the PMP device 200 can monitor the status of the patient.

When the PMP device 200 is operating within a non-monitoring workflow, the PMP device 200 obtains a measurement of one or more physiological parameters from each patient in a series of patients. In addition, the PMP device 200 displays a non-monitoring workflow home screen on the display screen 218. The non-monitoring workflow home screen contains a representation of the physiological parameter of a given patient in the series of patients. The representation is based on the measurement of the physiological parameter of the given patient. In one example, when the PMP device 200 is operating within a spot check workflow, the PMP device 200 obtains blood pressure measurements from a series of previously-identified patients. In this other example, the PMP device 200 displays a spot check workflow home screen containing a blood pressure measurement of a given patient in the series of previously-identified patients. In this way, a user of the PMP device 200 can perform spot checks on the blood pressures of patients who have already been admitted to a hospital. As used in this document, a patient is a previously identified patient when the PMP device 200 stores information regarding the identity of the patient. In another example, when the PMP device 200 is operating within a triage workflow, the PMP device 200 can obtain a single blood pressure measurement from each patient in a series of unidentified patients as the patients arrive at a hospital. In this example, the PMP device 200 displays a triage workflow home screen containing a representation of the patients' blood pressure based on the single blood pressure measurements of the patients. In this way, a user of the PMP device 200 can perform triage on the series of unidentified patients as they arrive. As used in this document, a patient is an unidentified patient when the PMP device 200 does not store information regarding the identity of the patient.

The monitoring workflow home screen is different than the non-monitoring workflow home screen. In various embodiments, the monitoring workflow home screen is different than the non-monitoring workflow home screen in various ways. For example, in some embodiments, the monitoring workflow home screen includes at least one user-selectable control that is not included in the non-monitoring workflow home screen. In other embodiments, a representation of a physiological parameter in the monitoring workflow home screen has a different size than a representation of the same physiological parameter in the non-monitoring workflow home screen.

Figure 2B:
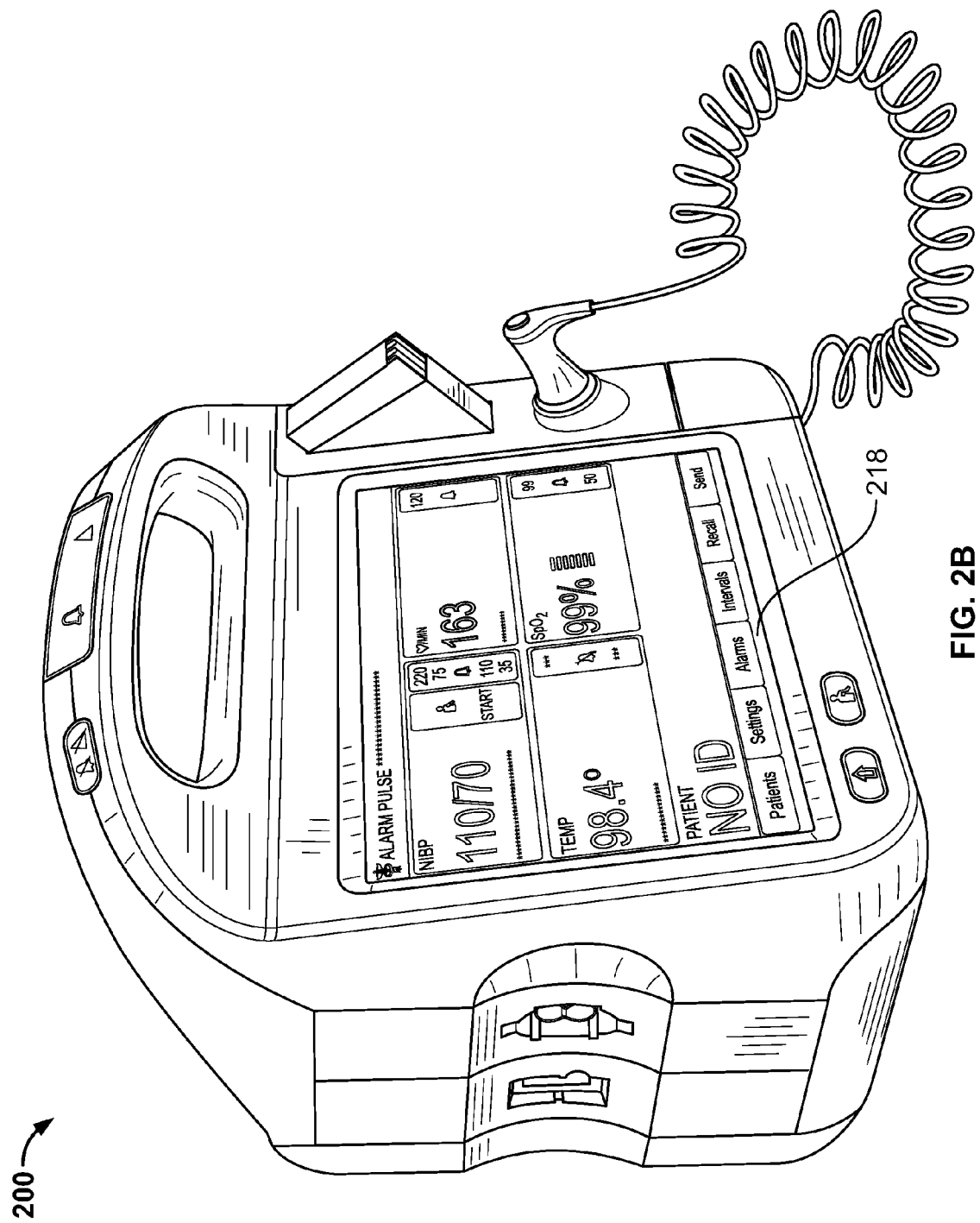
FIG. 2B illustrates an example user interface displayed on a user interface display of the PMP device of FIG. 2A.

FIG. 2B illustrates an example user interface displayed on the display screen 218 of FIG. 2A. The PMP device 200 outputs and displays user interfaces discussed in this document on the display screen 218.

Figure 3A:
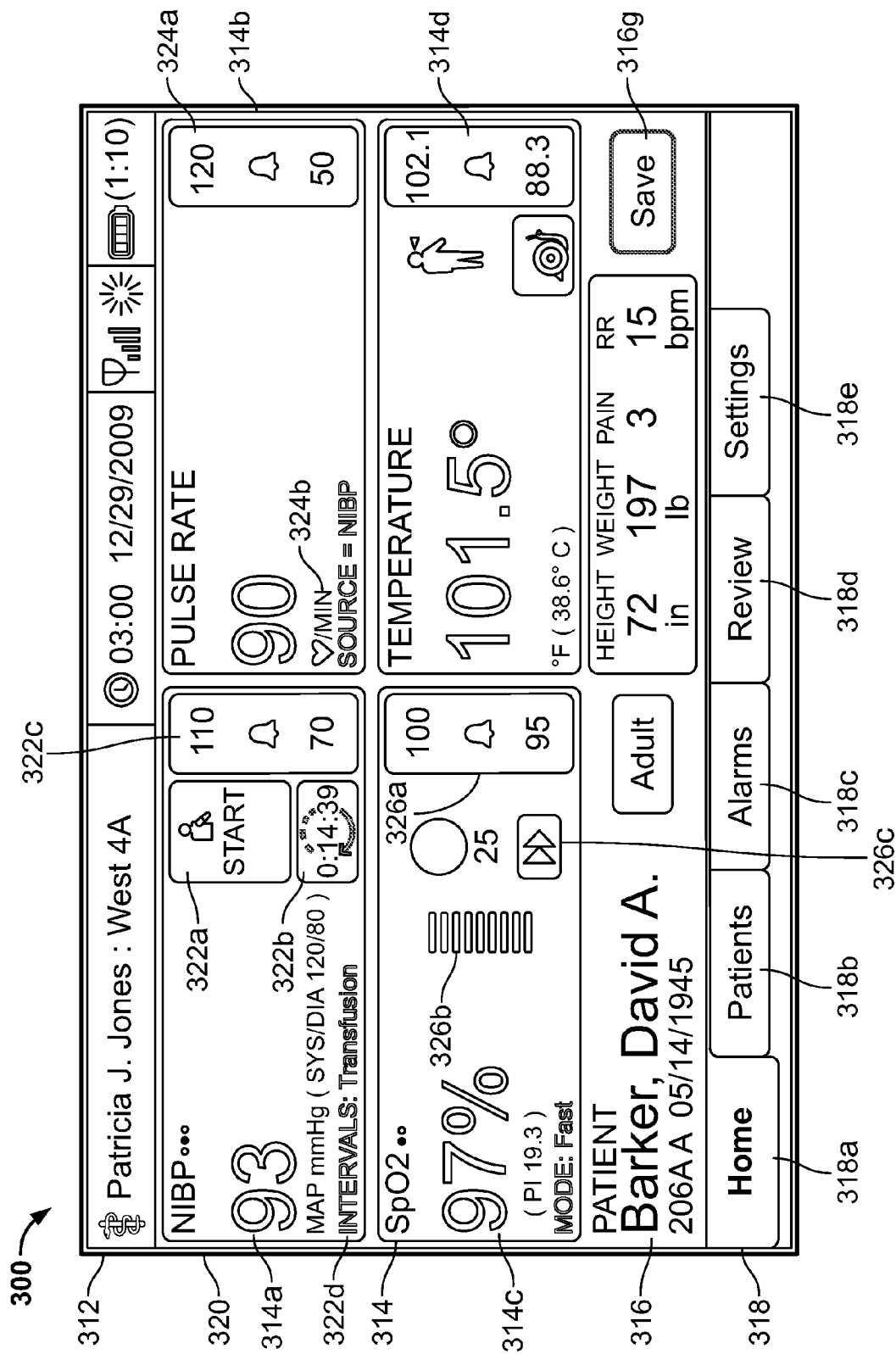
FIG. 3A illustrates an example monitoring workflow home screen.

FIG. 3A illustrates an example monitoring workflow home screen 300. The PMP device 200 displays the monitoring workflow home screen 300 while the PMP device 200 is operating within a monitoring workflow. The monitoring workflow is designed for obtaining a series of physiological measurements associated with an identified patient over a period of time.

The PMP device 200 is functionally connected to one or more sensors that enable monitoring of at least one physiological parameter that is associated with a patient. Typically, each sensor is physically attached to the patient while the PMP device 200 is operating within the monitoring workflow. These sensors include a temperature probe, a SpO2 clip, and a NIBP blood pressure cuff that are each attachable to the PMP device 200 as described above.

As shown in the example of FIG. 3A, the monitoring workflow home screen 300 includes a device status area 312, a navigation area 318, and a content area 320. The content area 320 is divided into a parameter reporting area 314 and a patient attribute area 316.

The device status area 312 contains data regarding a status of the PMP device 200. In the example of FIG. 3A, the device status area 312 includes text that identifies a clinician ("Patricia Jones") and a health care facility location ("West 4A"). A current time of day value ("03:00") is located towards the center of the device status area 312. A date value ("12/29/2009") is located to the right side of the time of day value. A remaining time of a battery ("1:10") value is located at the right side of the device status area 312.

The navigation area 318 includes a home tab 319a, a patients tab 319b, an alarms tab 319c, a review tab 319d, and a settings tab 319e. Collectively, the home tab 319a, the patients tab 319b, the alarms tab 319c, the review tab 319d, and the settings tab 319e are referred to herein collectively as the screen tabs 319. Selection of screen tabs 319b-319e causes substitution of the monitoring workflow home screen 300 with another screen associated with the screen tabs 319b-319e. For example, the PMP device 200 displays a patient screen when a user selects the patients tab 319b. FIG. 4A, discussed elsewhere in this document, illustrates an example patient selection screen. Furthermore, the PMP device 200 displays an alarms screen when a user selects the alarms tab 319c. FIGS. 7A-7E, discussed elsewhere in this document, illustrate an example alarms screen. Furthermore, the PMP device 200 displays a review screen when a user selects the review tab 319d. FIG. 5, discussed elsewhere in this document, illustrates an example review screen. Furthermore, the PMP device 200 displays a settings screen when a user selects the settings tab 319e. FIGS. 6A-6G, discussed elsewhere in this document, illustrate an example settings screen. When the PMP device 200 displays a screen other than the monitoring workflow home screen 300 and a user selects the home tab 319a, the PMP device 200 displays the monitoring workflow home screen 300.

The parameter reporting area 314 includes one or more parameter reporting frames. Each of the parameter reporting frames contains a representation of a different physiological parameter a patient. The representations are based on one or more measurements of the physiological parameters of a monitored patient. In addition, each of the parameter reporting frames contains an alarm reporting area. The alarm reporting areas specify upper alarm limits and lower alarm limits for the physiological parameters. The upper alarm limits and the lower alarm limits define the alarm ranges for the physiological parameters. Alarms associated with the physiological parameters are active when measurements of the physiological parameters are outside the alarm range for the physiological parameters.

In the example of FIG. 3A, the parameter reporting area 314 contains a NIBP frame 314a, a pulse rate frame 314b, a SpO2 frame 314c, and a temperature frame 314d. The NIBP frame 314a is located within an upper left portion of the parameter reporting area 314. The pulse rate frame 314b is located within an upper right portion of the parameter reporting area 314. The SpO2 frame 314c is located within a lower left portion of the parameter reporting area 314. The temperature frame 314d is located within a lower right portion of the parameter reporting area 314.

The NIBP frame 314a contains a representation of the blood pressure of the patient. The representation of the blood pressure of the patient is based on one or more measurements of the blood pressure of the patient. In various embodiments, the NIBP frame 314a contains various representations of the blood pressure of the patient. In the example of FIG. 3A, the NIBP frame 314a includes enlarged numerical text that represents a systolic blood pressure value ("120") and a diastolic blood pressure value ("80"), separated from each other via a slash '/' text character. The systolic blood pressure value is located at the left side of the NIBP frame 314a and the diastolic blood pressure is located to the right side of the systolic blood pressure value.

An NIBP alarm status area 322c is located at the right side of the NIBP frame 314a. The NIBP alarm status area 322c specifies an upper alarm limit and a lower alarm limit for the patient's systolic blood pressure and an upper alarm limit and a lower alarm limit for the patient's diastolic blood pressure. The upper alarm limit and the lower alarm limit for the patient's systolic blood pressure define a systolic blood pressure alarm range. The upper alarm limit and the lower alarm limit for the patient's diastolic blood pressure define a diastolic blood pressure alarm range. An alarm associated with the patient's blood pressure is active when the patient's systolic blood pressure is outside the systolic blood pressure alarm range or when the patient's diastolic blood pressure is outside the diastolic blood pressure alarm range The NIBP frame 314a also contains a NIBP cuff inflation stop button 322a. The NIBP cuff inflation stop button 322a is labeled with the text "Stop." The NIBP frame 314a also contains a NIBP automatic interval timer 322b. The NIBP automatic interval timer 322b is located between the diastolic blood pressure value and the NIBP alarm status area 322c. Selection of the NIBP cuff inflation stop button 322a ceases inflation of the NIBP cuff and toggles the label of the NIBP cuff inflation stop button 322a to display the ("Start") text. As used herein, a user selects a button or control when the user provides input to the PMP device 200 that specifies the control. For example, a user can select a control by pressing the control, by pressing another button while the control is highlighted, or by another means. Selection of the NIBP cuff inflation stop button 322a (now labeled the "Start" button) restarts inflation of the NIBP cuff and toggles the label of the NIBP cuff inflation stop button 322a to display the ("Stop") text. The NIBP automatic interval timer 322b indicates an amount of time remaining before the next scheduled inflation of the NIBP cuff. Additionally, a user can determine the age of the current NIBP reading on the NIBP frame 314a by subtracting the remaining time on the NIBP automatic interval timer 322b from the original interval duration. In the example of FIG. 3A, the NIBP frame 314a also displays a MAP value in an extended label field 322d.

The pulse rate frame 314b contains a representation of the patient's pulse rate. The representation of the patient's pulse rate is based on one or more measurements of the patient's pulse rate. In different embodiments, the pulse rate frame 314b contains different representations of the patient's pulse rate. In the example of FIG. 3A, the pulse rate frame 314b includes enlarged numerical text that represents a pulse rate value ("122"). The pulse rate value ("122") is located at the left side of the pulse rate frame 314b. A pulse rate alarm status area 324a is located at the right side of the pulse rate frame 314b. The pulse rate frame 314b also indicates a source of the pulse rate in an extended label field 324b.

The pulse rate alarm status area 324a specifies an upper alarm limit and a lower alarm limit. The upper alarm limit and the lower alarm limit define a pulse rate alarm range. An alarm associated with the patient's pulse rate is active when the patient's pulse rate is outside the pulse rate alarm range.

The SpO2 frame 314c contains a representation of the patient's SpO2 level. The representation of the patient's SpO2 level is based on one or more measurements of the patient's SpO2 level. In different embodiments, the SpO2 frame 314c contains different representations of the patient's SpO2 level. In the example of FIG. 3A, the SpO2 frame 314c includes enlarged numerical text that represents an SpO2 value ("97%"). The SpO2 value ("97%") is located at the left side of the SpO2 frame 314c and is accompanied by a '%' text character on the right side of the SpO2 value. A SpO2 alarm status area 326a is located at the right side of the SpO2 frame 314c. An SpO2 alarm parameter 326d, appearing as a circle adjacent to the text ("25"), indicates a duration of time. The SpO2 alarm status area 326a specifies an upper alarm limit and a lower alarm limit. The upper alarm limit and the lower alarm limit define a SpO2 alarm range. An alarm associated with the patient's SpO2 level is active when the patient's SpO2 level is outside the SpO2 alarm range for the duration of time indicated by the SpO2 alarm parameter 326d. The SpO2 frame 314c also includes a pulse amplitude blip bar 326b which indicates pulse beat and shows the relative pulse amplitude. As the detected pulse becomes stronger, more bars in the pulse amplitude blip bar 326b light up with each pulse. The SpO2 frame 314c also includes an SpO2 response time control button 326c that is configured for a user to control the SpO2 alarm parameter 326d.

The temperature frame 314d contains a representation of the patient's body temperature. The representation of the patient's body temperature is based on one or more measurements of the patient's body temperature. In different embodiments, the temperature frame 314d contains different representations of the patient's body temperature. In the example of FIG. 3A, the temperature frame 314d includes enlarged numerical text that represents a temperature value ("101.5"). The temperature value ("101.5") is located at the left side of the temperature frame 314d and is accompanied by a Fahrenheit degree indicating symbol on the right side of the temperature value. A temperature alarm status area 328a is located at the right side of the temperature frame 314d. The temperature alarm status area 328a specifies an upper alarm limit and a lower alarm limit. The upper alarm limit and the lower alarm limit define a temperature alarm range. An alarm associated with the patient's temperature is active when the patient's temperature level is outside the temperature alarm range.

In some embodiments, the PMP device 200 can measure the patient's temperature in either a predictive mode or in a direct mode. When the PMP device 200 measures the patient's temperature in the predictive mode, the PMP device 200 predicts the patient's current temperature based on periodic readings of the patient's temperature. When the PMP device 200 measures the patient's temperature in the direct mode, the PMP device 200 continually measures the patient's temperature.

The temperature value in the temperature frame 314d is based on measurements received from a thermometer attached to a patient. When the PMP device 200 measures the patient's temperature in the predictive mode, the thermometer can be located at various places on the patient's body. Example locations on the patient's body where the thermometer can be located include in the patient's mouth, on the patient's thigh, in the patient's armpit, in the patient's rectum, and other locations. The temperature frame 314d includes a thermometry location control 328b. The thermometry location control 328b indicates a location on the patient's body where the thermometer is located. In the example of FIG. 3A, the thermometry location control 328b indicates that the thermometer is located in the patient's mouth.

When a user selects the thermometry location control 328b, the PMP device 200 updates the thermometry location control 328b such that the thermometry location control 328b indicates a different location on the patient's body or whether the PMP device 200 is to obtain measurements of the patient's temperature in direct mode. The user can continue selecting the thermometry location control 328b until the thermometry location control 328b indicates a location where the thermometer is located on the patient's body or until the thermometry location control 328b indicates that measurements are to be obtained in direct mode. For example, in some embodiments, the PMP device 200 accepts readings from a thermometer when the thermometer is located in the patient's mouth, in an adult patient's armpit, or in a pediatric patient's armpit. In this example, the thermometry location control 328b initially indicates that the thermometer is in a patient's mouth. When the user selects the thermometry location control 328b one time, the thermometry location control 328b indicates that the thermometer is located in an adult patient's armpit. When the user selects the thermometry location control 328b again, the thermometry location control 328b indicates that the thermometer is located in a pediatric patient's armpit. When the user selects the thermometry location control 328b yet again, the thermometry location control 328b indicates that the measurements of the patient's temperature are to be obtained in direct mode. When the user selects the thermometry location control 328b yet again, the thermometry location control 328b again indicates that the thermometer is located in a patient's mouth.

Figure 3C:
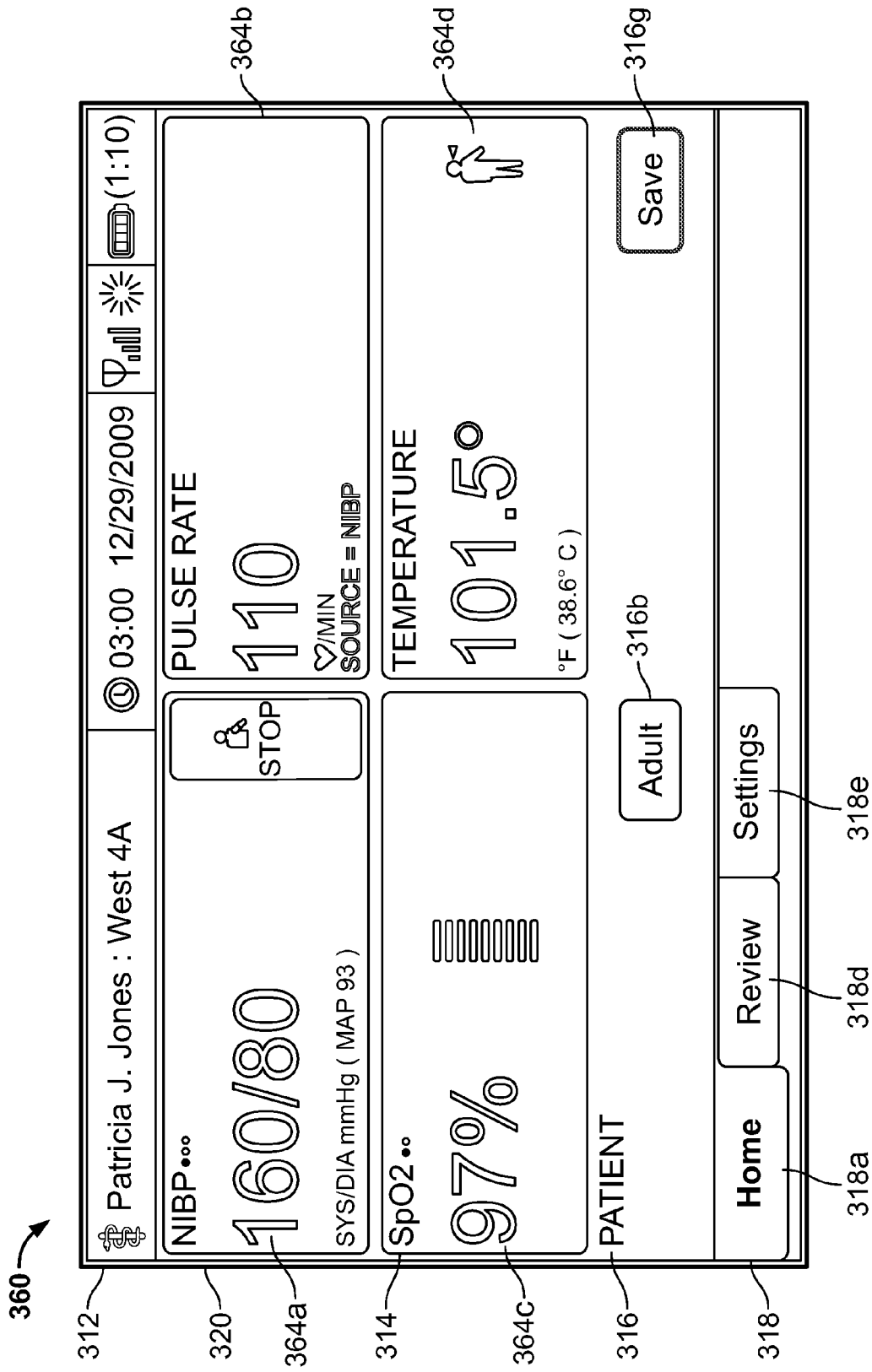
FIG. 3C illustrates an example triage workflow home screen.
Figure 3D:
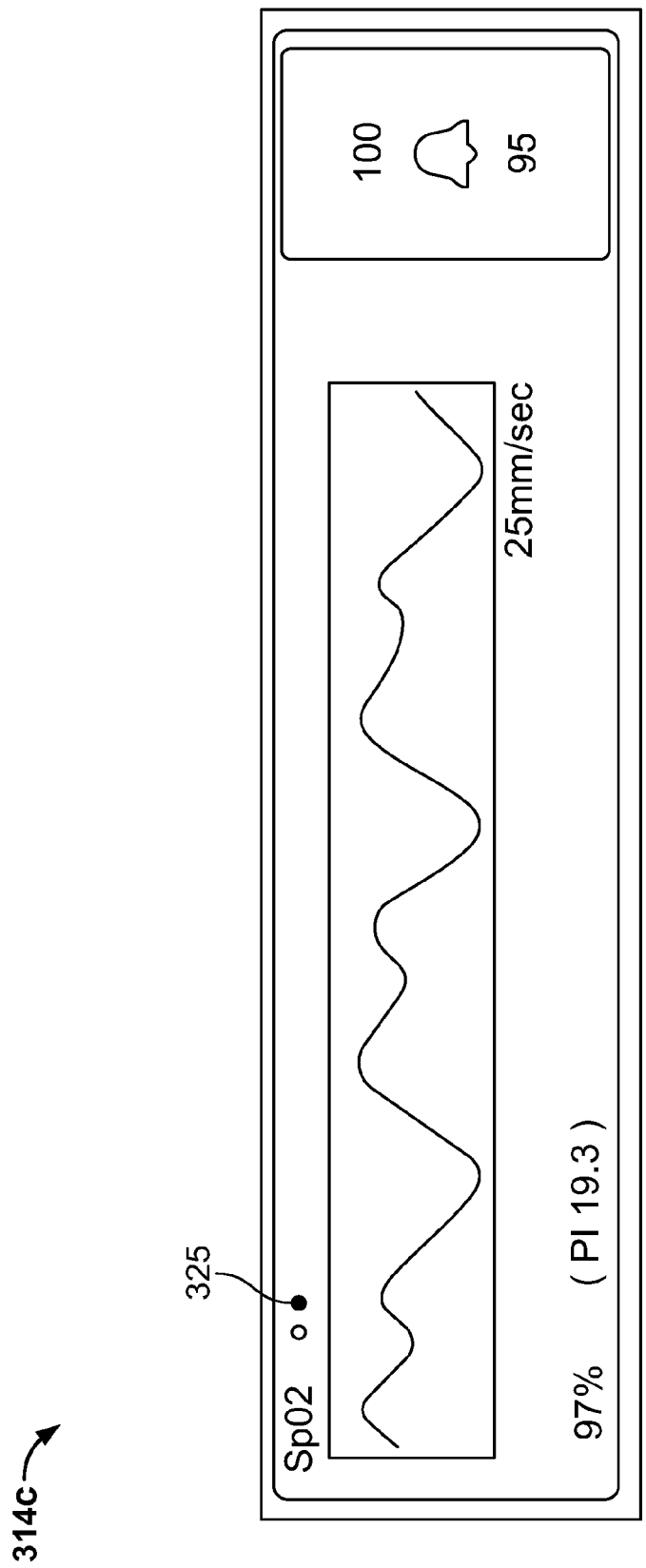
FIG. 3D illustrates an example alternative view of a patient's SpO2 level.

The display screen 218 enables a user to select the parameter reporting frames 314a-314d in order to change how the physiological parameters are represented in the parameter reporting frames 314a-314d. In other words, each of the parameter reporting frames 314a-314d contains an initial representation of a physiological parameter. The parameter reporting frame displays an alternate representation of the physiological parameter instead of the initial representation of the physiological parameter when a user selects the parameter reporting frame. For example, selecting the temperature frame 314*d* toggles the temperature value between being expressed in Fahrenheit or Centigrade. This feature is referred to as "tap to toggle." In another example, when a user selects the pulse rate frame 314*b*, the PMP device 200 displays a waveform in the pulse rate frame 314*b* instead of a number representing the patient's current pulse rate. The waveform represents a patient's pulse over time. In this example, when the user selects the pulse rate frame 314*b* again, the PMP device 200 displays a number in the pulse rate frame 314*b* representing the patient's current pulse rate. In yet another example, when the user selects the SpO2 frame 314*c*, the PMP device 200 displays a plethysmograhic waveform view in the SpO2 frame 314*c*. FIG. 3D illustrates an example alternate representation of a patient's SpO2 level. In the example of FIG. 3D, the SpO2 frame 314*c* contains a plethysmographic waveform view 325.

The patient attribute area 316 contains data that specify attributes of a patient. In various embodiments, the patient attribute area 316 contains data that specify various attributes of a patient. For example, in some embodiments, text that identifies a patient is located at the left side of the patient attribute area 316. In the example of FIG. 3A, the patient attribute area 316 contains the value "83645211" to identify the patient.

Furthermore, in the example of FIG. 3A, the patient attribute area 316 contains a patient type button 316*b* that is labeled with the text "Adult." The patient type button 316*b* is located towards the center of the patient attribute area 316. Patient-related attribute values that are labeled with the text ("HEIGHT"), ("WEIGHT"), ("PAIN") and ("RR") are located to the right side of the patient type button 316*b*. A save button 316*g* that is labeled with the text ("Save") is located at the right side of the patient attribute area 316.

The patient type button 316*b* indicates a value of a patient type parameter associated with the current patient. The patient type parameter can store a value of "Adult", "Pediatric", or "Neonatal" patient type. The patient type parameter controls the amount of air pressure applied to the NIBP cuff. Furthermore, in some embodiments, the patient type parameter controls the default alarm limits for the patient's physiological parameters. Thus, by using the patient type button 316*b* to change the patient type parameter, the user can automatically change the alarm limits for the patient's physiological parameters. As described elsewhere in this document, the user can also manually set the alarm limits for physiological parameters. When a user selects the patient type button 316*b*, the monitoring workflow home screen 300 is replaced by the patient selection screen as if the patients tab 319*b* was selected.

When the save button 316*g* is selected while the PMP device is operating in the monitoring workflow, the PMP device 200 saves a patient reading to local non-volatile storage within the PMP device 200. The patient reading is a set of data that includes measurements of the physiological parameters of the patient. If applicable, the patient reading can also include data indicating attributes of the patient. A user can use the review screen to review saved patient reading. Furthermore, in some embodiments, the PMP device 200 automatically attempts to transmit the patient reading to another computing node. A user can use the settings screen to specify the other computing node. In some embodiments, the other computing node is an electronic medical records system. Optionally, the other computing node is the interface system 104. The PMP device 200 does not clear the monitoring workflow home screen 300 when the save button 316*g* is selected.

The monitoring workflow is designed for obtaining a series of measurements of one or more physiological parameters of an identified patient over a period of time. A user uses the patient selection screen to select the identified patient. The PMP device 200 is programmable via an intervals pane of the settings screen to periodically record measurements of one or more physiological parameters over time from the identified patient.

A user may select the save button 316*g* one or more times. Each time the user selects the save button 316*g*, the PMP device 200 locally saves the patient reading and attempts to send the patient reading to another computing node. The sending is dependent on the workflow in which the PMP device 200 is operating. In the spot check workflow (see FIG. 3B), the PMP device 200 automatically sends the patient reading because a clinician is present when the measurements are obtained. When the PMP device 200 is operating in the monitoring workflow, a clinician may not be always present. Thus, the patient reading is not sent automatically. Instead, a clinician navigates to the review screen (See FIG. 5) and manually selects the patient reading that the user wants to send.

When the PMP device 200 is operating in the monitoring workflow, the representations of the physiological parameters and patient attributes remain displayed on the monitoring workflow home screen 300, regardless of whether or not the patient reading is saved locally and/or transmitted to another computing node in response to a selection of the save button 316*g*. Unlike the spot check and triage workflows, the PMP device 200 does not clear the monitoring workflow home screen 300 when a user selects the save button 316*g*.

In some embodiments, the home screens for each workflow supported by the PMP device 200 contain at least one common user interface element. The common user interface element has the same appearance in each of the home screens, but does not necessarily perform the same function in the home screens of the different workflows. In the example of FIG. 3A, the patient type button 316*b* and the save button 316*g* are user interface elements that are included within and common to the monitoring workflow home screen 300 and to home screens for the spot check workflow (FIG. 3B) and the triage workflow (FIG. 3C). Further, the patient type button 316*b* and the save button 316*g* have a same appearance but also have different functions depending upon which workflow the PMP device 200 is operating within.

When the PMP device 200 is operating in the monitoring workflow, the PMP device 200 clears the monitoring workflow home screen 300 upon discharge of the current (first) identified patient for which physiological parameters are being obtained. When the PMP device 200 clears the monitoring workflow home screen 300, the PMP device 200 modifies the monitoring workflow home screen 300 such that the monitoring workflow home screen 300 no longer contains data representing physiological parameters of a patient and attributes of the patient. The monitored patient is discharged by the selection of another (second) identified patient for which to obtain physiological data, via the patient selection screen 400 or by power-cycling the PMP device 200. Upon selection of the second patient, the PMP device 200 locally stores the patient reading for the first patient and transmits the patient reading for the first patient to another computing node when a user selects a send patient reading control 448*a* on the review screen (see FIG. 5). Upon attaching the sensors to the second identified patient, the PMP device 200 obtain measurements of a set of one or more physiological parameter from the second identified patient, periodically over time.

Unlike the home screens for non-monitoring workflows (e.g., the spot check workflow and the triage workflow), the monitoring workflow home screen 300 provides direct access to the alarm screen via the alarm status areas 322c, 324a, 326a, 328a located within the parameter reporting frames 314a-314d. Each alarm status area 322c, 324a, 326a, 328a (including the bell-shaped symbols) indicates high and low alarm limits and provides a visual indication of when an alarm is active.

Figure 3E:
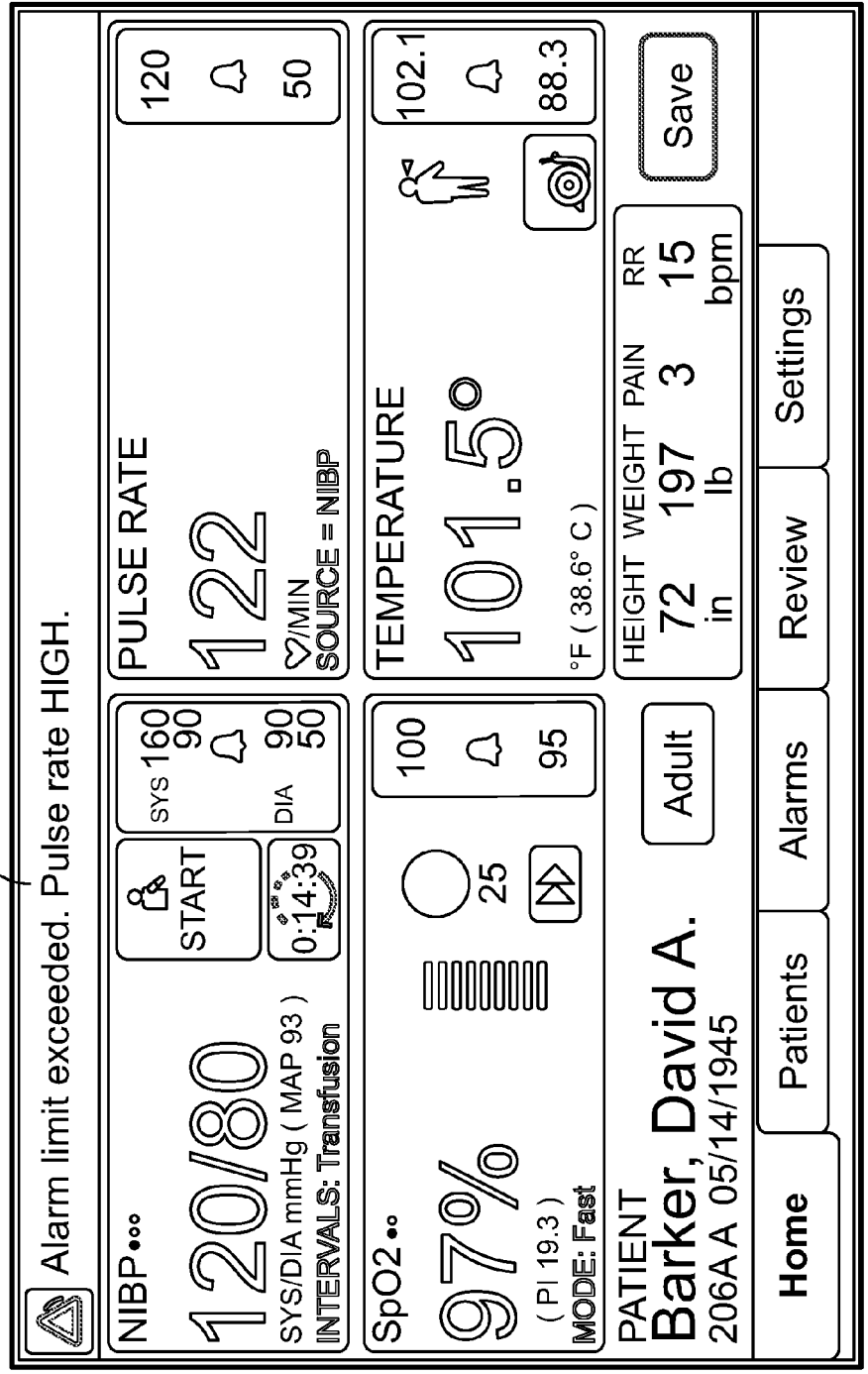
FIG. 3E illustrates the example monitoring workflow home screen when an alarm is active.

FIG. 3E illustrates the monitoring workflow home screen 300 when an alarm is active. When an alarm is active with respect to a particular physiological parameter, a perimeter around the parameter reporting frame for the particular physiological parameter transitions from a gray color to a red color. Changing the color of the perimeter provides a visual indication that the alarm is active. In some embodiments, the perimeter around the parameter reporting frame also flashes, thereby providing another visual indication that the alarm is active. Furthermore, the bell-shaped symbol within the alarm status area transitions from a white color to a red or yellow color, depending on a priority of the alarm. This provides another visual indication that the alarm is active. When the alarm is resolved, the bell-shaped symbol within the alarm status area transitions from the red or yellow color to the white color. In the example of FIG. 3E, an alarm associated with the patient's pulse rate is active. Accordingly, the perimeter around the pulse rate frame 314b is red instead of gray.

Furthermore, as illustrated in the example of FIG. 3E, when an alarm associated with a particular physiological parameter is active, the PMP device 200 causes the device status area 312 to display an alarm message 380. The alarm message 380 visually indicates that an alarm is active and indicates a brief description of the alert. In the example FIG. 3E, the alarm message 380 indicates that the reason for the alert is that the patient's heart rate is too high.

Furthermore, when an alarm associated with a particular physiological parameter is active, the PMP device 200 emits an alarm sound. The PMP device 200 continues to emit the alarm sound until the alarm is deactivated or until a user temporarily silences the alarm sound. When the user temporarily silences the alarm sound, the PMP device 200 suspends emitting the alarm sound for a given time period. In various embodiments, the user is able to temporarily silence the alarm sound in various ways. For example, in some embodiments, the user temporarily silences the alarm sound by touching the parameter reporting frame corresponding to the alarm. In other embodiments, the user temporarily silences the alarm sound by touching the alarm message 380. In yet other embodiments, the user temporarily silences the alarm sound by selecting a physical button on the PMP device 200.

When the user temporarily silences the alarm sound, the PMP device 200 resumes emitting the alarm sound after a given time period expires. For example, in some embodiments, the PMP device 200 resumes emitting the alarm sound after 30 seconds. When the user temporarily silences the alarm sound, the alarm message 380 indicates a time remaining before the PMP device 200 resumes emitting the alarm sound.

Figure 3F:
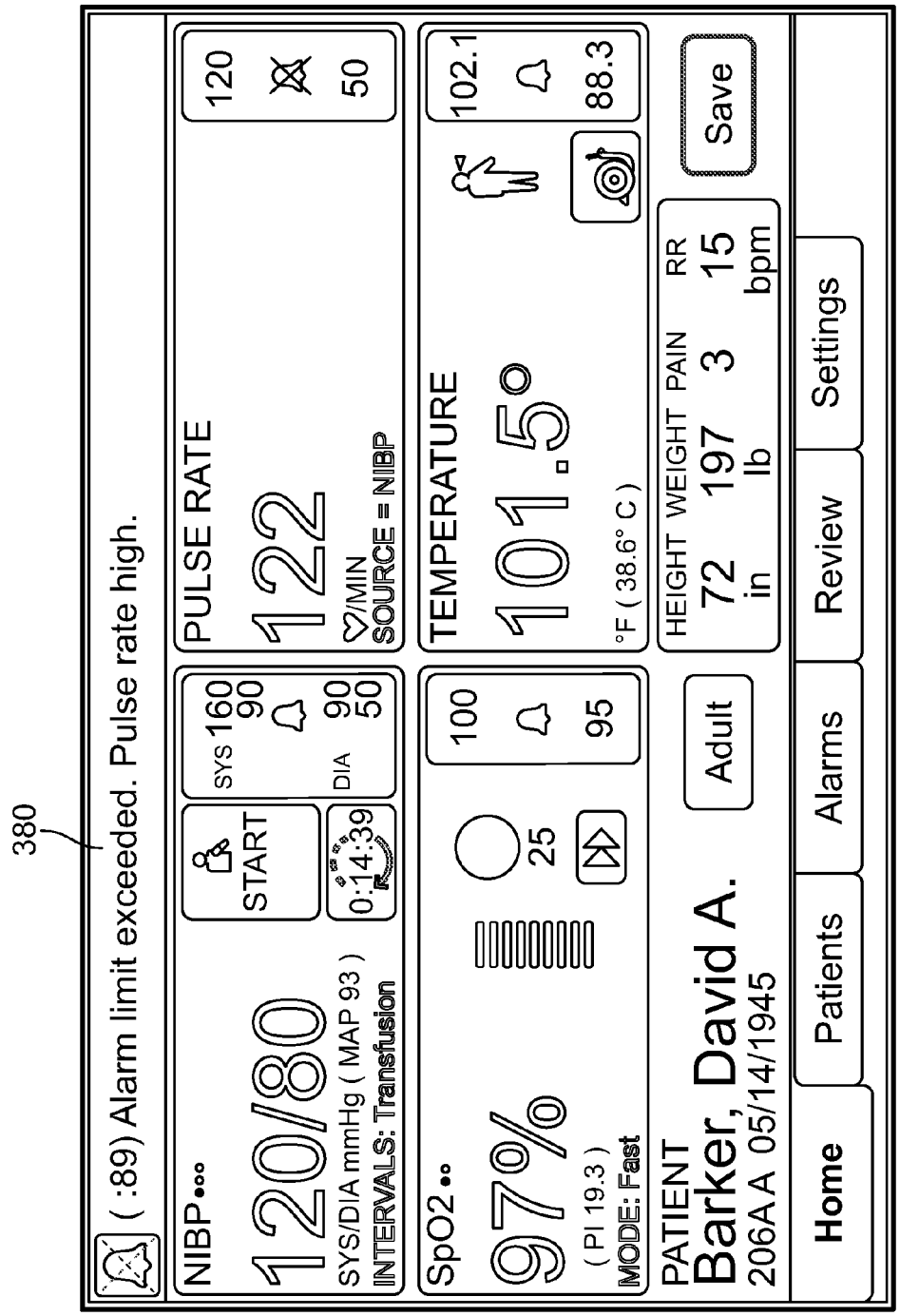
FIG. 3F illustrates the example monitoring workflow home screen when an alarm is active and when an alarm sound for the alarm has been temporarily silenced.

FIG. 3F illustrates the monitoring workflow home screen 300 when an alarm is active and when the alarm sound for the alarm has been temporarily silenced. In the example of FIG. 3F, the alarm message 380 indicates that eighty-nine seconds remain before the PMP device 200 resumes emitting the alarm sound.

In some embodiments, the user is able to temporarily silence the alarm sound for various lengths of time by selecting a button on the PMP device 200 or a control displayed by the PMP device 200 multiple times. For example, when the user selects the alarm message 380 one time, the PMP device 200 resumes emitting the alarm sound after sixty seconds. In this example, each time the user selects the alarm message 380, the PMP device 200 adds thirty seconds to the length of time before the PMP device 200 resumes emitting the alarm sound. In some embodiments, the PMP device 200 prevents the user from temporarily silencing the alarm sound for more than a given amount of time. For example, in some embodiments, the PMP device 200 prevents the user from temporarily silencing the alarm sound for more than five minutes.

When the user temporarily silences an alarm sound for an alarm, the monitoring workflow home screen 300 visually indicates that the alarm sound has been temporarily silenced. In various embodiments, the monitoring workflow home screen 300 visually indicates that the alarm sound has been temporarily silenced in various ways. For example, in some embodiments, the alarm message 380 contains a bell-shaped icon when the alarm sound has been temporarily silenced. In this example, the bell-shaped icon has an X-shaped mark over a bell. The lines of the X-shaped mark are dashed. In other example embodiments, the alarm message 380 or other parts of the monitoring workflow home screen 300 contain differently shaped icons or visual indicators.

Figure 7A:
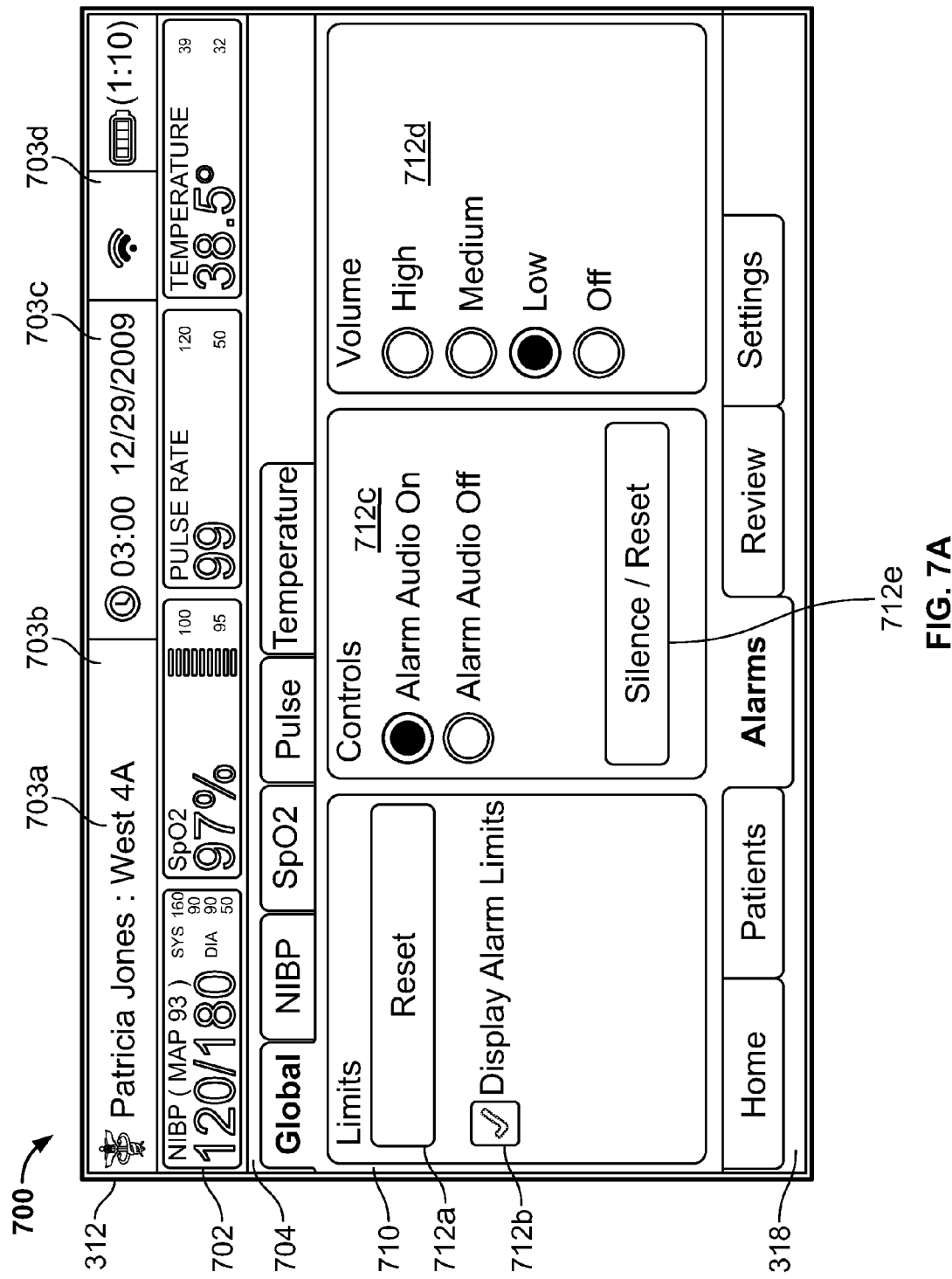
FIG. 7A illustrates an example global pane of an alarms screen.

The alarm status areas 322c, 324a, 326a, 328a act as navigational short cuts to appropriate panes within the alarms screen for each respective physiological parameter (See FIG. 7A). In this way, selecting an alarm status area while no alarm is active results in the PMP device 200 displaying the same user interface as if a user selects the alarms tab 319c and then selects an appropriate pane of the alarms screen. Navigation to the appropriate pane of the alarms screen happens only when the PMP device 200 is not emitting an alarm sound. In other words, the first selection of this area (or anywhere in the parameter reporting frame) would cause the alarm to silence the audio. A subsequent selection of the alarm status area performs the navigation.

Various alarms have various priority levels. For example, an alarm associated with a patient's pulse rate has a high priority level and an alarm associated with detachment of a SpO2 clip has a medium priority level. The PMP device 200 visually and/or sonically indicates alarms having different priority levels in different ways. For example, in some embodiments, when an alarm having a high priority level is active, the PMP device 200 displays visual indications of the alarm in a given color, such as red. When an alarm having a medium or low priority level is active, the PMP device 200 displays visual indications of the alarm in another color, such as yellow. Furthermore, in some embodiments, when an alarm having a high priority level is active, the PMP device 200 emits a given alarm sound, such as a continuous tone. When an alarm having a medium or low priority level is active, the PMP device 200 emits another alarm sound, such as a periodic beep.

When the PMP device 200 is operating in different workflows, the PMP device 200 can activate different alarms and/or emit different alarm sounds. For example, the PMP device 200 activates an alarm when a SpO2 clip detachment event occurs while the PMP device 200 operating within the monitoring workflow, but does not activate the alarm while in a non-operating in the monitoring workflow. This feature can be convenient considering that the PMP device 200 and the patient are more likely to be unattended by a user of the PMP device 200 for periods of time when the PMP device 200 is operating in the monitoring workflow, but less likely when the PMP device 200 is operating in the spot check or the triage workflows. In one embodiment, monitoring of SpO2 may be prevented by the PMP device 200 beyond ten minutes if the PMP device 200 is operating in the spot check or the triage workflows.

Under certain circumstances, multiple alarms can be active concurrently. For example, one alarm can be active because a patient's pulse rate is too high and another alarm can be active because a SpO2 clip has been detached from the patient. When multiple alarms are active concurrently, the PMP device 200 indicates that multiple alarms are active. In various embodiments, the PMP device 200 indicates that multiple alarms are active in various ways. For example, in some embodiments, the alarm message 380 includes an icon that indicates a number of alarms that are currently active. In this example, icon can be a triangle containing the number of alarms that are currently active.

In some embodiments, the PMP device 200 displays different visual indicators depending on the priority levels of concurrently active alarms. For example, when two or more high level alarms are active concurrently, the PMP device 200 displays visual indications for each of the high level alarms. In another example, when an alarm having a medium priority level ("the medium level alarm") and an alarm having a high priority level ("the high level alarm") are active concurrently, the PMP device 200 displays visual indications for the high level alarm and does not display visual indications for the medium level alarm. If the user of the PMP device 200 temporarily silences the alarm sound for the high level alarm, the PMP device 200 does not emit the alarm sound for the high level alarm or the alarm sound for the medium level alarm. When the high level alarm is resolved before the medium level alarm is resolved, the PMP device 200 displays visual indications for the medium level alarm and the PMP device 200 resumes emitting the alarm sound for the medium level alarm.

In some embodiments, the user of the PMP device 200 is able to toggle between multiple concurrently active alarms by selecting one or more controls in the user interface of the PMP device 200 or by selecting one or more buttons on the PMP device 200. In this way, the user causes the PMP device 200 to display the visual indications for each of the multiple concurrently active alarms. For example, a first alarm and a second alarm can be concurrently active. In this example, the PMP device 200 displays an alarm message describing a first alarm. In this example, the PMP device 200 modifies the alarm message to describe a second alarm when a user selects the alarm message.

In some embodiments, the PMP device 200 enables a user to customize the content within the monitoring workflow home screen 300. For example, the PMP device 200 enables a user to adjust the relative sizes of the parameter reporting frames 314a-314d within the monitoring workflow home screen 300. In another example, the PMP device 200 enables the user to add or remove parameter reporting frames from the monitoring workflow home screen 300. Furthermore, in some such embodiments, the PMP device 200 includes one or more predefined templates for the monitoring workflow home screen 300. Each of the predefined templates specifies a predefined set of content within the monitoring workflow home screen 300. For example, one predefined template specifies that the monitoring workflow home screen 300 includes a large parameter reporting frame for the patient's blood pressure and three smaller parameter reporting frames for the patient's pulse rate, SpO2 level, and body temperature. In this example, another predefined template specifies that the monitoring workflow home screen 300 includes only a frame for the patient's SpO2 level and the patient's blood pressure. The user can customize the content within the monitoring workflow home screen 300 by selecting one of these predefined templates or by modifying one of these predefined templates.

FIG. 3B illustrates an example spot check workflow home screen 330. The PMP device 200 displays the spot check workflow home screen 330 when the PMP device 200 is operating in a spot check workflow. The spot check workflow home screen 330 is referred to as the "Home" screen for the spot check workflow. Like when the PMP device 200 is operating in the monitoring workflow, each sensor is physically attached to an identified patient when the PMP device 200 is operating in the spot check workflow. These sensors include a temperature probe, a SpO2 clip, and a NIBP blood pressure cuff. As described elsewhere in this document, the temperature probe, the SpO2 clip and the NIBP blood pressure cuff are peripheral to the PMP device 200.

Also, like the monitoring workflow home screen 300 illustrated in the example of FIG. 3A, the spot check workflow home screen 330 includes a device status area 312, a content area 320, and a navigation area 318. The content area 320 includes a parameter reporting area 314 and a patient attribute area 316. The parameter reporting area 314 of the spot check workflow home screen 330 includes an NIBP frame 334a, a pulse rate frame 314b, a SpO2 frame 334c and a temperature frame 334d.

The NIBP frame 334a contains a representation of a patient's blood pressure. The representation is based on one or more measurements of the blood pressure of a previously identified patient. In the example of FIG. 3B, the NIBP frame 334a includes text representing the patient's systolic and diastolic blood pressure. In the spot check workflow home screen 330, the text representing the patient's systolic and diastolic blood pressure is larger than the text in the monitoring workflow home screen 300 representing the patient's systolic and diastolic blood pressure. The NIBP frame 334a of the spot check workflow home screen 330 does not include the NIBP alarm status area 322c and does not include the NIBP automatic interval timer 322b of the monitoring workflow home screen 300.

The pulse rate frame 334b contains a representation of the patient's pulse rate. The representation is based on one or more measurements of the pulse rate of the patient. In the example of FIG. 3B, the pulse rate frame 334b includes text representing the patient's pulse rate. In the spot check workflow home screen 330, the text representing the patient's pulse rate is larger than the text in the monitoring workflow home screen 300 representing the patient's pulse rate. The pulse rate frame 334b of the spot check workflow home screen 330 does not include the pulse rate alarm status area 324a included within the pulse rate frame 314b of the monitoring workflow home screen 300.

The SpO2 frame 334c contains a representation of the patient's SpO2 level. The representation is based on one or more measurements of the SpO2 level of the patient. In the example of FIG. 3B, the SpO2 frame 334c includes text representing the SpO2 value. In the spot check workflow home screen 330, the text representing the patient's SpO2 level is larger than the text in the monitoring workflow home screen 300 representing the patient's SpO2 level. The SpO2 frame 334c does not include the alarm status area 326a, the SpO2 response time control button 326c, or the SpO2 alarm parameter 326d of the SpO2 frame 314c of the monitoring workflow home screen 300.

The temperature frame 334d contains a representation of the patient's body temperature. The representation is based on one or more measurements of the body temperature of the patient. In the example of FIG. 3B, the temperature frame 334d includes text representing the patient's body temperature. In the spot check workflow home screen 330, the text representing the patient's body temperature is larger than the text in the monitoring workflow home screen 300 representing the patient's body temperature. The temperature frame 334d of the spot check workflow home screen 330 does not include the temperature alarm status area 328a included within the temperature frame 314d of the monitoring workflow home screen 300.

The patient attribute area 316 of the spot check workflow home screen 330 includes text that identifies the patient by name, initials, numerical identifier, or location. In the example of FIG. 3B, the patient attribute area 316 includes text that identifies the patient as "Bar, D." A user is able use the settings screen to configure the PMP device 200 to identify the patient by name or by number. The user is also able to use the settings screen to configure the PMP device 200 not to save or send patient readings when the PMP device 200 does not store information regarding the identity of the patient.

The navigation area 318 of the spot check workflow home screen 330 includes the home tab 319a, the patients tab 319b, the review tab 319d, and the settings tab 319e. The navigation area 318 excludes the alarms tab 319c included in the navigation area 318 of the monitoring workflow home screen 300. As a result, the spot check workflow home screen 330 does not provide direct navigation to the alarms screen as provided by the monitoring workflow home screen 300.

When the PMP device 200 is operating in the spot check workflow, the PMP device 200 locally saves a patient reading and attempts to send the patient reading to another computing node when a user selects the save button 316g. The patient reading includes measurements of the physiological parameters of the patient and data identifying the patient. Unlike when the PMP device 200 is operating in the monitoring workflow, the PMP device 200 clears the spot check workflow home screen 330 when the user selects the save button 316g. When the PMP device 200 clears the spot check workflow home screen 330, the PMP device 200 modifies the spot check workflow home screen 330 such that the spot check workflow home screen 330 no longer contains representations of the physiological parameters of the patient and attributes of the patient.

Because the PMP device 200 clears the spot check workflow home screen 330 when a user selects the save button 316g of the spot check workflow home screen 330, a first identified patient is essentially discharged when the user selects the save button 316g. After selecting the save button 316g, the user selects a second identified patient via the patient selection screen. Upon attaching the sensors to the second identified patient, the PMP device 200 obtains a set of one or more physiological parameter values from the second identified patient.

The spot check workflow is designed for obtaining measurements of physiological parameters from each patient in a series of identified patients. A user selects each patient in the series of identified patients from the patient selection screen. Alternatively, a user can select each patient in the series of identified patient by scanning barcodes of the patients, thereby bypassing the patient selection screen. Further, a user can identify a patient at any step in the workflow prior to saving the patient reading of the spot check workflow home screen 330. Upon attaching the sensors a patient in the series of identified patients, a user uses the PMP device 200 to obtain measurements of one or more physiological parameters of that patient. Typically, the PMP device 200 is attached to a first patient for no more time than is required to obtain one measurement for each of the NIBP, the pulse rate, the SpO2, and the body temperature of the first patient. The user then detaches the sensors from the first patient and attaches the sensors to a second patient that is next in the series of patients.

In one use scenario, a user can use the spot check workflow "making rounds" within a health care facility. For example, a clinician can use the PMP device 200 to obtain one set of measurements of physiological parameters for each patient in a group of twelve patients within a health care facility. Optionally, the clinician can transport the PMP device 200 sequentially to each patient in the group of patients within one "round" of obtaining measurements of physiological parameters. Each "round" of obtaining measurements of physiological parameters can be obtained for each patient in the patients of the group every hour during a working shift.

In some embodiments, the PMP device 200 enables a user to customize the content within the spot check workflow home screen 330. For example, the PMP device 200 enables a user to adjust the relative sizes of the parameter reporting frames 334a-334d within the spot check workflow home screen 330. In another example, the PMP device 200 enables the user to add or remove parameter reporting frames from the spot check workflow home screen 330. Furthermore, in some such embodiments, the PMP device 200 includes one or more predefined templates for the spot check workflow home screen 330. Each of the predefined templates specifies a predefined set of content within the spot check workflow home screen 330. The user can customize the content within the spot check workflow home screen 330 by selecting one of these predefined templates or by modifying one of these predefined templates.

FIG. 3C illustrates an example triage workflow home screen 360. The PMP device 200 displays the triage workflow home screen 360 when the PMP device 200 is in a triage workflow.

Like when the PMP device 200 is operating in the monitoring workflow or the spot check workflow, a user physically attaches each sensor to an unidentified patient when the PMP device 200 is operating in the triage workflow. These sensors include the temperature probe, the SpO2 clip, and the blood pressure cuff that are each attachable to the PMP device 200 as described elsewhere in this document.

The triage workflow home screen 360 includes a device status area 312, a content area 320, and a navigation area 318. The content area 320 of the triage workflow home screen 360 includes a parameter reporting area 314 and a patient attribute area 316. The parameter reporting area 314 of the triage workflow home screen 360 includes an NIBP frame 364a, a pulse rate frame 364b, a SpO2 frame 364c and a temperature frame 364d.

The NIBP frame 364a contains a representation of the systolic and diastolic blood pressure of the patient. The representation is based on one or more measurements of the blood pressure of the patient. In the example of FIG. 3C, the NIBP frame 364a includes text representing the systolic and diastolic blood pressure of the patient. The size of the text in the NIBP frame 364a is similar to the size of the text in the NIBP frame 334a of the spot check workflow home screen 330 and larger than the size of the text in the NIBP frame 314a of the monitoring workflow home screen 300. The NIBP frame 364a does not include the NIBP alarm status area 322c and does not include the NIBP automatic interval timer 322b included in the NIBP frame 314a of the monitoring workflow home screen 300.

The pulse rate frame 364b contains a representation of the pulse rate of the patient. The representation is based on one or more measurements of the pulse rate of the patient. In the example of FIG. 3C, the pulse rate frame 364b contains text representing the pulse rate value of the patient. The size of the text in the pulse rate frame 364b is similar to the size of the text in the pulse rate frame 334b of the spot check workflow home screen 330 and larger than the size of the text in the pulse rate frame 314b of the monitoring workflow home screen 300. The pulse rate frame 364b does not include the pulse rate alarm status area 324a that is included within the pulse rate frame 314b of the monitoring workflow home screen 300.

The SpO2 frame 364c contains a representation of the SpO2 level of the patient. The representation is based on one or more measurements of the SpO2 level of the patient. In the example of FIG. 3C, the SpO2 frame 364c includes text representing the SpO2 value of the patient. The size of the text in the SpO2 frame 364c is similar to the size of the text in the SpO2 frame 334c of the spot check workflow home screen 330 and larger than the size of the text in the SpO2 frame 314c of the monitoring workflow home screen 300. The SpO2 frame 334c does not include the alarm status area 326a, the SpO2 response time control button 326b, or the SpO2 alarm parameter 326b of the SpO2 frame 314c of the monitoring workflow home screen 300.

The temperature frame 364d contains a representation of the body temperature of the patient. The representation is based on one or more measurements of the body temperature of the patient. In the example of FIG. 3C, the temperature frame 364d includes text representing the body temperature of the patient. The size of the text in the temperature frame 364d is similar to the size of the text in the temperature frame 334d of the spot check workflow home screen 330 and larger than the size of the text in the temperature frame 314d of the temperature frame 314d of the monitoring workflow home screen 300. The temperature frame 364d does not include the temperature alarm status area 328a that is included within the temperature frame 314d of the monitoring workflow home screen 300.

The navigation area 318 of the triage workflow home screen 360 includes the home tab 319a, the review tab 319d, and the settings tab 319e. The navigation area 318 of the triage workflow home screen 360 excludes the alarms tab 319c of the monitoring workflow home screen 300. As a result, the triage workflow home screen 360 does not provide direct navigation to the alarms screen as provided by the monitoring workflow home screen 300. Furthermore, the navigation area 318 of the triage workflow home screen 360 excludes the patients tab 319b of the monitoring workflow home screen 300 and the spot check workflow home screen 330. As a result, the triage workflow home screen 360 does not provide direct navigation to the patient selection screen as provided by the monitoring workflow home screen 300 and the spot check workflow home screen 330.

The patient attribute area 316 of the triage workflow home screen 360 includes a patient type button 316b and a save button 316g. The patient attribute area 316 does not include text that identifies the patient.

When the PMP device 200 is operating within the triage workflow, the PMP device 200 locally saves a patient reading of the triage workflow home screen 360. The home screen data of the triage workflow home screen 360 includes measurements of the physiological parameters of the unidentified patient. Furthermore, a user can configure the PMP device 200 to transmit the patient reading of the triage workflow home screen 360 to another computing node in response to a selection of the save button 316g. Unlike the monitoring workflow home screen 300 and like the spot check workflow home screen 330, the PMP device 200 clears the triage workflow home screen 360 when a user selects the save button 316g. When the PMP device 200 clears the triage workflow home screen 360, the PMP device 200 modifies the triage workflow home screen 360 such that the triage workflow home screen 360 no longer contains representations of the physiological parameters of the patient.

When the PMP device 200 is operating in the triage workflow, selection of the patient type button 316b toggles the text label of the patient type button 316b and toggles a value of a patient type parameter within the triage workflow home screen 360. The text label and data value associated with the patient type button 316b, toggles between the label/values of ("Adult"), ("Pediatric") and ("Neonatal").

When the user selects the save button 316g, the patient reading transmitted to another computing node includes a patient type parameter value equal to ("Adult"), ("Pediatric") and ("Neonatal"). The patient type data substitutes for patient identification data that is absent from the patient reading while operating within the triage workflow.

As a result, when the PMP device 200 is operating in the triage workflow, a first unidentified patient is essentially discharged when a user selects the save button 316g. Upon attaching the sensors to a second unidentified patient, the user uses the PMP device 200 to obtain a set of one or more measurements of physiological parameter from the second unidentified patient.

The triage workflow is designed for obtaining measurements of physiological parameters from each of a series of unidentified patients. A user does not select each patient in the series of unidentified patients from the patient selection screen. Instead, the user attaches the sensors to each unidentified patient in sequence. Upon attaching the sensors to a patient in the series of the unidentified patients, the user uses the PMP device 200 to obtain measurements of one or more physiological parameters of that patient at that time. Typically, the user attaches the sensors to the patient for no more time that is required to obtain one measurement for each of the NIBP, the pulse rate, the SpO2 level, and the body temperature of the patient. The user then detaches the sensors are from the patient and attaches the sensors to another patient that is next in the series of patients.

In one use scenario, the triage workflow can be used for obtaining measurements of physiological parameters from unidentified health care recipients. The recipients may or may not be patients of a health care facility. The other computing node is a personal computer which receives the patient reading from the PMP device 200 with no patient names attached.

In some embodiments, the PMP device 200 enables a user to customize the content within the triage workflow home screen 360. For example, the PMP device 200 enables a user to adjust the relative sizes of the parameter reporting frames 364 within the triage workflow home screen 360. In another example, the PMP device 200 enables the user to add or remove parameter reporting frames from the triage workflow home screen 360. Furthermore, in some such embodiments, the PMP device 200 includes one or more predefined templates for the triage workflow home screen 360. Each of the predefined templates specifies a predefined set of content within the triage workflow home screen 360. The user can customize the content within the triage workflow home screen 360 by selecting one of these predefined templates or by modifying one of these predefined templates.

Figure 4:
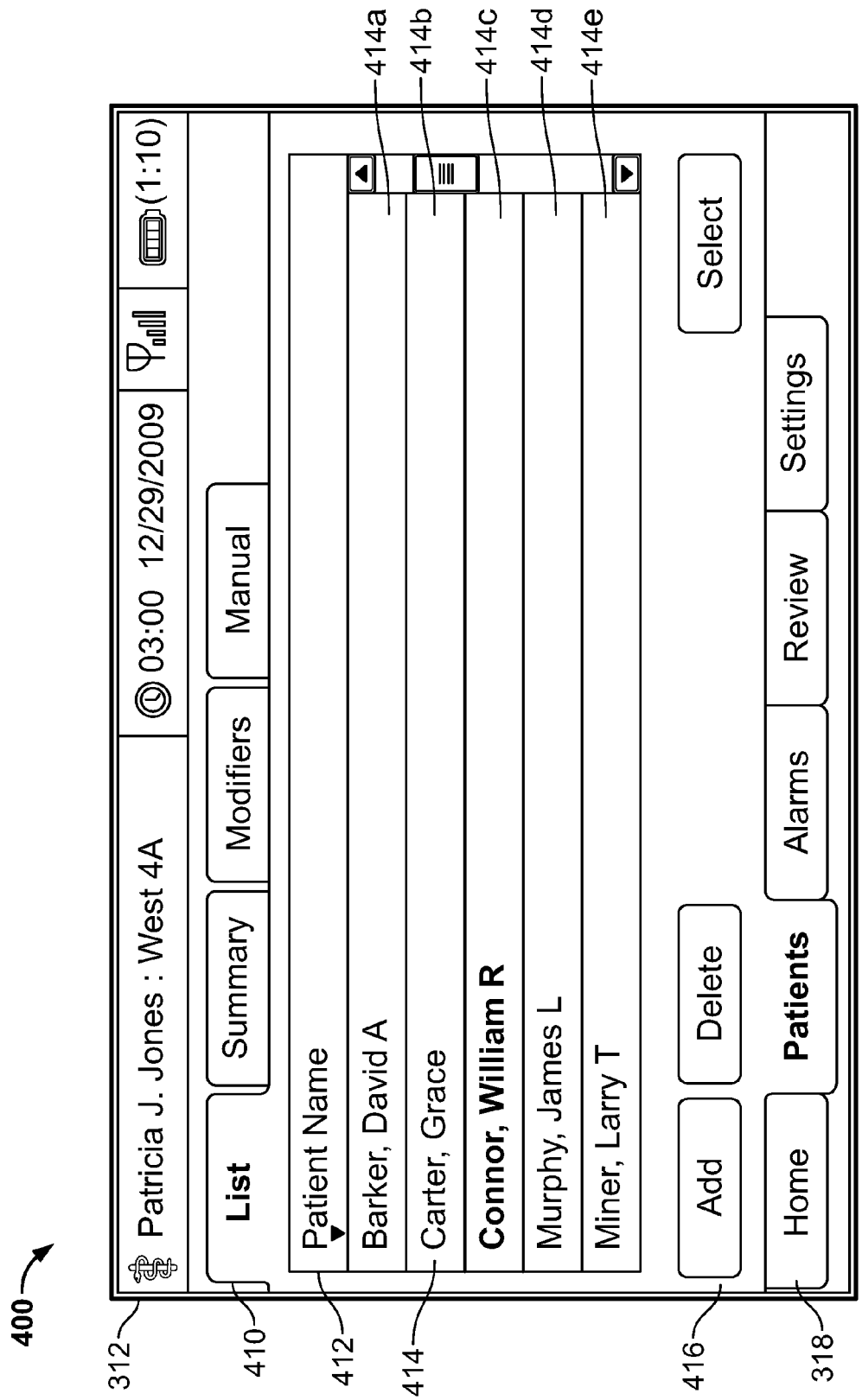
FIG. 4 illustrates an example patient selection screen.
Figure 5:
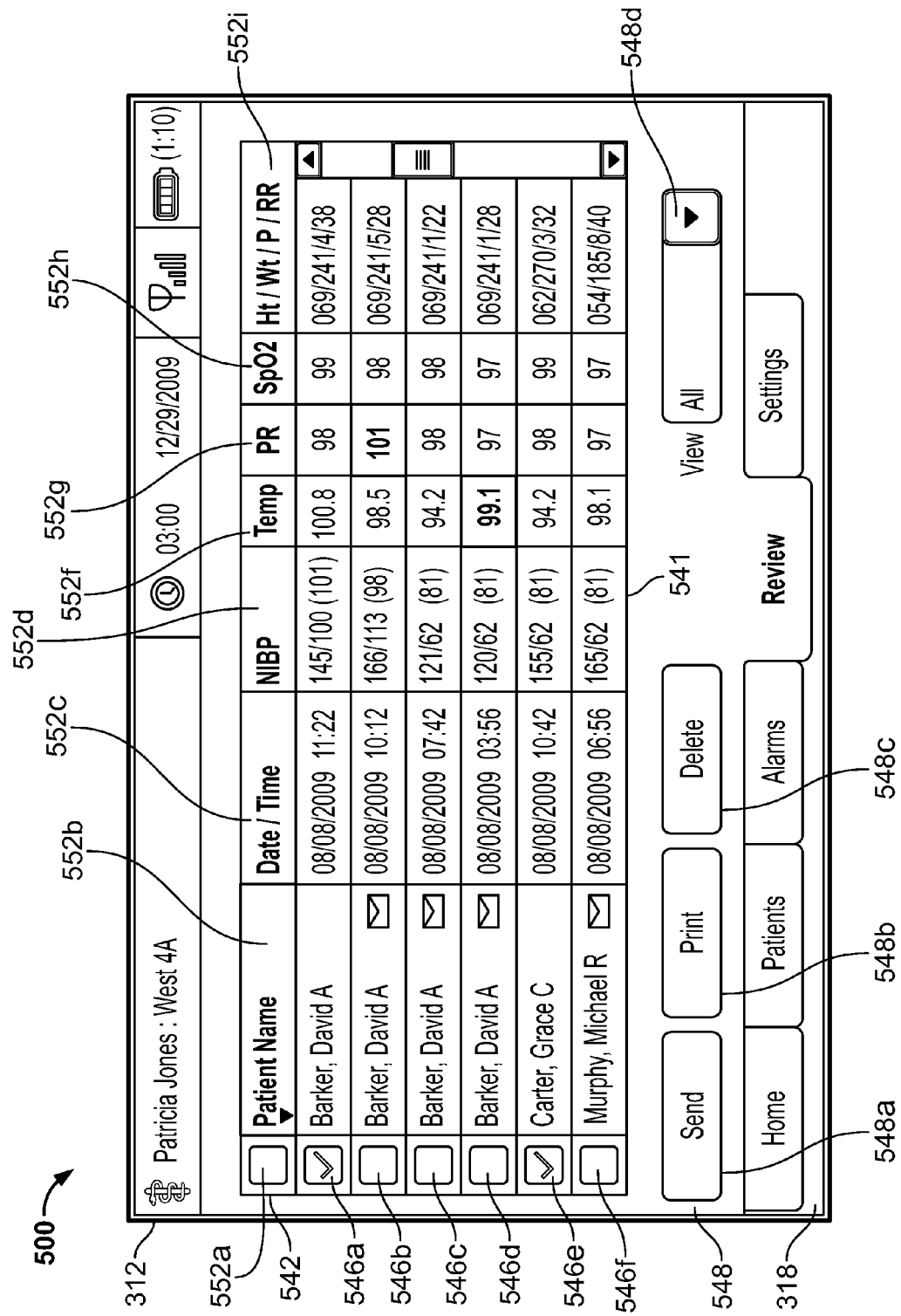
FIG. 5 illustrates an example review screen.

FIG. 4 illustrates an example patient selection screen 400. A user can navigate to the patient selection screen 400 by selecting the patients tab 319b. The patient selection screen 400 includes a device status area 312, a pane selection tab area 310 and a navigation area 318. The pane selection tab area 310 includes four pane selection tabs that are labeled "List", "Summary", "Modifiers" and "Manual." The list pane 418 includes a column label area 412, a patient listing area 414, and a screen control area 416. The device status area 312 appears like the device status area 312 of the monitoring workflow home screen 300, the device status area 312 of the spot check workflow home screen 330, and the device status area 312 of the triage workflow home screen 360. The navigation area 318 appears like the navigation area 318 of the monitoring workflow home screen 300.

The patient listing area 414 includes lines 415a-415e (collectively, "lines 415"). Each of the lines 415 is associated with a different patient. For example, a patient having a name "Barker, D." is listed on the line 415a, a patient having a name "Connor, W." is listed on the line 415c, and a patient having a name "Davison, A" is listed on the line 415e.

The screen control area 416 includes three buttons. A first (left) button that is labeled "Add" is utilized to add a patient to the patient listing area 414. A second (middle) button that is labeled "Delete" is utilized to delete a patient from the patient listing area 414. A third (right) button that is labeled "Select" is utilized to highlight a patient that listed within the patient listing area 414.

FIG. 5 illustrates an example review screen 500. A user can navigate to the review screen 500 using the review tab 319d. The review screen 500 includes a device status area 312, a review table 541, a screen control area 548, and a navigation area 318. The device status area 312 appears like the device status area 312 of the monitoring workflow home screen 300, the device status area 312 of the spot check workflow home screen 330, and the device status area 312 of the triage workflow home screen 360. The navigation area 318 of the review screen 500 appears like the navigation area 318 of the monitoring workflow home screen 300.

The review table 541 includes a column label line 542. In addition, the review table 541 includes patient readings 546a-546f and columns 552a-552i. Each of the patient readings 546a-546f comprises a different set of measurements of physiological parameters of a patient. Each of the columns 552b-552h is associated with a different physiological parameter. Check marks in the column 552a indicate whether particular ones of the patient readings 546a-546f are selected. In the example of FIG. 5, the patient readings 546A and 546e are selected.

For example, the patient reading 546a includes a patient name ("Barker, D.") in the column 552b, a date and time value in the column 552c, a systolic and diastolic measurement value in the column 552d, a mean arterial pressure (MAP) measurement value (not shown), a temperature measurement value in the column 552f, a pulse measurement value in the column 552g, an SpO2 measurement value in the column 552h, and a patient attributes set of values in the column 552i.

The screen control area 548 includes a send patient reading button 548a, a print patient reading button 548b, a delete patient reading button 548c and a view list box 548d. The print patient reading button 548b is utilized to send a selected patient reading. The print patient reading button 548b is utilized to print selected patient readings. The delete patient reading button 548c is utilized to delete selected patient readings. The view list box 548d enables filtering of the review table 541. A user can use the view list box 548d to select to view all available patient readings or only particular patient readings based on sent, unsent or alarm status.

Figure 6A:
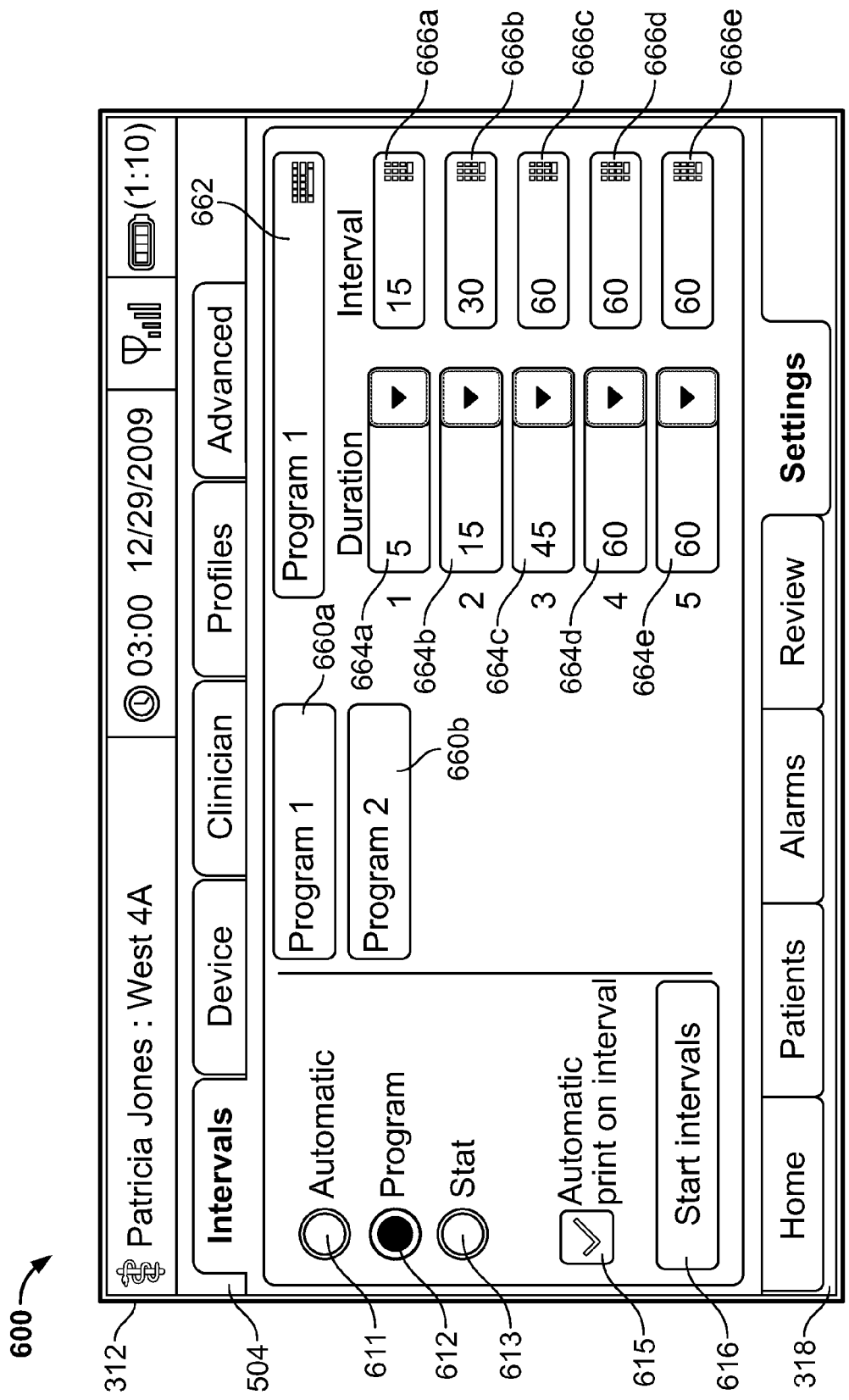
FIG. 6A illustrates an example intervals pane of a settings screen.

FIG. 6A illustrates an example intervals pane 610 of a settings screen 600. Direct navigation to the settings screen 600 is provided from the monitoring workflow home screen 300, from the spot check workflow home screen 330, and from the triage workflow home screen 360. For example, in some embodiments, a user of the PMP device 200 navigates to the settings screen 600 by selecting the settings tab 319e. As illustrated in the example of FIG. 6A, the settings screen 600 includes a device status area 312, a pane selection tab area 604, the intervals pane 610 and a navigation area 318.

The device status area 312 of the settings screen 600 appears like the device status area 312 of the monitoring workflow home screen 300, the device status area 312 of the spot check workflow home screen 330, and the device status area 312 of the triage workflow home screen 360. The pane selection tab area 604 includes five pane selection tabs that are labeled "Intervals," "Device," "Clinician," "Profiles," and "Advanced." The navigation area 318 of the settings screen 600 appears like the navigation area 318 of the monitoring workflow home screen 300.

A user can use the intervals pane 610 to program the PMP device 200 to save NIBP measurements, pulse rate measurements, SpO2 measurements, and temperature measurements for a patient at given intervals over an given time period. Other combinations of physiological parameters can be obtained at other fixed or non-fixed intervals.

The intervals pane 610 includes an automatic control 611, a program control 612, a stat control 613, an off control (not shown), a print control 615, and a start control 616. When the automatic control 611 is selected, the settings screen 600 contains one or more controls for entering a fixed time period to right of control. When the program control 612 is selected, the settings screen 600 contains controls for defining and selecting interval programs. When the stat control 613 is selected, the settings screen 600 contains one or more controls for capturing and saving as many measurements of physiological parameters as possible within a time period, for example a five minute period. When the off control is selected, intervals are turned off. When the print control 615 is selected, a captured measurement at each interval may be printed. The start control 616 is a command button to start the selected interval workflow: Automatic, Program, or Stat. The PMP device 200 automatically initiates an NIBP reading and initiates the interval program once the start control 616 is selected.

In the example of FIG. 6A, the program control 612 is selected. Consequently, the intervals pane 610 includes controls for defining and selecting interval programs. An interval program is a set of parameters that governs the intervals at which the PMP device 200 records measurements of one or more physiological parameters of a patient and for lengths of time for which the PMP device 200 records the measurements of the one or more physiological parameters of the patient.

In the example of FIG. 6A, the intervals pane 610 contains interval program selection controls 660*a*, 660*b* (collectively, interval program selection controls 660). More or fewer controls 660 can be provided. The interval program selection controls 660 specify the names of interval programs. In some examples, the interval program selection controls 660 specify names associated with the controls, such as "Transplant," "Transfusion," "Cardiac," which represent names of interval programs.

A user selects an interval program by selecting one of the interval program selection controls 660 that corresponds to the interval program. After selecting the interval program, the user starts the interval program by selecting the start control 616. When the user starts the interval program, the PMP device 200 records measurements of physiological parameters of a patient at the intervals specified by the interval program for the duration specified by the interval program.

In some embodiments, the monitoring workflow home screen 300 contains remaining time controls. The remaining time controls indicate amounts of time remaining before the PMP device 200 records measurements of the physiological parameters. For example, the pulse rate frame 314*b* of the monitoring workflow home screen 300 can include a remaining time control that indicates that twenty seconds remain before the PMP device 200 records a measurement of the patient's pulse rate. Furthermore, in some embodiments, the PMP device 200 displays the intervals pane 610 when the user selects the remaining time controls. In this way, the user of the PMP device 200 can easily access the intervals pane 610.

Furthermore, in the example of FIG. 6A, the intervals pane 610 contains a program name control 662, duration controls 664*a*-664*e* (collectively, "duration controls 664"), and interval controls 666*a*-666*e* (collectively, "interval controls 666"). The duration controls 664 and the interval controls 666 are organized into rows. Each row corresponds to a different physiological parameter of the patient. For example, a first row corresponds to the patient's blood pressure, a second row corresponds to the patient's pulse rate, and so on.

When the user selects an interval program using one of the interval program selection controls 660, the program name control 662 contains the name of the interval program. In the example of FIG. 6A, the program name control 662 indicates that the name of the interval program is "Transfusion." The duration controls 664 specify lengths of time during which the PMP device 200 is to record measurements of the physiological parameters. The interval controls 666 specify lengths of time that the PMP device 200 waits between recording measurements of the physiological parameters. In the example of FIG. 6A, the duration control 664*a* indicates 1 hour and the interval control 666*a* indicates 15 minutes. Consequently, the PMP device 200 records measurements of a physiological parameter at 15 minute intervals for one hour after the "Transfusion" interval program starts.

When the user selects an interval program using one of the interval program selection controls 660, the user is able to change the values in the program name control 662, the duration controls 664, and the interval controls 666. For example, the user can change the value of the duration control 664*b* from one hour to two hours.

Figure 6B:
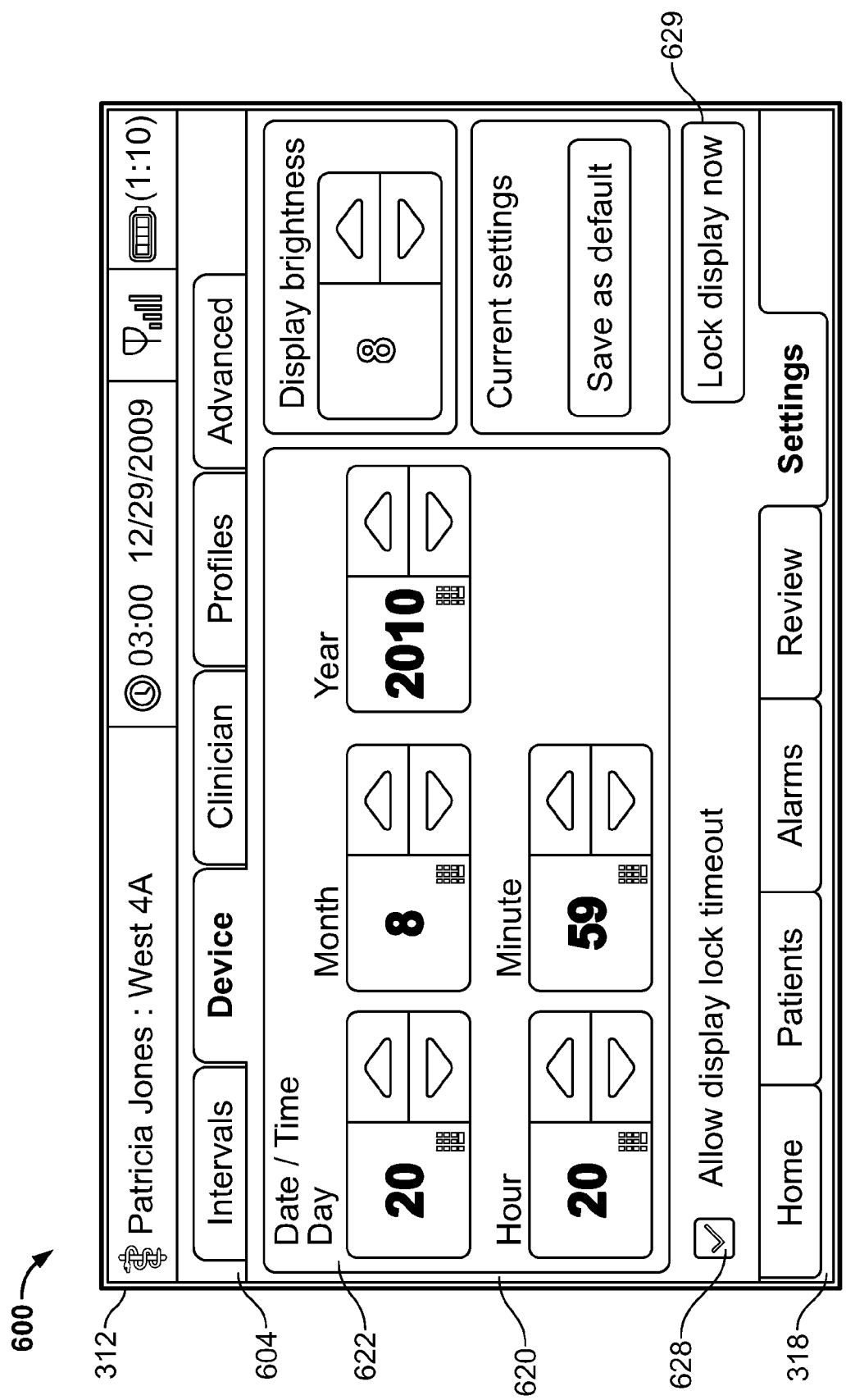
FIG. 6B illustrates an example device pane of the settings screen.

FIG. 6B illustrates an example device pane 620 of the settings screen 600. The settings screen 600 includes a device status area 312, a pane selection tab area 604, a device pane 520 and a navigation area 318. The device status area 312, the pane selection tab area 604, and the navigation area 318 appear like that of FIG. 6A.

The device pane 620 provides controls and information for a user to select or view device characteristics. The device pane 620 includes a set date and time control 622, a touch-screen lock-out control 628, and a command button 629. The set date and time control 622 is configured to set up a date and time for the PMP device 200. A user may select a date display format through the date format selection (not shown), such as MM/DD/YYYY. A user may also select a time zone offset from UTC based on where the PMP device 200 is located. The touch-screen lock-out control 628 is configured to allow a user to lock out the touch screen. When the command button 629 is selected, the touch screen is locked out immediately.

Figure 6C:
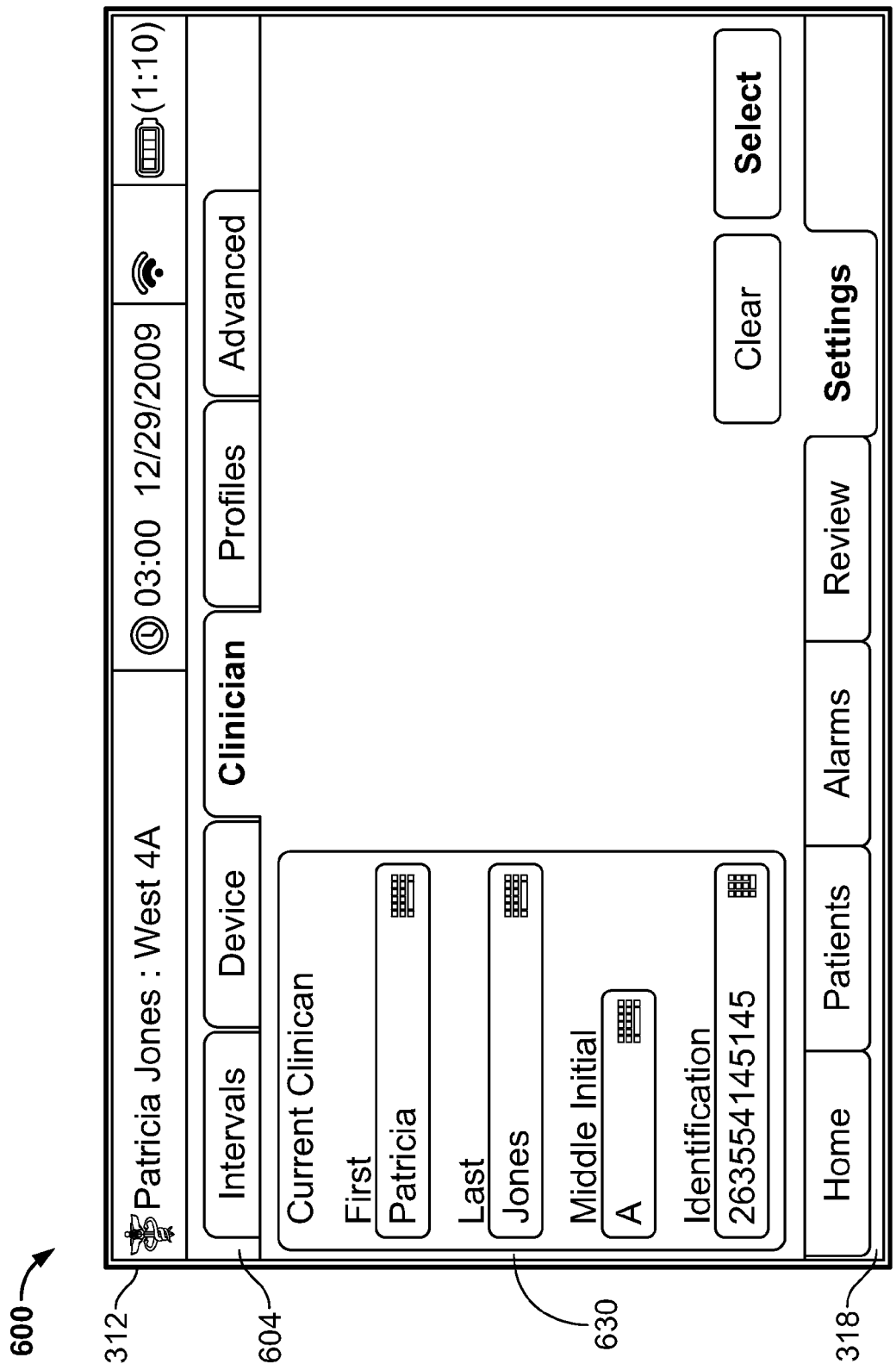
FIG. 6C illustrates an example clinician pane of the settings screen.

FIG. 6C illustrates an example clinician pane of the settings screen 600. The settings screen 600 includes a device status area 312, a pane selection tab area 604, a clinician pane 630 and a navigation area 318. The device status area 312, the pane selection tab area 604 and the navigation area 318 appear like that of FIG. 6A. The clinician pane 630 provides for entry of clinician identification. The clinician identified can include a first name, a last name, a middle initial, and an identification number.

Figure 6D:
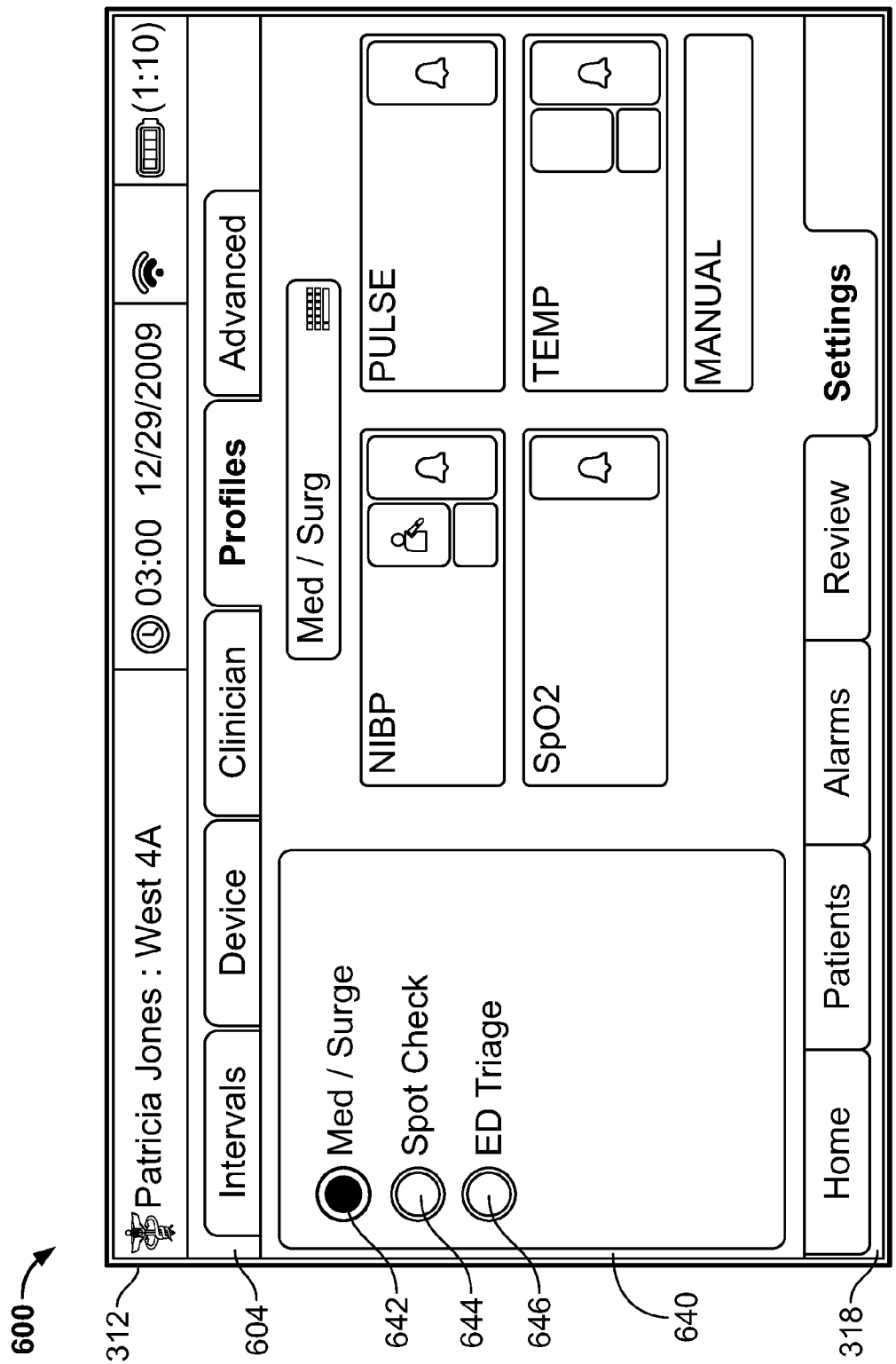
FIGS. 6D-6F illustrate example profile panes of the settings screen.
Figure 6E:
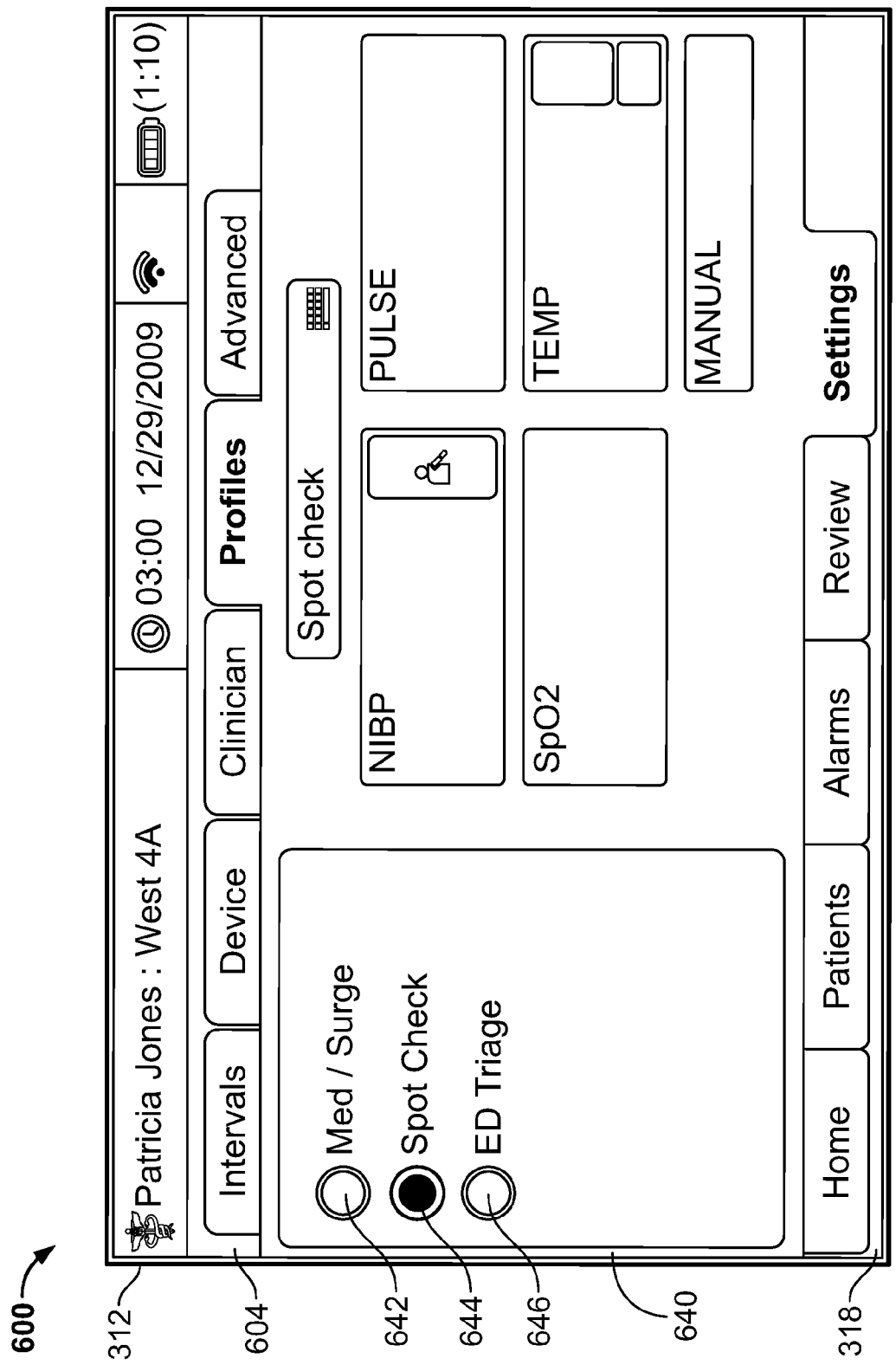
Figure 6F:
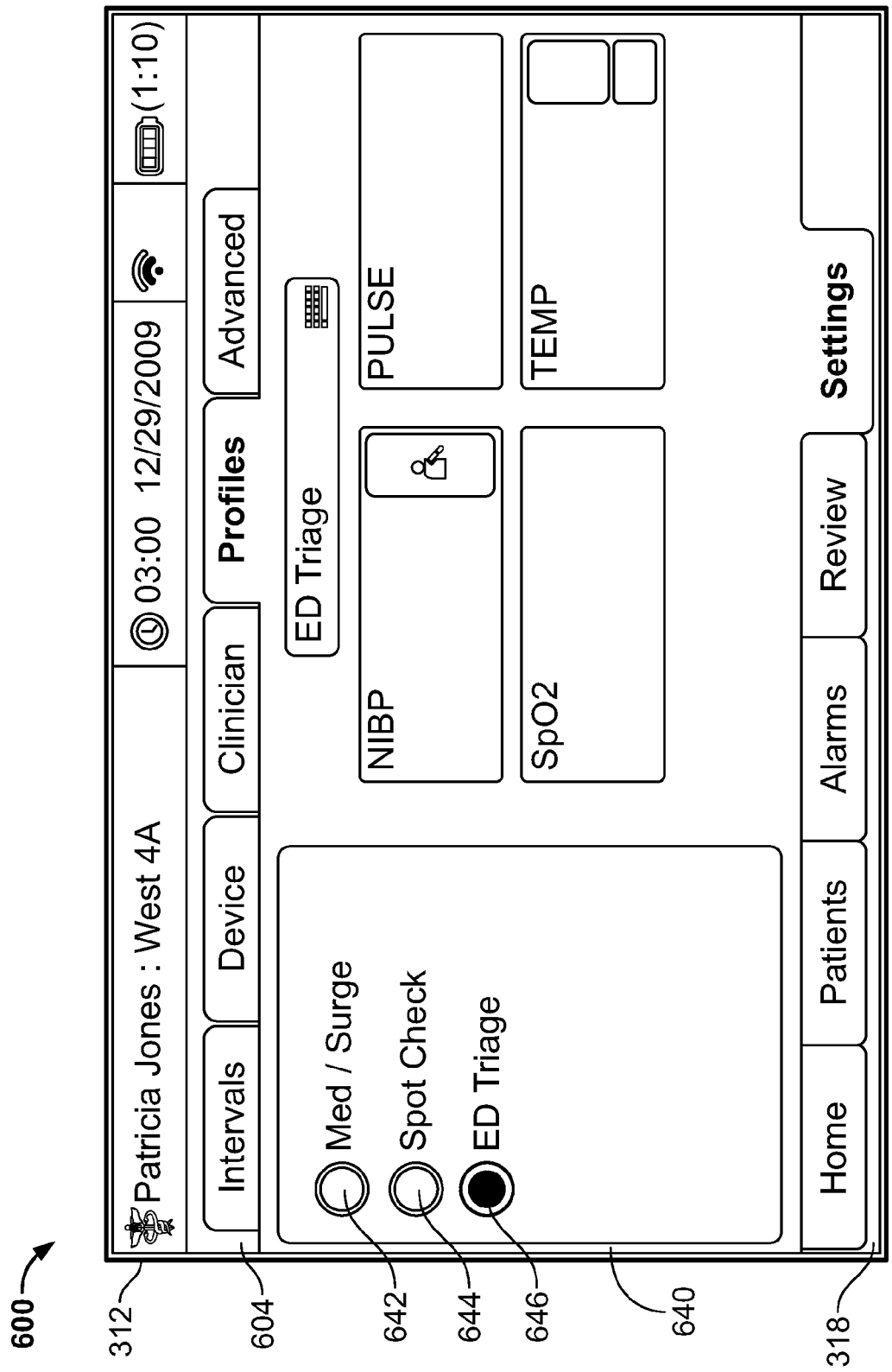

FIGS. 6D-6F illustrate an example profiles pane 640 of the settings screen 600. The settings screen 600 includes the device status area 312, a pane selection tab area 604, the profiles pane 640 and a navigation area 318. The device status area 312, the pane selection tab area 604 and the navigation area 318 appear like that of FIG. 6A. The profiles pane 640 allows a user to select a desired workflow within which the PMP device 200 is to operate. In the examples of FIG. 6D-6F, the profiles pane 640 includes a "Med/Surge" control 642, a "Spot Check" control 644, and an "ED Triage" control 646. A user selects the "Med/Surge" control 642 to select a "Med/Surge" workflow as the workflow in which the PMP device 200 is to operate. The user selects the "Spot Check" control 644 to select the spot check workflow as the workflow in which the PMP device 200 is to operate. The user selects the "ED triage" control 646 to select the triage workflow as the workflow in which the PMP device 200 is to operate. As shown in the examples of FIGS. 6D-6F, the profiles pane 640 shows a preview of the home screen of the selected workflow.

Figure 6G:
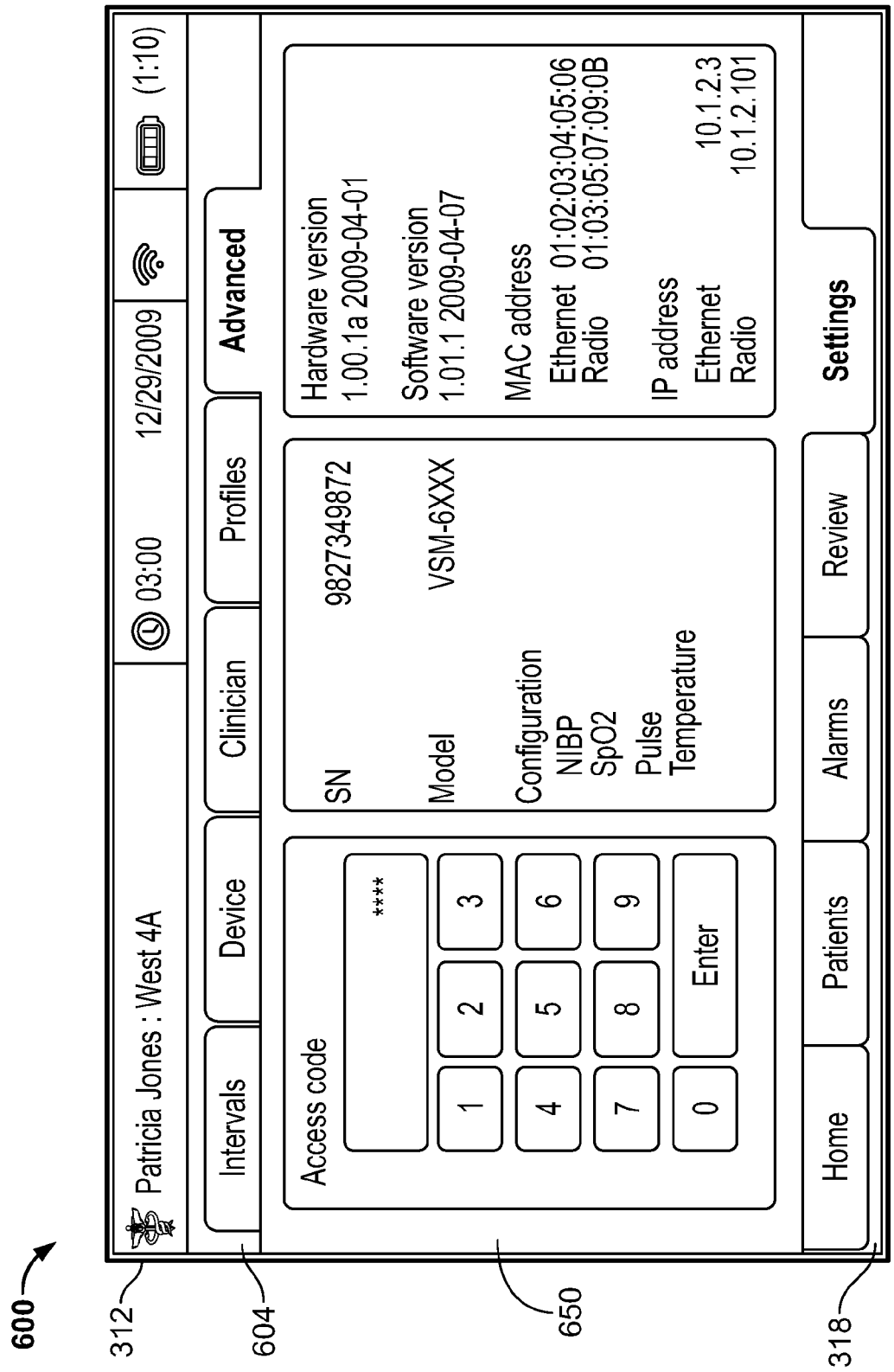
FIG. 6G illustrates an example advanced pane of the settings screen.

FIG. 6G illustrates an example advanced pane 650 of the settings screen 600. The settings screen 600 includes a device status area 312, a pane selection tab area 604, the advanced pane 650 and a navigation area 318. The device status area 312, the pane selection tab area 504 and the navigation area 318 appear like that of FIG. 6A. The advanced pane 650 enables an administrator to access configuration settings that are likely to be set once or less frequently than those required for a normal use. When a proper access code is entered, the PMP device 200 switches to an administration workflow and the navigation tabs switch to advanced settings tabs. The advanced pane 650 also provides read-only information about the PMP device 200.

FIG. 7A illustrates an example global pane 710 of an alarms screen 700. A user of the PMP device 200 navigates to the alarms screen 700 by selecting the alarms tab 319*c*. The alarms screen 700 includes controls that enable a user to configure global alarm settings and parameter-specific alarm settings.

As illustrated in the example of FIG. 7A, the alarms screen 700 includes the device status area 312, a compressed parameter reporting area 702, a pane selection tab area 704, the global pane 710, and the navigation area 318. The device status area 312 appears like the device status areas of the monitoring workflow home screen 300, the spot check workflow home screen 330 and the triage workflow home screen 360. The navigation area 318 of the alarms screen 700 appears like the navigation area 318 of the monitoring workflow home screen 300.

The compressed parameter reporting area 702 contains one or more compressed parameter frames containing data representing live physiological parameters of a patient. In the example of FIG. 7A, the compressed parameter reporting area 702 contains a compressed NIBP frame 703a, a compressed SpO2 frame 703b, a compressed pulse rate frame 703c, and a compressed temperature frame 703d. The compressed NIBP frame 703a, the compressed SpO2 frame 703b, the compressed pulse rate frame 703c, and the compressed temperature frame 703d are referred to herein collectively as the compressed frames 703. The compressed parameter reporting area 702 has frame dimensions that are smaller than the frame dimensions of the parameter reporting area 314 of the monitoring workflow home screen 300. Because the compressed parameter reporting area 702 is smaller than the parameter reporting area 314, the compressed parameter reporting area 702 appears "squished" relative to the parameter reporting area 314.

The compressed NIBP frame 703a contains a representation of the systolic and the diastolic blood pressure of the patient. The compressed SpO2 frame 703b contains a representation of a SpO2 percentage of the patient, a pulse amplitude blip bar, and alarm limits for the SpO2 parameter. The compressed pulse rate frame 703c contains a representation of a pulse rate of the patient. The compressed temperature frame 703d contains a representation of the body temperature of the patient. In the example of FIG. 7A, the compressed frames 703 do not contain user-selectable controls. Consequently, the user is unable to toggle views of the physiological parameters from the compressed frames 703.

When an alarm associated with one of the physiological parameters is active, the corresponding one of the compressed frames 703 provides a visual indication of the alarm. For example, when the patient's blood pressure is too high, a perimeter of the compressed NIBP frame 703a changes from one color (e.g., gray) to a different color (e.g., red). Furthermore, when an alarm is active, the device status area 312 of the alarms screen 700 is replaced by an alarm message describing the alarm. In some embodiments, selecting the alarm message causes the PMP device 200 to temporarily stop emitting an alarm sound associated with the alarm.

The pane selection tab area 704 includes five pane selection tabs that are labeled "Global", "NIBP", "SpO2", "Pulse" and "Temperature." When the user selects one of the pane selection tabs in the pane selection tab area 704, the PMP device 200 updates the alarms screen 700 to contain a pane associated with the selected pane selection tab.

The global pane 710 is located below the compressed parameter reporting area 702. The global pane 710 provides controls for configuring global alarm settings for the PMP device 200. The global alarm settings are settings that apply to all alarms provided by the PMP device 200. In the example of FIG. 7A, the global pane 710 includes a reset button 712a, a display alarm limit parameter button 712b, a set of alarm audio buttons 712c, a set of volume buttons 712d, and a silence/reset button 712e. A user can use the reset button 712a to reset alarm limits. The user can use the display alarm limit parameter button 712b to configure the PMP device 200 to display or not to display alarm limits. The user can use the set of alarm audio buttons 712c to configure the PMP device 200 to emit alarm sounds. The user can use the set of volume buttons 712d to set a volume of the alarm sounds to high, medium or low. Also, the user can use the silence/reset button 712e to silence or reset alarms.

Figure 7B:
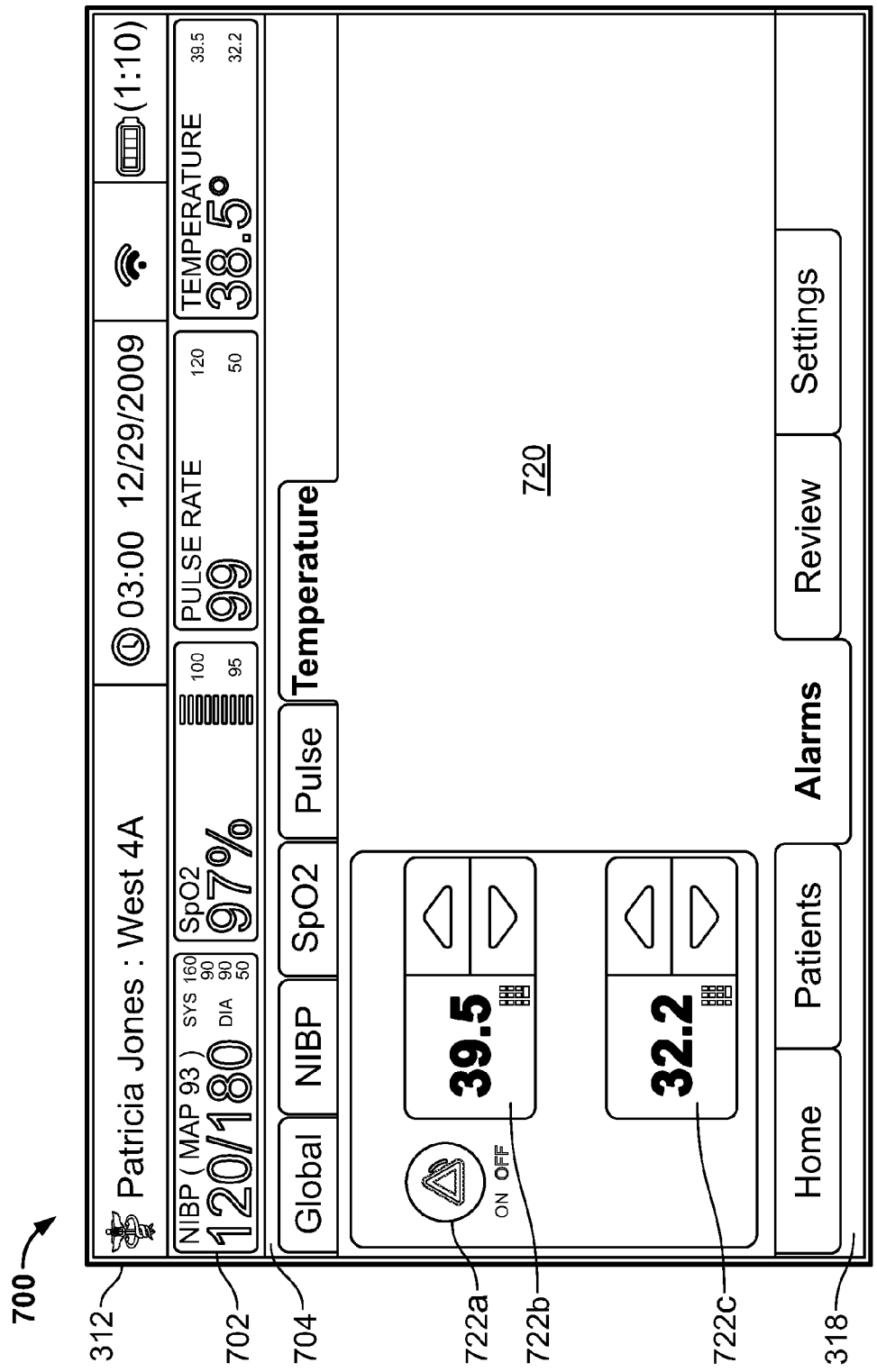
FIG. 7B illustrates an example temperature pane of the alarms screen.

FIG. 7B illustrates an example temperature pane 720 of the alarms screen 700. The alarms screen 700 includes the device status area 312, the compressed parameter reporting area 702, the pane selection tab area 704, the temperature pane 720, and a navigation area 318. The device status area 312, the compressed parameter reporting area 702, the pane selection tab area 704 and the navigation area 318 appear like that of FIG. 7A.

The temperature pane 720 is located below the compressed parameter reporting area 702. The temperature pane 720 enables a user of the PMP device 200 to configure parameter-specific alarm settings for the temperature alarm. In the example of FIG. 7B, the temperature pane 720 provides controls 722a, 722b and 722c. The control 722a sets the temperature alarm to ON or OFF. The control 722b sets an upper temperature limit for the temperature alarm. The control 722c sets a lower temperature limit for the temperature alarm.

Figure 7C:
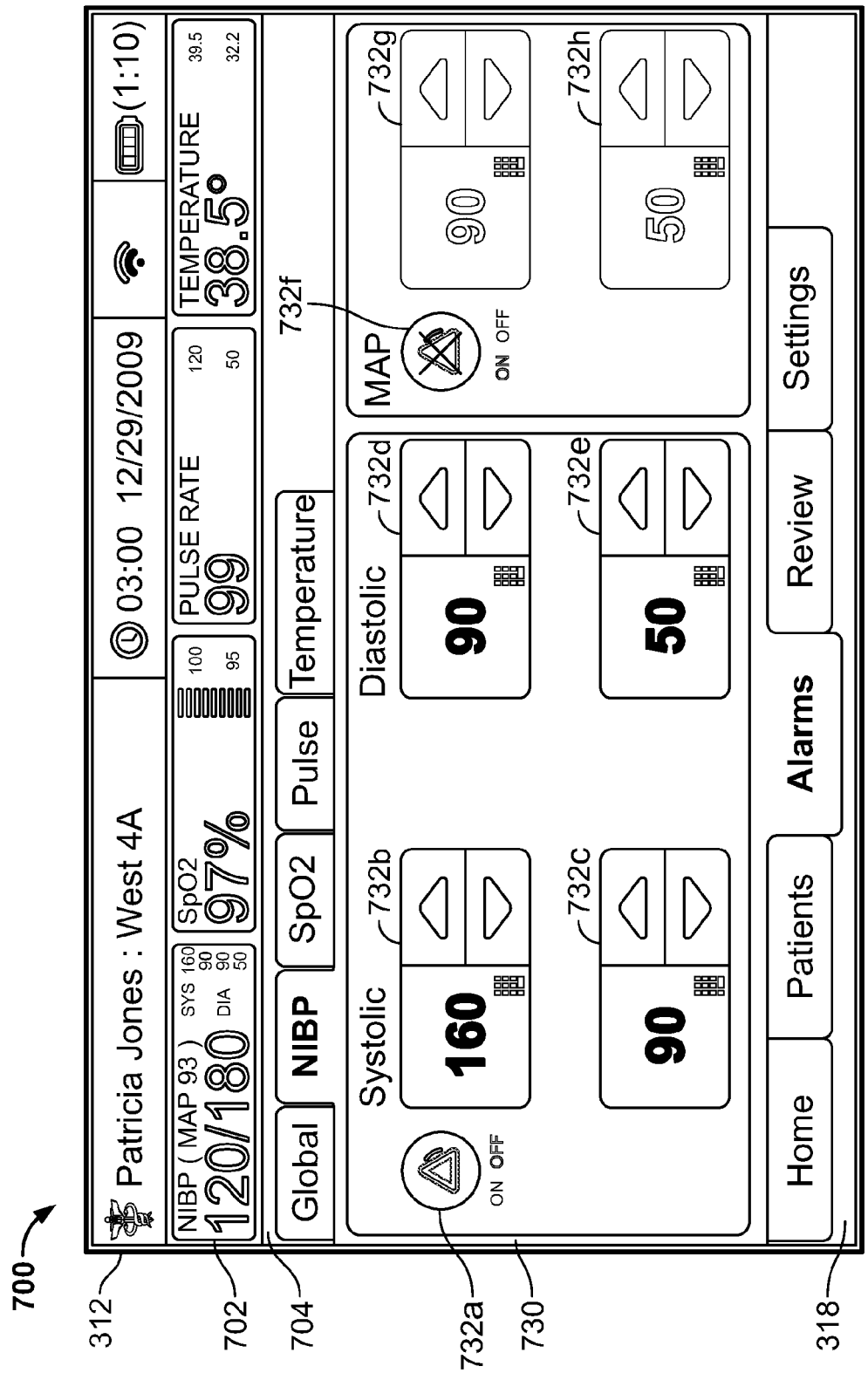
FIG. 7C illustrates an example NIBP pane of the alarms screen.

FIG. 7C illustrates an example NIBP pane 730 of the alarms screen 700. The alarms screen 700 includes a device status area 312, a compressed parameter reporting area 702, a pane selection tab area 704, the NIBP pane 730, and a navigation area 318. The device status area 312, the compressed parameter reporting area 702, the pane selection tab area 704 and the navigation area 318 appear like that of FIG. 7A.

The NIBP pane 730 enables a user of the PMP device 200 to configure parameter-specific alarm settings for the NIBP alarm. In the example of FIG. 7C, the NIBP pane 730 contains a control 732a to set the systolic and diastolic alarm ON or OFF. The NIBP pane 730 also contains controls 732b-732e to set the systolic and diastolic upper and lower alarm limits for the systolic and diastolic alarm. Further, the NIBP pane 730 provides controls 732f, 732g and 732h. The control 732f sets a MAP alarm to ON or OFF. The control 732g sets set an upper MAP limit for the MAP alarm. The control 732h sets a lower MAP limit for the MAP alarm.

Figure 7D:
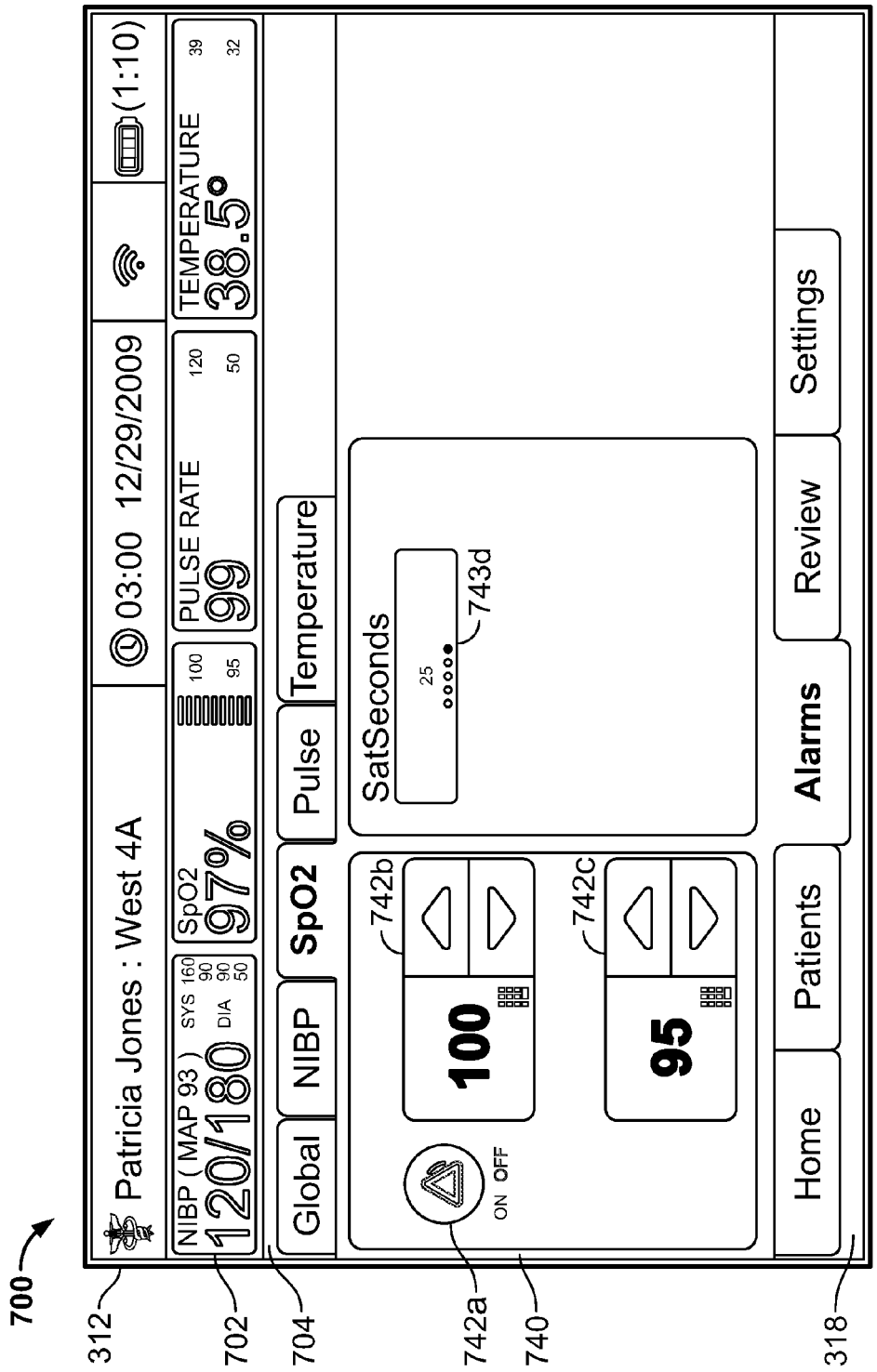
FIG. 7D illustrates an example SpO2 pane of the alarms screen.

FIG. 7D illustrates an example SpO2 pane 740 of the alarms screen 700. The alarms screen 700 includes the device status area 312, the compressed parameter reporting area 702, the pane selection tab area 704, the SpO2 pane 740, and the navigation area 318. The device status area 312, the compressed parameter reporting area 702, the pane selection tab area 704, and the navigation area 318 appear like that of FIG. 7A.

The SpO2 pane 740 enables a user of the PMP device 200 to configure parameter-specific alarm settings for the SpO2 alarm. In the example of FIG. 7D, the SpO2 pane 740 provides controls 742a, 742b and 742c. The control 742a sets the SpO2 alarm to ON or OFF. The controls 742b and 742c set an upper SpO2 limit and a lower SpO2 limit for the SpO2 alarm. The SpO2 pane 740 also includes a SatSeconds™ control 743d. When a numeric value is selected, an SpO2 alarm is not activated until a length of time specified by the SatSeconds control 743d has expired. The length of time specified by the SatSeconds control 743d is based on a duration of a low SpO2 event multiplied by a number of percentage points that the patient's SpO2 falls outside the lower SpO2 alarm threshold. Also, the SatSeconds control 743*d* appears next to the controls 742*b* and 742*c* when the control 742*a* is set to ON. However, when the control 742*a* is set to OFF, the SatSeconds control 743*d* is not displayed and the alarm condition is not delayed per a SatSeconds algorithm.

Figure 7E:
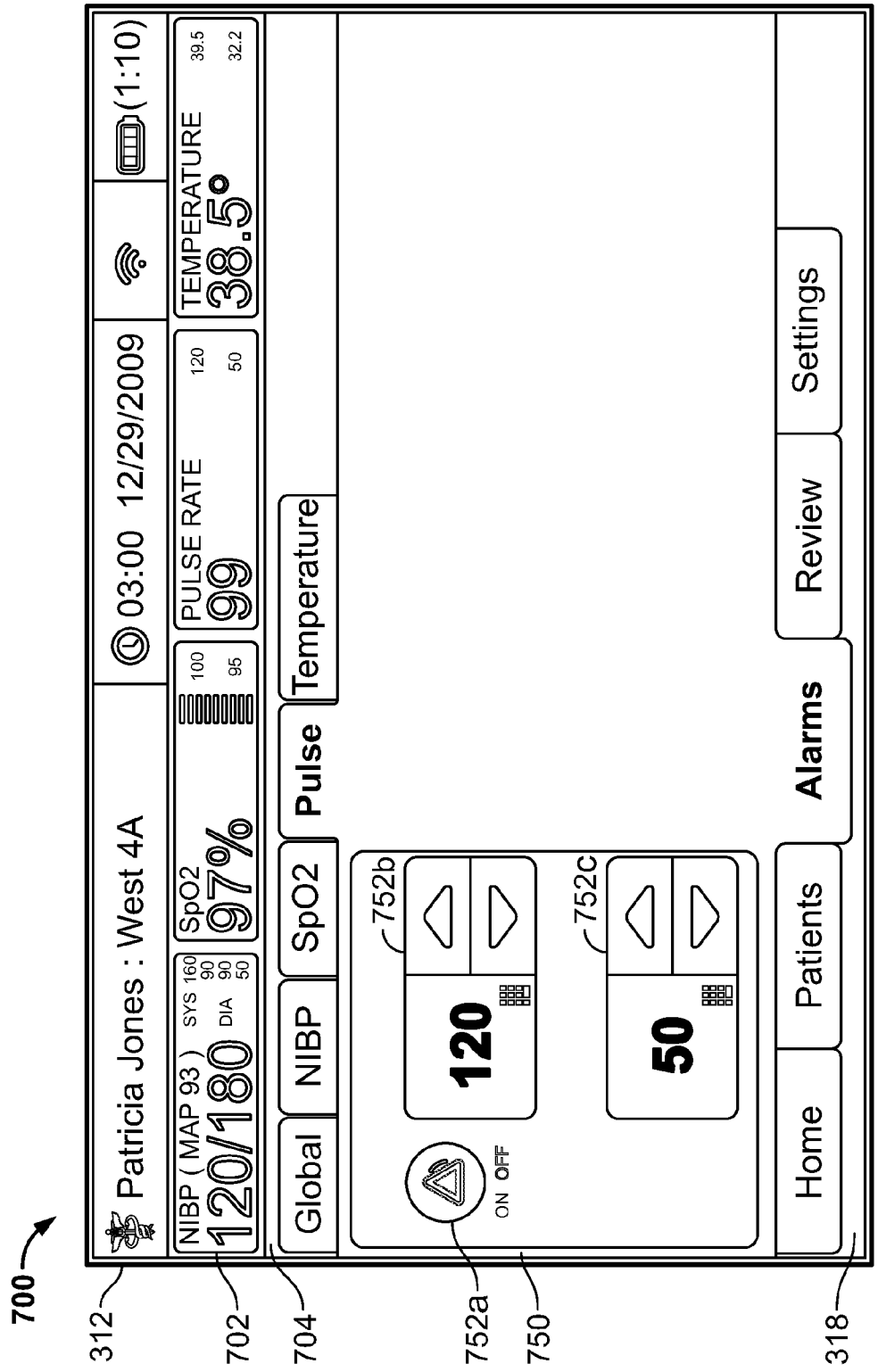
FIG. 7E illustrates an example pulse rate pane of the alarms screen.

FIG. 7E illustrates an example pulse rate pane 750 of the alarms screen 700. The alarms screen 700 includes the device status area 312, the compressed parameter reporting area 702, the pane selection tab area 704, the pulse rate pane 750 and the navigation area 318. The device status area 312, the compressed parameter reporting area 702, the pane selection tab area 704 and the navigation area 318 appear like that of FIG. 7A.

The pulse rate pane 750 enables a user of the PMP device 200 to configure parameter-specific alarm settings for the pulse rate alarm. In the example of FIG. 7E, the pulse rate pane 750 provides an on/off control 752*a*, an upper limit control 752*b* and a lower limit control 752*c*. The on/off control 752*a* allows a user to turn the pulse rate alarm on or off. The upper limit control 752*b* allows a user to set an upper pulse rate limit for the pulse rate alarm. The lower limit control 752*c* allows a user to set a lower pulse rate limit for the pulse rate alarm.

The upper limit control 752*b* includes a numerical portion, an up button and a down button. The numerical portion of the upper limit control 752*b* specifies an upper pulse rate limit for the pulse rate alarm. Selecting the up button of the upper limit control 752*b* incrementally increases the upper pulse rate limit. Selecting the down button of the upper limit control 752*b* incrementally decreases the upper pulse rate limit. Selecting the numerical portion of the upper limit control 752*b* causes the PMP device 200 to display a numerical keypad. The user is able to use the numerical keypad to manually enter a value for the upper pulse rate limit.

The lower limit control 752*c* includes a numerical portion, an up button, and a down button. The numerical portion of the lower limit control 752*c* specifies the lower pulse rate limit. Selecting the up button of the lower limit control 752*c* incrementally increases the lower pulse rate limit. Selecting the down button of the lower limit control 752*c* incrementally decreases the lower pulse rate limit. Selecting the numerical portion of the lower limit control 752*c* causes the PMP device 200 to display a numerical keypad. The user is able to use the numerical keypad to manually enter a value for the lower pulse rate limit.

In the examples shown, the values that are entered by the user are validated for accuracy. For example, upper and lower thresholds for each parameter can be set. If the user selects a value outside of the upper and lower thresholds, the system can prevent such a selection and/or alert the user. For example, if the user types in 300 minutes on the keypad for a parameter, and the upper threshold set for that parameter is 240 minutes, the system will not allow the user to increase the parameter to 300 minutes.

In some embodiments, various panes of the alarms screen 700 can include other upper limit controls and other lower limit controls like the upper limit control 752*b* and the lower limit control 752*c*. The other upper limit controls and the other lower limit controls allow a user to set upper limits and lower limits for alarms for various physiological parameters of patients.

Figure 8:
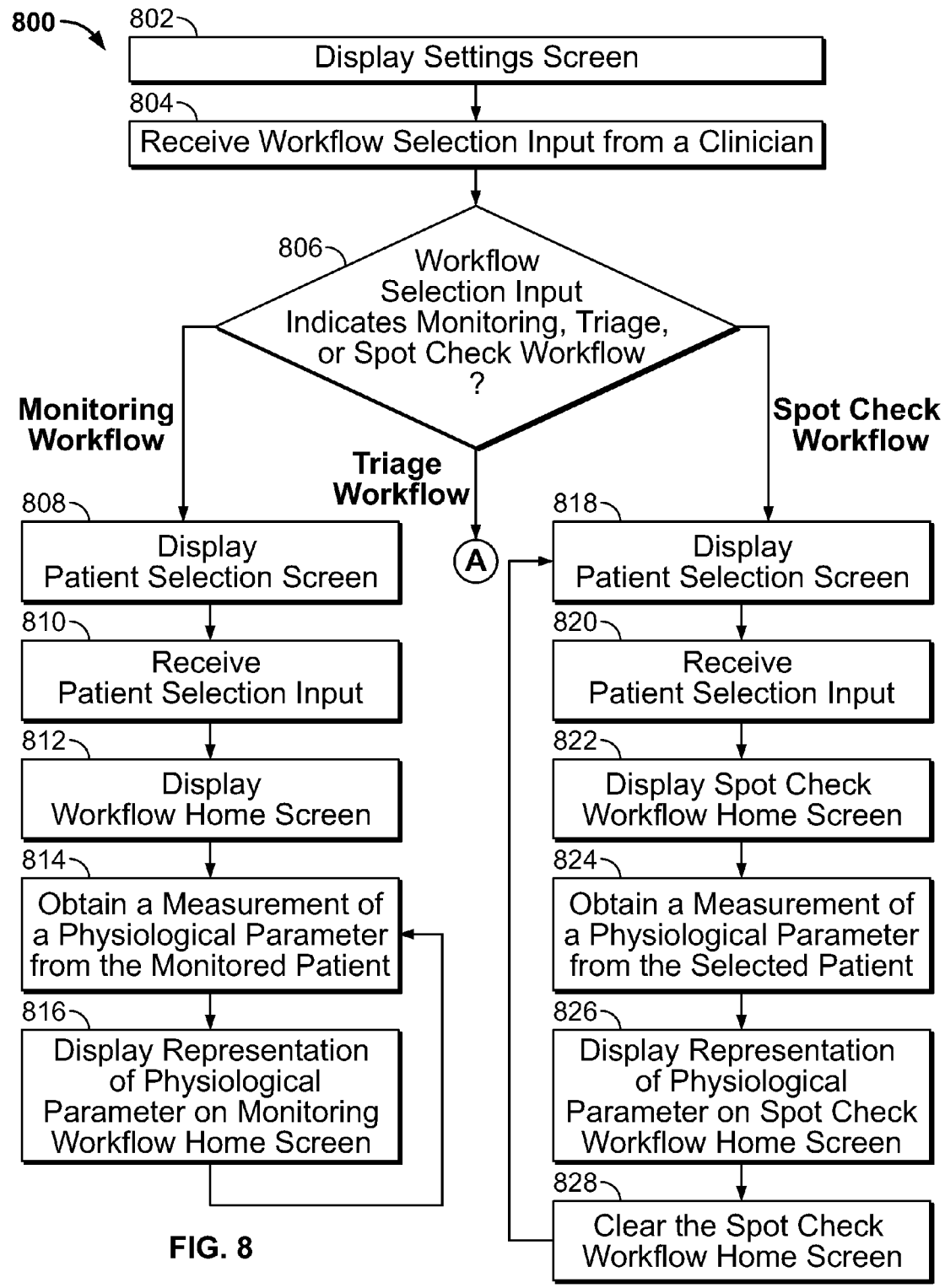
FIG. 8 is a flowchart illustrating an example operation performed by the PMP device.

FIG. 8 is a flowchart illustrating an example operation 800 performed by the PMP device 200. As illustrated in the example of FIG. 8, the operation 800 begins when the PMP device 200 displays the settings screen 600 (802). The PMP device 200 then receives workflow selection input from a clinician via the settings screen 600 (804). In response to receiving the workflow selection input, the PMP device 200 determines whether the workflow selection input indicates the monitoring workflow, the triage workflow, or the spot check workflow (806). If the PMP device 200 determines that the workflow selection input indicates the triage workflow, the PMP device 200 performs the steps illustrated in FIG. 9.

If the PMP device 200 determines that the workflow selection input indicates the monitoring workflow, the PMP device 200 displays the patient selection screen 400 (808). The PMP device 200 then receives patient selection input from the clinician via the patient selection screen 400 (810). The patient selection input indicates a patient that the clinician intends to monitor.

Next, the PMP device 200 displays the monitoring workflow home screen 300 (812). In some embodiments, the PMP device 200 displays the monitoring workflow home screen 300 automatically after the clinician selects the monitored patient via the patient selection screen 400. In other embodiments, the PMP device 200 displays the monitoring workflow home screen 300 in response to the clinician selecting the home tab 319*a*.

Subsequently, the PMP device 200 obtains a measurement of a physiological parameter of the monitored patient (814). The PMP device 200 then displays a representation of the physiological parameter on the monitoring workflow home screen 300 (816). The representation of the physiological parameter is based, at least in part, on the measurement of the physiological parameter. The PMP device 200 then obtains another measurement of the physiological parameter from the same monitored patient (814). In this way, the PMP device 200 enables the clinician to monitor the physiological parameters of the same monitored patient over a period of time.

If, however, the PMP device 200 determines that the workflow selection input indicates the spot check workflow, the PMP device 200 displays the patient selection screen 400 (818). In various embodiments, the PMP device 200 displays the patient selection screen 400 in response to various events. For example, in some embodiments, the PMP device 200 automatically displays the patient selection screen 400 when the PMP device 200 determines that the workflow selection input indicates the spot check workflow. In another example, the PMP device 200 displays the patient selection screen 400 in response to receiving a selection of the patients tab 319*b*.

The PMP device 200 then receives patient selection input from the clinician via the patient selection screen 400 (820). The patient selection input indicates a selected patient. The selected patient is a patient on whom the clinician intends to perform a spot check.

Next, the PMP device 200 displays the spot check workflow home screen 330 (822). In various embodiments, the PMP device 200 displays the spot check workflow home screen 330 in response to various events. For example, in some embodiments, the PMP device 200 automatically displays the spot check workflow home screen 330 when the PMP device 200 receives the patient selection input from the clinician. In other embodiments, the PMP device 200 displays the spot check workflow home screen 330 in response to receiving a selection of the home tab 319*a*.

The PMP device 200 then obtains a measurement of a physiological parameter of the selected patient (824). In response to obtaining the measurement of the physiological parameter of the selected patient, the PMP device 200 displays a representation of the physiological parameter of the selected patent (826). The representation of the physiological parameter is based, at least in part, on the measurement of the physiological parameter.

Subsequently, the PMP device 200 clears the home screen data from the spot check workflow home screen 330 (828). The PMP device 200 then displays the patient selection screen 400 again (818) and receives patient selection input indicating another patient (818), and so on. In this way, the PMP device 200 displays representations of physiological parameters of each patient in a series of patients.

Figure 9:
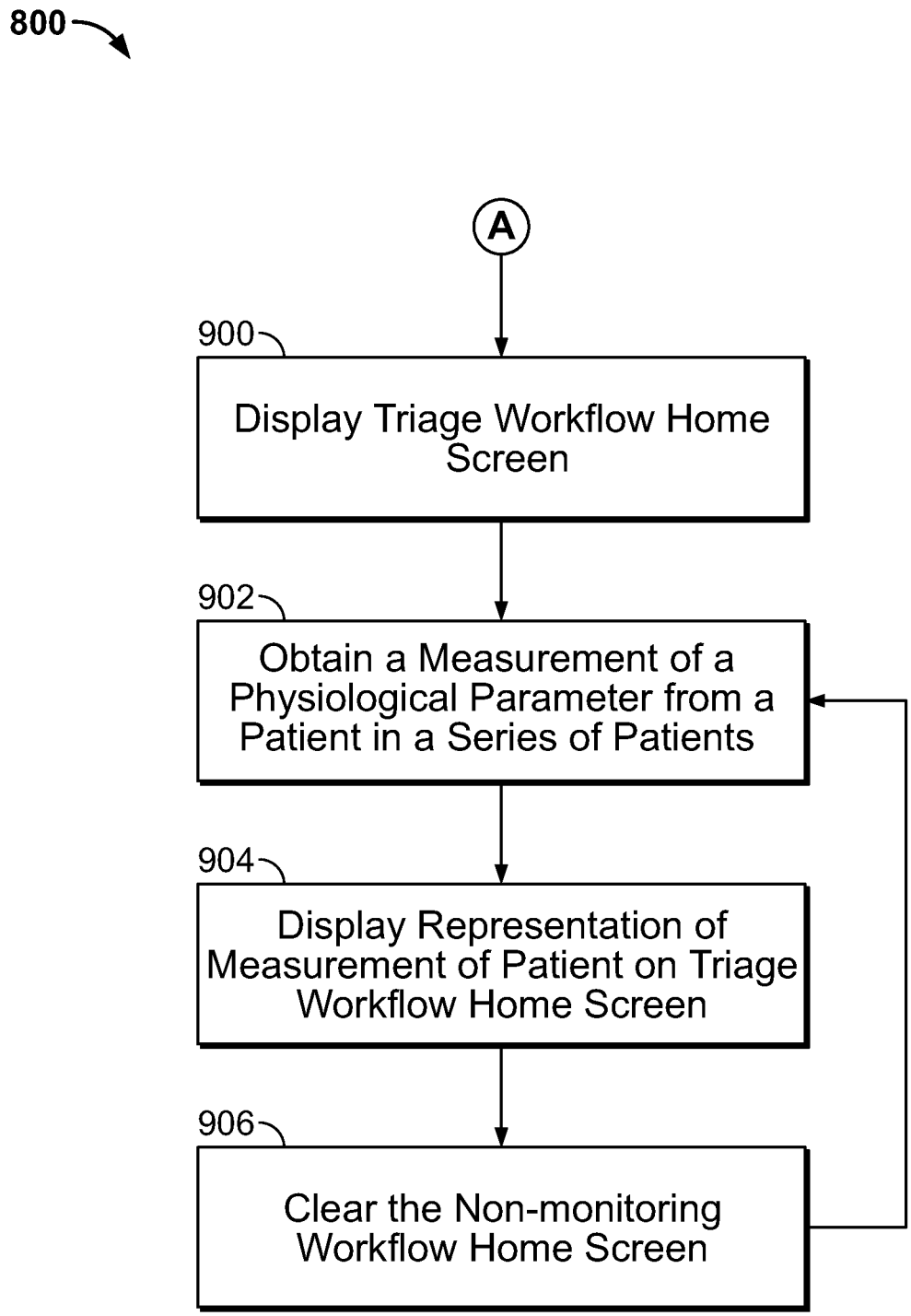
FIG. 9 is a flowchart representing a continuation of the operation in which the workflow selection input indicates the triage workflow.

FIG. 9 is a flowchart representing a continuation of the operation 800 in which the workflow selection input indicates the triage workflow. As illustrated in the example of FIG. 9, if the PMP device 200 determines that the workflow selection input indicates the triage workflow, the PMP device 200 displays the triage workflow home screen 360 (900). In various embodiments, the PMP device 200 displays the triage workflow home screen 360 in response to various events. For example, in some embodiments, the PMP device 200 automatically displays the triage workflow home screen 360 when the PMP device 200 determines that the workflow selection input indicates the triage workflow. In another example, the PMP device 200 displays the triage workflow home screen 360 when the PMP device 200 receives a selection of the home tab 319a.

Next, the PMP device 200 obtains a measurement of a physiological parameter of an unidentified patient in a series of patients (902). After obtaining the measurement, the PMP device 200 displays a representation of the physiological parameter on the triage workflow home screen 360 (904). The representation of the physiological parameter is based at least in part on the measurement of the physiological parameter.

Subsequently, the PMP device 200 clears the home screen data from the triage workflow home screen 360 (906). The PMP device 200 then obtains a measurement of the physiological parameter of a different patient in the series of unidentified patients (902), displays a representation of the physiological parameter (904), and so on. In this way, the PMP device 200 displays representations of physiological parameters of each patient in the series of unidentified patients.

Figure 10:
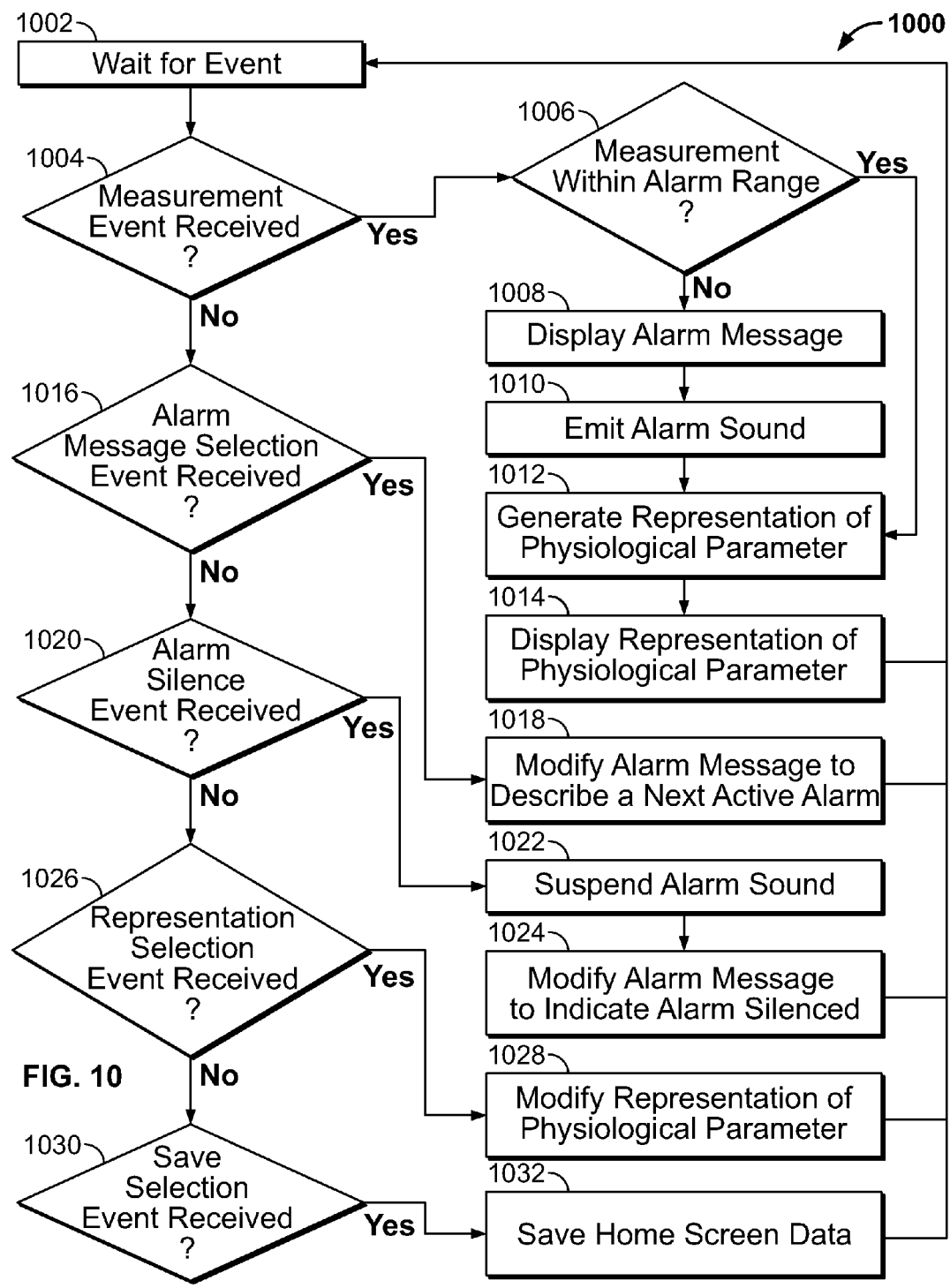
FIG. 10 is a flowchart illustrating an operation performed by the PMP device when the PMP device displays a workflow home screen.

FIG. 10 is a flowchart illustrating an operation 1000 performed by the PMP device 200 when the PMP device 200 displays a workflow home screen. In some embodiments, the PMP device 200 can perform the operation 1000 when the PMP device 200 displays either the monitoring workflow home screen 300, the spot check workflow home screen 330, or the triage workflow home screen 360.

As illustrated in the example of FIG. 10, the PMP device 200 initially waits to receive an event (1002). An event is an occurrence or happening of significance to a task or program.

The PMP device 200 receives a measurement event when the PMP device 200 receives a measurement of a physiological parameter of a patient. If the PMP device 200 receives a measurement event ("YES" of 1004), the PMP device 200 determines whether the measurement of the physiological parameter is within an alarm range for the physiological parameter (1006). If the measurement of the physiological parameter is not within (i.e., is outside) the alarm range for the physiological parameter ("NO" of 1006), the PMP device 200 displays an alarm message on the workflow home screen (1008). In addition, the PMP device 200 emits an alarm sound (1010).

The PMP device 200 also generates a representation of the physiological parameter based on the measurement of the physiological parameter (1012). The PMP device 200 generates the representation of the physiological parameter regardless of whether the measurement is within the alarm range of the physiological parameter. The PMP device 200 then displays the representation of the physiological parameter on the workflow home screen (1014). The PMP device 200 then waits for another event (1002).

The PMP device 200 can receive an alarm message selection event when the PMP device 200 displays an alarm message, there are two or more active alarms, and a clinician selects the alarm message. If the PMP device 200 receives an alarm message selection event ("YES" of 1016), the PMP device 200 modifies the alarm message such that the alarm message describes a next one of the active alarms (1018). The PMP device 200 then waits for another event (1002).

The PMP device 200 can receive an alarm silence event when an alarm is currently active, the PMP device 200 is emitting an alarm sound, and a clinician selects a control to suspend the alarm sound. If the PMP device 200 receives an alarm silence event ("YES" of 1020), the PMP device 200 suspends the alarm sound (1022). In addition, the PMP device 200 modifies the alarm message to indicate that the alarm has been silenced (1024). The PMP device 200 then waits for another event (1002).

The PMP device 200 can receive a representation selection event when a clinician selects a representation of a physiological parameter. If the PMP device 200 receives a representation selection event ("YES" of 1026), the PMP device 200 modifies a parameter reporting area associated with the physiological parameter such that the parameter reporting area contains a different representation of the physiological parameter (1028). The PMP device 200 then waits for another event (1002).

The PMP device 200 can receive a save selection event when a clinician selects a save button (e.g., save button 316g) on the workflow home screen. If the PMP device 200 receives a save selection event ("YES" of 1030), the PMP device 200 saves the home screen data (1032). The PMP device 200 then waits for another event (1002).

Figure 11:
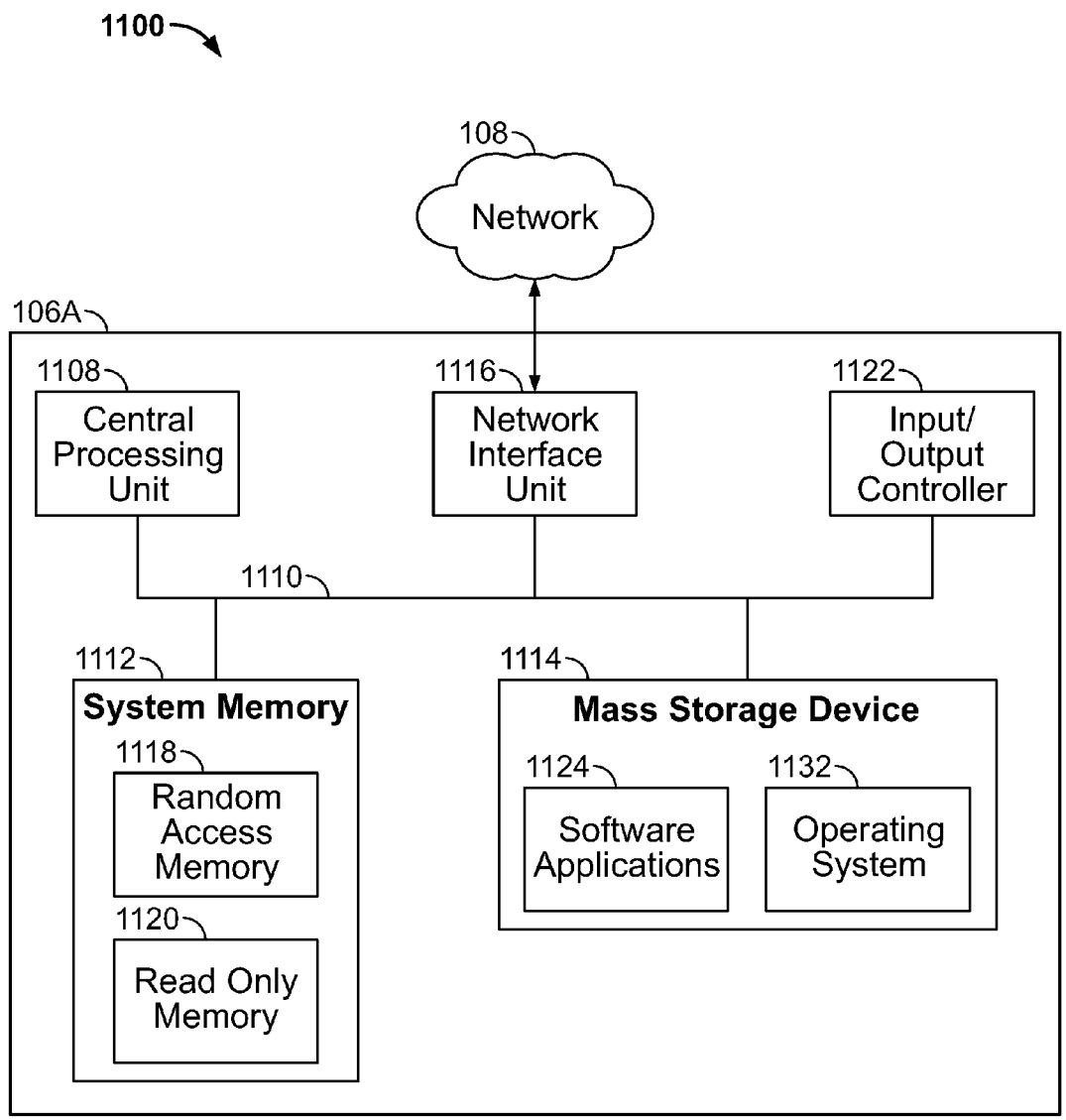
FIG. 11 illustrates example physical components of the PMP device.

FIG. 11 illustrates example physical components of the PMP device 200. As illustrated in the example of FIG. 11, the PMP device 200 include at least one central processing unit ("CPU") 1108, a system memory 1112, and a system bus 1110 that couples the system memory 1112 to the CPU 1108. The system memory 1112 includes a random access memory ("RAM") 1118 and a read-only memory ("ROM") 1120. A basic input/output system containing the basic routines that help to transfer information between elements within the PMP device 200, such as during startup, is stored in the ROM 1120. The PMP device 200 further includes a mass storage device 1114. The mass storage device 1114 is able to store software instructions and data.

The mass storage device 1114 is connected to the CPU 1108 through a mass storage controller (not shown) connected to the bus 1110. The mass storage device 1114 and its associated computer-readable data storage media provide non-volatile, non-transitory storage for the PMP device 200. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the PMP device 200 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the PMP device 200.

According to various embodiments of the invention, the PMP device 200 may operate in a networked environment using logical connections to remote network devices through the network 108, such as a local network, the Internet, or another type of network. The PMP device 200 connects to the network 108 through a network interface unit 1116 connected to the bus 1110. It should be appreciated that the network interface unit 1116 may also be utilized to connect to other types of networks and remote computing systems. The PMP device 200 also includes an input/output controller 1122 for receiving and processing input from a number of other devices, including a keyboard, a mouse, a touch user interface display screen, or another type of input device. Similarly, the input/output controller 1122 may provide output to a touch user interface display screen, a printer, or other type of output device.

As mentioned briefly above, the mass storage device 1114 and the RAM 1118 of the PMP device 200 can store software instructions and data. The software instructions include an operating system 1132 suitable for controlling the operation of the PMP device 200. The mass storage device 1114 and/or the RAM 1118 also store software instructions, that when executed by the CPU 1108, cause the PMP device 200 to provide the functionality of the PMP device 200 discussed in this document. For example, the mass storage device 1114 and/or the RAM 1118 can store software instructions that, when executed by the CPU 1108, cause the PMP device to display the monitoring workflow home screen 300 and other screens.

It should be appreciated that various embodiments can be implemented (1) as a sequence of computer implemented acts or program modules running on a computing system and/or (2) as interconnected machine logic circuits or circuit modules within the computing system. The implementation is a matter of choice dependent on the performance requirements of the computing system implementing the invention. Accordingly, logical operations including related algorithms can be referred to variously as operations, structural devices, acts or modules. It will be recognized by one skilled in the art that these operations, structural devices, acts and modules may be implemented in software, firmware, special purpose digital logic, and any combination thereof without deviating from the spirit and scope of the present invention as recited within the claims set forth herein.

Although the invention has been described in connection with various embodiments, those of ordinary skill in the art will understand that many modifications may be made thereto within the scope of the claims that follow. For example, it should be appreciated that the screens illustrated in this document are merely examples and that in other embodiments equivalent screens can have different contents and appearances. Accordingly, it is not intended that the scope of the invention in any way be limited by the above description, but instead be determined entirely by reference to the claims that follow.

What is claimed is:

1. A physiological measuring platform (PMP) device comprising:
    a central processing unit (CPU) that is configured to control operation of the PMP device;
    a display screen; and
    a set of one or more computer-readable data storage media storing software instructions that, when executed by the CPU, cause the PMP device to:
        display, on the display screen, a monitoring workflow home screen when the PMP device is operating within a monitoring workflow, wherein the monitoring workflow home screen includes a first blood pressure measurement display of a first size;
        obtain a series of measurements of a physiological parameter of a monitored patient when the PMP device is operating within the monitoring workflow;
        display, on the display screen, a non-monitoring workflow home screen when the PMP device is operating within a non-monitoring workflow, wherein the non-monitoring workflow home screen includes a second blood pressure measurement display of a second size, the second size being larger than the first size;
        obtain a measurement of the physiological parameter of each patient in a series of patients when the PMP device is operating within the non-monitoring workflow;
        display, on the display screen, a patient selection screen including a patient listing area, the patient listing area displaying a plurality of patient names
        display an intervals screen, the intervals screen being navigable from the monitoring workflow home screen, wherein the intervals screen includes a user-selectable duration control and a user-selectable interval control,
            wherein the user-selectable duration control sets a first length of time during which the PMP device records measurements for a given physiological Parameter; and
            wherein the user-selectable interval control sets a second length of time between measurements recorded by the PMP device.

2. The PMP device of claim 1, further comprising software instructions that, when executed by the CPU, cause the PMP device to:
    display, on the display screen, a review screen including patient data,
    wherein the patient selection screen includes user-selectable controls to add, delete, and select one of the plurality of patient names.

3. The PMP device of claim 2, wherein the patient data in the review screen includes: patient name, date and time, and the physiological parameter.

4. The PMP device of claim 3, wherein the review screen further includes user-selectable controls to send, print, and delete one or more entries.

5. The PMP device of claim 4, wherein the patient data displayed on the review screen includes physiological data for a plurality of patients; and
    wherein the physiological data includes at least one of: blood pressure, temperature, respiration rate, SpO2, height, and weight.

6. The PMP device of claim 5, wherein the review screen further includes a user-selectable control to view patient data by at least one of: sent data, unsent data, and alarm data.

7. The PMP device of claim 1, wherein the monitoring workflow home screen includes a user-selectable save control, the user-selectable save control configured to save a patient reading, the patient reading including measurements of the physiological parameter of the patient.

8. The PMP device of claim 1, wherein, when an alarm is active for a particular physiological parameter, a parameter reporting frame for the particular physiological parameter displayed on the monitoring workflow home screen transitions from a gray color to a red color.

9. The PMP device of claim 8, wherein the parameter reporting frame further includes a bell symbol, the bell symbol transitioning from a white color to a yellow color or a red color based on a priority of the alarm.

10. A method for obtaining a physiological parameter associated with a patient, comprising:
   obtaining, by a physiological measuring platform (PMP) device, a measurement of the physiological parameter of the patient;
   displaying, on a display screen, a monitoring workflow home screen when the PMP device is operating within a monitoring workflow, the monitoring workflow home screen containing at least one first parameter reporting area containing a representation of the physiological parameter of the patient;
   displaying on the display screen, a non-monitoring workflow home screen when the PMP device is operating within a non-monitoring workflow, the non-monitoring workflow home screen containing at least one second parameter reporting area containing a representation of the physiological parameter of the patient;
   displaying, on the display screen, a patient selection screen including a patient listing area, the patient listing area displaying a plurality of patient names, wherein the patient selection screen includes user-selectable controls to add, delete, and select one of the plurality of patient names;
   displaying, on the display screen, a review screen including patient data including patient name, date and time, and the physiological parameter; and
   displaying, on the display screen, an intervals screen, the intervals screen being navigable from the monitoring workflow home screen, wherein the intervals screen includes a user-selectable duration control and a user-selectable interval control,
      wherein the user-selectable duration control sets a first length of time during which the PMP device records measurements for a given physiological parameter; and
      wherein the user-selectable interval control sets a second length of time between measurements recorded by the PMP device.

11. The method of claim 10, wherein the review screen further includes user-selectable controls to send, print, and delete one or more entries;
   wherein the patient data displayed on the review screen includes physiological data for a plurality of patients; and
   wherein the physiological data includes at least one of: blood pressure, temperature, respiration rate, SpO2, height, and weight.

12. The method of claim 11, wherein the review screen further includes a user-selectable control to view patient data by at least one of: sent data, unsent data, and alarm data;
   wherein the monitoring workflow home screen includes a first blood pressure measurement display of a first size; and
   wherein the non-monitoring workflow home screen includes a second blood pressure measurement display of a second size, the second size being larger than the first size.

13. The method of claim 12, wherein the monitoring workflow home screen includes a user-selectable save control, the user-selectable save control configured to save a patient reading, the patient reading including measurements of the physiological parameter of the patient.

14. The method of claim 13, wherein when an alarm is active for a particular physiological parameter, a parameter reporting frame for the particular physiological parameter displayed on the monitoring workflow home screen transitions from a gray color to a red color; and
   wherein the parameter reporting frame further includes a bell symbol, the bell symbol transitioning from a white color to a yellow color or a red color based on a priority of the alarm.

15. A physiological measuring platform (PMP) device comprising:
   a central processing unit (CPU) that is configured to control operation of the PMP device;
   a display screen; and
   a set of one or more computer-readable data storage media storing software instructions that, when executed by the CPU, cause the PMP device to:
      display, on the display screen, a monitoring workflow home screen when the PMP device is operating within a monitoring workflow;
      obtain a series of measurements of a physiological parameter of a monitored patient when the PMP device is operating within the monitoring workflow;
      display, on the display screen, a non-monitoring workflow home screen when the PMP device is operating within a non-monitoring workflow;
      obtain a measurement of the physiological parameter of each patient in a series of patients when the PMP device is operating within the non-monitoring workflow;
      display, on the display screen, a patient selection screen including a patient listing area, the patient listing area displaying a plurality of patient names, wherein the patient selection screen additionally includes user-selectable controls to add, delete, and select one of the plurality of patient names;
      display, on the display screen, a review screen including patient data including patient name, date and time, and the physiological parameter, the review screen additionally including user-selectable controls to send, print, and delete one or more entries; and
      display, on the display screen, an intervals screen, the intervals screen being navigable from the monitoring workflow home screen, wherein the intervals screen includes a user-selectable duration control and a user-selectable interval control,
         wherein the user-selectable duration control sets a first length of time during which the PMP device records measurements for a given physiological parameter; and
         wherein the user-selectable interval control sets a second length of time between measurements recorded by the PMP device.

16. The PMP device of claim 15, wherein the patient data displayed on the review screen includes physiological data for a plurality of patients;
- wherein the physiological data includes at least one of: blood pressure, temperature, respiration rate, SpO2, height, and weight; and
- wherein the review screen further includes a user-selectable control to view patient data by at least one of: sent data, unsent data, and alarm data.

17. The PMP device of claim 16, wherein the monitoring workflow home screen includes a first blood pressure measurement display of a first size;
- wherein the non-monitoring workflow home screen includes a second blood pressure measurement display of a second size, the second size being larger than the first size; and
- wherein the monitoring workflow home screen includes a user-selectable save control, the user-selectable save control configured to save a patient reading, the patient reading including measurements of the physiological parameter of the patient.

18. The PMP device of claim 17, wherein when an alarm is active for a particular physiological parameter, a parameter reporting frame for the particular physiological parameter displayed on the monitoring workflow home screen transitions from a gray color to a red color; and
- wherein the parameter reporting frame further includes a bell symbol, the bell symbol transitioning from a white color to a yellow color or a red color based on a priority of the alarm.

* * * * *

UNITED STATES PATENT AND TRADEMARK OFFICE
CERTIFICATE OF CORRECTION

PATENT NO. : 9,646,136 B2
APPLICATION NO. : 14/994576
DATED : May 9, 2017
INVENTOR(S) : St. Pierre et al.

It is certified that error appears in the above-identified patent and that said Letters Patent is hereby corrected as shown below:

On the Title Page

Page 3, Line 49: "ofr" should read --of--

Page 3, Line 51: "Inernational" should read --International--

Page 3, Line 59: "Confernece" should read --Conference--

Page 3, Line 66: "Retrived" should read --Retrieved--

Signed and Sealed this
Fifth Day of December, 2017

Joseph Matal
*Performing the Functions and Duties of the
Under Secretary of Commerce for Intellectual Property and
Director of the United States Patent and Trademark Office*